(12) United States Patent
Gao et al.

(10) Patent No.: US 11,739,346 B2
(45) Date of Patent: Aug. 29, 2023

(54) MINIGENE THERAPY

(71) Applicant: University of Massachusetts, Boston, MA (US)

(72) Inventors: Guangping Gao, Westborough, MA (US); Hemant Khanna, Sutton, MA (US)

(73) Assignee: University of Massachusetts, Boston, MA (US)

( * ) Notice: Subject to any disclaimer, the term of this patent is extended or adjusted under 35 U.S.C. 154(b) by 816 days.

(21) Appl. No.: 16/500,238

(22) PCT Filed: Apr. 5, 2018

(86) PCT No.: PCT/US2018/026230
§ 371 (c)(1),
(2) Date: Oct. 2, 2019

(87) PCT Pub. No.: WO2018/187552
PCT Pub. Date: Oct. 11, 2018

(65) Prior Publication Data
US 2020/0056204 A1 Feb. 20, 2020

Related U.S. Application Data

(60) Provisional application No. 62/481,727, filed on Apr. 5, 2017.

(51) Int. Cl.
| | | |
|---|---|---|
| *C07H 21/04* | (2006.01) | |
| *C12N 15/63* | (2006.01) | |
| *A61K 31/70* | (2006.01) | |
| *C12N 15/86* | (2006.01) | |
| *A61P 27/02* | (2006.01) | |
| *A61K 9/00* | (2006.01) | |
| *A61K 35/761* | (2015.01) | |
| *C07K 14/47* | (2006.01) | |
| *C12N 7/00* | (2006.01) | |
| *A01K 67/00* | (2006.01) | |
| *A61K 48/00* | (2006.01) | |

(52) U.S. Cl.
CPC ............ *C12N 15/86* (2013.01); *A61K 9/0048* (2013.01); *A61K 35/761* (2013.01); *A61P 27/02* (2018.01); *C07K 14/47* (2013.01); *C12N 7/00* (2013.01); *A61K 48/00* (2013.01); *C12N 2750/14143* (2013.01)

(58) Field of Classification Search
CPC ................................. C12N 15/86; C12N 7/00; C12N 2750/14143; A61P 27/02; A61K 48/00; A61K 9/0048
See application file for complete search history.

(56) References Cited

U.S. PATENT DOCUMENTS

| | | | |
|---|---|---|---|
| 5,478,745 A | 12/1995 | Samulski et al. | |
| 5,552,157 A | 9/1996 | Yagi | |
| 5,565,213 A | 10/1996 | Nakamori et al. | |
| 5,567,434 A | 10/1996 | Szoka, Jr. | |
| 5,738,868 A | 4/1998 | Shinkarenko | |
| 5,741,516 A | 4/1998 | Webb et al. | |
| 5,795,587 A | 8/1998 | Gao et al. | |
| 6,001,650 A | 12/1999 | Colosi | |
| 6,156,303 A | 12/2000 | Russell et al. | |
| 10,155,794 B2 | 12/2018 | Drivas et al. | |
| 10,253,312 B2 | 4/2019 | Maeder et al. | |
| 10,266,845 B2 | 4/2019 | Cronin et al. | |
| 2003/0138772 A1 | 7/2003 | Gao et al. | |
| 2011/0117058 A1 | 5/2011 | Auricchio | |
| 2016/0076054 A1 | 3/2016 | Auricchio et al. | |
| 2016/0185832 A1 | 6/2016 | Drivas et al. | |
| 2016/0194374 A1 | 7/2016 | Wijnholds et al. | |
| 2017/0275615 A1 | 9/2017 | Wu et al. | |
| 2017/0348387 A1* | 12/2017 | Aguirre et al. | |
| 2018/0369412 A1 | 12/2018 | Bennett et al. | |
| 2019/0002916 A1 | 1/2019 | Kalatzis et al. | |
| 2019/0062385 A1 | 2/2019 | Drivas et al. | |
| 2020/0056204 A1 | 2/2020 | Gao et al. | |

FOREIGN PATENT DOCUMENTS

| | | |
|---|---|---|
| CN | 105408352 A | 3/2016 |
| WO | WO 1998/010088 A1 | 3/1998 |
| WO | WO 2014/170480 A1 | 10/2014 |
| WO | WO 2015/009575 A1 | 1/2015 |
| WO | WO 2016/033338 A1 | 3/2016 |
| WO | WO 2018/187552 A1 | 10/2018 |
| WO | WO 2019/006182 A1 | 1/2019 |
| WO | WO 2019/077159 A1 | 4/2019 |

OTHER PUBLICATIONS

NCBI Reference Sequence: NM_025114.2. *Homo sapiens* centrosomal protein 290kDa(CEP290), mRNA.; 4 pages, (Year: 2006).*
PCT/US2018/026230, Jul. 23, 2018, International Search Report and Written Opinion.
PCT/US2018/026230, Oct. 17, 2019, International Preliminary Report on Patentability.
Extended European Search Report for Application No. EP 18781286.2, dated Mar. 11, 2021.
Boshart et al., A very strong enhancer is located upstream of an immediate early gene of human cytomegalovirus. Cell. 1985;41(2):521-530. doi:10.1016/s0092-8674(85)80025-8.

(Continued)

*Primary Examiner* — Quang Nguyen
(74) *Attorney, Agent, or Firm* — Wolf, Greenfield & Sacks, P.C.

(57) ABSTRACT

Aspects of the disclosure relate to compositions and methods useful for treating ocular ciliopathies, for example Leber congenital amaurosis (LCA). In some embodiments, the disclosure provides isolated nucleic acids comprising a transgene encoding a CEP290 protein fragment, and methods of treating ocular ciliopathies using the same.

16 Claims, 19 Drawing Sheets

Specification includes a Sequence Listing.

(56) References Cited

OTHER PUBLICATIONS

Boye et al., Natural history of cone disease in the murine model of Leber congenital amaurosis due to CEP290 mutation: determining the timing and expectation of therapy. PLoS One. Mar. 26, 2014;9(3):e92928. doi: 10.1371/journal.pone.0092928.

Chu et al., SV40 DNA transfection of cells in suspension: analysis of the efficiency of transcription and translation of T-antigen. Gene. 1981;13:197-202.

De Felipe et al., Use of the 2A sequence from foot-and-mouth disease virus in the generation of retroviral vectors for gene therapy. Gene Ther. 1999;6(2):198-208. doi:10.1038/sj.gt.3300811.

Den Hollander et al., Mutations in the CEP290 (NPHP6) gene are a frequent cause of Leber congenital amaurosis. Am J Hum Genet. 2006;79(3):556-561. doi:10.1086/507318.

Fisher et al., Transduction with recombinant adeno-associated virus for gene therapy is limited by leading-strand synthesis. J Virol. Jan. 1996; 70(1): 520-532.

Furler et al., Recombinant AAV vectors containing the foot and mouth disease virus 2A sequence confer efficient bicistronic gene expression in cultured cells and rat substantia nigra neurons. Gene Therapy. Jun. 22, 2001;8:864-873.

GENBANK Accession No. NP_079390.3. Jan. 5, 2020. 4 pages.

Gossen et al., Tight control of gene expression in mammalian cells by tetracycline-responsive promoters. Proc Natl Acad Sci U S A. 1992;89(12):5547-5551. doi: 10.1073/pnas.89.12.5547.

Graham et al., A new technique for the assay of infectivity of human adenovirus 5 DNA. Virology. 1973;52(2):456-467. doi:10.1016/0042-6822(73)90341-3.

Halpin et al., Self-processing 2A-polyproteins—a system for co-ordinate expression of multiple proteins in transgenic plants. Plant J. 1999;17(4):453-459. doi:10.1046/j.1365-313x.1999.00394.x.

Harvey et al., Inducible control of gene expression: prospects for gene therapy. Curr Opin Chem Biol. 1998;2(4):512-518. doi:10.1016/s1367-5931(98)80128-2.

Klump et al., Retroviral vector-mediated expression of HoxB4 in hematopoietic cells using a novel coexpression strategy. Gene Therapy. Jun. 22, 2001;8:811-817. doi: https://doi.org/10.1038/sj.gt.3301447.

Magari et al., Pharmacologic control of a humanized gene therapy system implanted into nude mice. J Clin Invest. Dec. 1, 1997; 100(11): 2865-2872. doi: 10.1172/JCI119835.

Mattion et al., Foot-and-mouth disease virus 2A protease mediates cleavage in attenuated Sabin 3 poliovirus vectors engineered for delivery of foreign antigens. J Virol. Nov. 1996; 70(11): 8124-8127.

Mccarty et al., Self-complementary AAV vectors; advances and applications. Mol Ther. 2008;16(10):1648-1656. doi:10.1038/mt.2008.171.

NCBI Reference Sequence No. NM_025114.3. Jul. 5, 2019. 9 pages.

No et al., Ecdysone-inducible gene expression in mammalian cells and transgenic mice. Proc Natl Acad Sci U S A. Apr. 16, 1996; 93(8): 3346-3351. doi: 10.1073/pnas.93.8.3346.

Plantier et al., A factor VIII minigene comprising the truncated intron I of factor IX highly improves the in vitro production of factor VIII. Thromb Haemost. 2001;86(2):596-603.

Ryan et al., Foot-and-mouth disease virus 2A oligopeptide mediated cleavage of an artificial polyprotein. EMBO J. Feb. 15, 1994; 13(4): 928-933.

Tsang et al., CP110 suppresses primary cilia formation through its interaction with CEP290, a protein deficient in human ciliary disease. Dev Cell. Aug. 2008;15(2):187-97. doi: 10.1016/j.devcel.2008.07.004.

Wang et al., Ligand-inducible and liver-specific target gene expression in transgenic mice. Nat Biotechnol. Mar. 1, 1997;15:239-243. doi: https://doi.org/10.1038/nbt0397-239.

Wang et al., Positive and negative regulation of gene expression in eukaryotic cells with an inducible transcriptional regulator. Gene Therapy. 1997;4:432-441. https://doi.org/10.1038/sj.gt.3300402.

Wright et al., Identification of factors that contribute to recombinant AAV2 particle aggregation and methods to prevent its occurrence during vector purification and formulation. Mol Ther. 2005;12(1):171-178. doi:10.1016/j.ymthe.2005.02.021.

Xiao et al., Rescue of the albino phenotype by introducing a functional tyrosinase minigene into Kunming albino mice. World J Gastroenterol. Jan. 14, 2007; 13(2): 244-249. EPub Jan. 14, 2007. doi: 10.3748/wjg.v13.i2.244.

Zhang et al., Gene Therapy Using a miniCEP290 Fragment Delays Photoreceptor Degeneration in a Mouse Model of Leber Congenital Amaurosis. Hum Gene Ther. Jan. 2018;29(1):42-50. doi: 10.1089/hum.2017.049. Epub Jul. 5, 2017.

EP 18781286.2, Mar. 11, 2021, Extended European Search Report.

International Search Report and Written Opinion for Application No. PCT/US2018/026230, dated Jul. 23, 2018.

International Preliminary Report on Patentability for Application No. PCT/US2018/026230, dated Oct. 17, 2019.

Baye et al., The N-terminal region of centrosomal protein 290 (CEP290) restores vision in a zebrafish model of human blindness. Hum Mol Genet. Apr. 15, 2011;20(8):1467-77. doi: 10.1093/hmg/ddr025. Epub Jan. 21, 2011.

Mookherjee et al., A CEP290 C-Terminal Domain Complements the Mutant CEP290 of Rd16 Mice in Trans and Rescues Retinal Degeneration. Cell Rep. Oct. 16, 2018;25(3):611-623.e6. doi: 10.1016/j.celrep.2018.09.043.

U.S. Appl. No. 17/612,653, filed Nov. 19, 2021, Gao et al..

* cited by examiner

SEQUENCE LISTING

<160> NUMBER OF SEQ ID NOS: 9

<210> SEQ ID NO 1
<211> LENGTH: 2479
<212> TYPE: PRT
<213> ORGANISM: Homo sapiens

<400> SEQUENCE: 1

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
        355                 360                 365

-continued

```
Glu Gln Val Glu Gln Tyr Thr Lys Glu Met Glu Lys Asn Thr Cys Ile
    370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
                420                 425                 430

Asp Ala Arg Glu Lys Asp Lys Glu Leu Val Glu Ala Leu Lys Arg Leu
            435                 440                 445

Lys Asp Tyr Glu Ser Gly Val Tyr Gly Leu Glu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
                500                 505                 510

Thr Met Ile Asp Leu Thr Glu Phe Arg Asn Ser Lys His Leu Lys Gln
            515                 520                 525

Gln Gln Tyr Arg Ala Glu Asn Gln Ile Leu Lys Glu Ile Glu Ser
    530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
    595                 600                 605

Asn Glu Phe Leu Ser Arg Glu Leu Ile Glu Lys Glu Arg Asp Leu Glu
610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
    675                 680                 685

Lys Asn Ala Glu Gly Ile Phe Asp Ala Ser Leu His Leu Lys Ala Gln
690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
    755                 760                 765

Ile Ala Pro Ser Ser Ala Ser Ile Ile Asn Ser Gln Asn Glu Tyr Leu
770                 775                 780

Ile His Leu Leu Gln Glu Leu Glu Asn Lys Glu Lys Lys Leu Lys Asn
```

-continued

```
                785                 790                 795                 800
Leu Glu Asp Ser Leu Glu Asp Tyr Asn Arg Lys Phe Ala Val Ile Arg
                    805                 810                 815
His Gln Gln Ser Leu Leu Tyr Lys Glu Tyr Leu Ser Glu Lys Glu Thr
                    820                 825                 830
Trp Lys Thr Glu Ser Lys Thr Ile Lys Glu Lys Arg Lys Leu Glu
                    835                 840                 845
Asp Gln Val Gln Gln Asp Ala Ile Lys Val Lys Glu Tyr Asn Asn Leu
                    850                 855                 860
Leu Asn Ala Leu Gln Met Asp Ser Asp Glu Met Lys Lys Ile Leu Ala
865                 870                 875                 880
Glu Asn Ser Arg Lys Ile Thr Val Leu Gln Val Asn Glu Lys Ser Leu
                    885                 890                 895
Ile Arg Gln Tyr Thr Thr Leu Val Glu Leu Glu Arg Gln Leu Arg Lys
                    900                 905                 910
Glu Asn Glu Lys Gln Lys Asn Glu Leu Leu Ser Met Glu Ala Glu Val
                    915                 920                 925
Cys Glu Lys Ile Gly Cys Leu Gln Arg Phe Lys Glu Met Ala Ile Phe
930                 935                 940
Lys Ile Ala Ala Leu Gln Lys Val Val Asp Asn Ser Val Ser Leu Ser
945                 950                 955                 960
Glu Leu Glu Leu Ala Asn Lys Gln Tyr Asn Glu Leu Thr Ala Lys Tyr
                    965                 970                 975
Arg Asp Ile Leu Gln Lys Asp Asn Met Leu Val Gln Arg Thr Ser Asn
                    980                 985                 990
Leu Glu His Leu Glu Cys Glu Asn Ile Ser Leu Lys Glu Gln Val Glu
            995                 1000                1005
Ser Ile Asn Lys Glu Leu Glu Ile Thr Lys Glu Lys Leu His Thr
        1010                1015                1020
Ile Glu Gln Ala Trp Glu Gln Glu Thr Lys Leu Gly Asn Glu Ser
        1025                1030                1035
Ser Met Asp Lys Ala Lys Lys Ser Ile Thr Asn Ser Asp Ile Val
        1040                1045                1050
Ser Ile Ser Lys Lys Ile Thr Met Leu Glu Met Lys Glu Leu Asn
        1055                1060                1065
Glu Arg Gln Arg Ala Glu His Cys Gln Lys Met Tyr Glu His Leu
        1070                1075                1080
Arg Thr Ser Leu Lys Gln Met Glu Glu Arg Asn Phe Glu Leu Glu
        1085                1090                1095
Thr Lys Phe Ala Glu Leu Thr Lys Ile Asn Leu Asp Ala Gln Lys
        1100                1105                1110
Val Glu Gln Met Leu Arg Asp Glu Leu Ala Asp Ser Val Ser Lys
        1115                1120                1125
Ala Val Ser Asp Ala Asp Arg Gln Arg Ile Leu Glu Leu Glu Lys
        1130                1135                1140
Asn Glu Met Glu Leu Lys Val Glu Val Ser Lys Leu Arg Glu Ile
        1145                1150                1155
Ser Asp Ile Ala Arg Arg Gln Val Glu Ile Leu Asn Ala Gln Gln
        1160                1165                1170
Gln Ser Arg Asp Lys Glu Val Glu Ser Leu Arg Met Gln Leu Leu
        1175                1180                1185
Asp Tyr Gln Ala Gln Ser Asp Glu Lys Ser Leu Ile Ala Lys Leu
        1190                1195                1200
```

-continued

His Gln His Asn Val Ser Leu Gln Leu Ser Glu Ala Thr Ala Leu
1205                 1210                1215

Gly Lys Leu Glu Ser Ile Thr Ser Lys Leu Gln Lys Met Glu Ala
1220                 1225                1230

Tyr Asn Leu Arg Leu Glu Gln Lys Leu Asp Glu Lys Glu Gln Ala
1235                 1240                1245

Leu Tyr Tyr Ala Arg Leu Glu Gly Arg Asn Arg Ala Lys His Leu
1250                 1255                1260

Arg Gln Thr Ile Gln Ser Leu Arg Arg Gln Phe Ser Gly Ala Leu
1265                 1270                1275

Pro Leu Ala Gln Gln Glu Lys Phe Ser Lys Thr Met Ile Gln Leu
1280                 1285                1290

Gln Asn Asp Lys Leu Lys Ile Met Gln Glu Met Lys Asn Ser Gln
1295                 1300                1305

Gln Glu His Arg Asn Met Glu Asn Lys Thr Leu Glu Met Glu Leu
1310                 1315                1320

Lys Leu Lys Gly Leu Glu Glu Leu Ile Ser Thr Leu Lys Asp Thr
1325                 1330                1335

Lys Gly Ala Gln Lys Val Ile Asn Trp His Met Lys Ile Glu Glu
1340                 1345                1350

Leu Arg Leu Gln Glu Leu Lys Leu Asn Arg Glu Leu Val Lys Asp
1355                 1360                1365

Lys Glu Glu Ile Lys Tyr Leu Asn Asn Ile Ile Ser Glu Tyr Glu
1370                 1375                1380

Arg Thr Ile Ser Ser Leu Glu Glu Ile Val Gln Gln Asn Lys
1385                 1390                1395

Phe His Glu Glu Arg Gln Met Ala Trp Asp Gln Arg Glu Val Asp
1400                 1405                1410

Leu Glu Arg Gln Leu Asp Ile Phe Asp Arg Gln Gln Asn Glu Ile
1415                 1420                1425

Leu Asn Ala Ala Gln Lys Phe Glu Glu Ala Thr Gly Ser Ile Pro
1430                 1435                1440

Asp Pro Ser Leu Pro Leu Pro Asn Gln Leu Glu Ile Ala Leu Arg
1445                 1450                1455

Lys Ile Lys Glu Asn Ile Arg Ile Ile Leu Glu Thr Arg Ala Thr
1460                 1465                1470

Cys Lys Ser Leu Glu Glu Lys Leu Lys Glu Lys Glu Ser Ala Leu
1475                 1480                1485

Arg Leu Ala Glu Gln Asn Ile Leu Ser Arg Asp Lys Val Ile Asn
1490                 1495                1500

Glu Leu Arg Leu Arg Leu Pro Ala Thr Ala Glu Arg Glu Lys Leu
1505                 1510                1515

Ile Ala Glu Leu Gly Arg Lys Glu Met Glu Pro Lys Ser His His
1520                 1525                1530

Thr Leu Lys Ile Ala His Gln Thr Ile Ala Asn Met Gln Ala Arg
1535                 1540                1545

Leu Asn Gln Lys Glu Glu Val Leu Lys Lys Tyr Gln Arg Leu Leu
1550                 1555                1560

Glu Lys Ala Arg Glu Glu Gln Arg Glu Ile Val Lys Lys His Glu
1565                 1570                1575

Glu Asp Leu His Ile Leu His His Arg Leu Glu Leu Gln Ala Asp
1580                 1585                1590

```
Ser Ser Leu Asn Lys Phe Lys Gln Thr Ala Trp Asp Leu Met Lys
1595                1600                1605

Gln Ser Pro Thr Pro Val Pro Thr Asn Lys His Phe Ile Arg Leu
1610                1615                1620

Ala Glu Met Glu Gln Thr Val Ala Glu Gln Asp Asp Ser Leu Ser
1625                1630                1635

Ser Leu Leu Val Lys Leu Lys Lys Val Ser Gln Asp Leu Glu Arg
1640                1645                1650

Gln Arg Glu Ile Thr Glu Leu Lys Val Lys Glu Phe Glu Asn Ile
1655                1660                1665

Lys Leu Gln Leu Gln Glu Asn His Glu Asp Glu Val Lys Lys Val
1670                1675                1680

Lys Ala Glu Val Glu Asp Leu Lys Tyr Leu Leu Asp Gln Ser Gln
1685                1690                1695

Lys Glu Ser Gln Cys Leu Lys Ser Glu Leu Gln Ala Gln Lys Glu
1700                1705                1710

Ala Asn Ser Arg Ala Pro Thr Thr Thr Met Arg Asn Leu Val Glu
1715                1720                1725

Arg Leu Lys Ser Gln Leu Ala Leu Lys Glu Lys Gln Gln Lys Ala
1730                1735                1740

Leu Ser Arg Ala Leu Leu Glu Leu Arg Ala Glu Met Thr Ala Ala
1745                1750                1755

Ala Glu Glu Arg Ile Ile Ser Ala Thr Ser Gln Lys Glu Ala His
1760                1765                1770

Leu Asn Val Gln Gln Ile Val Asp Arg His Thr Arg Glu Leu Lys
1775                1780                1785

Thr Gln Val Glu Asp Leu Asn Glu Asn Leu Leu Lys Leu Lys Glu
1790                1795                1800

Ala Leu Lys Thr Ser Lys Asn Arg Glu Asn Ser Leu Thr Asp Asn
1805                1810                1815

Leu Asn Asp Leu Asn Asn Glu Leu Gln Lys Lys Gln Lys Ala Tyr
1820                1825                1830

Asn Lys Ile Leu Arg Glu Lys Glu Glu Ile Asp Gln Glu Asn Asp
1835                1840                1845

Glu Leu Lys Arg Gln Ile Lys Arg Leu Thr Ser Gly Leu Gln Gly
1850                1855                1860

Lys Pro Leu Thr Asp Asn Lys Gln Ser Leu Ile Glu Glu Leu Gln
1865                1870                1875

Arg Lys Val Lys Lys Leu Glu Asn Gln Leu Glu Gly Lys Val Glu
1880                1885                1890

Glu Val Asp Leu Lys Pro Met Lys Glu Lys Asn Ala Lys Glu Glu
1895                1900                1905

Leu Ile Arg Trp Glu Glu Gly Lys Lys Trp Gln Ala Lys Ile Glu
1910                1915                1920

Gly Ile Arg Asn Lys Leu Lys Glu Lys Glu Gly Glu Val Phe Thr
1925                1930                1935

Leu Thr Lys Gln Leu Asn Thr Leu Lys Asp Leu Phe Ala Lys Ala
1940                1945                1950

Asp Lys Glu Lys Leu Thr Leu Gln Arg Lys Leu Lys Thr Thr Gly
1955                1960                1965

Met Thr Val Asp Gln Val Leu Gly Ile Arg Ala Leu Glu Ser Glu
1970                1975                1980

Lys Glu Leu Glu Glu Leu Lys Lys Arg Asn Leu Asp Leu Glu Asn
```

```
            1985                1990                1995
Asp Ile Leu Tyr Met Arg Ala His Gln Ala Leu Pro Arg Asp Ser
            2000                2005                2010

Val Val Glu Asp Leu His Leu Gln Asn Arg Tyr Leu Gln Glu Lys
            2015                2020                2025

Leu His Ala Leu Glu Lys Gln Phe Ser Lys Asp Thr Tyr Ser Lys
            2030                2035                2040

Pro Ser Ile Ser Gly Ile Glu Ser Asp Asp His Cys Gln Arg Glu
            2045                2050                2055

Gln Glu Leu Gln Lys Glu Asn Leu Lys Leu Ser Ser Glu Asn Ile
            2060                2065                2070

Glu Leu Lys Phe Gln Leu Glu Gln Ala Asn Lys Asp Leu Pro Arg
            2075                2080                2085

Leu Lys Asn Gln Val Arg Asp Leu Lys Glu Met Cys Glu Phe Leu
            2090                2095                2100

Lys Lys Glu Lys Ala Glu Val Gln Arg Lys Leu Gly His Val Arg
            2105                2110                2115

Gly Ser Gly Arg Ser Gly Lys Thr Ile Pro Glu Leu Glu Lys Thr
            2120                2125                2130

Ile Gly Leu Met Lys Lys Val Val Glu Lys Val Gln Arg Glu Asn
            2135                2140                2145

Glu Gln Leu Lys Lys Ala Ser Gly Ile Leu Thr Ser Glu Lys Met
            2150                2155                2160

Ala Asn Ile Glu Gln Glu Asn Glu Lys Leu Lys Ala Glu Leu Glu
            2165                2170                2175

Lys Leu Lys Ala His Leu Gly His Gln Leu Ser Met His Tyr Glu
            2180                2185                2190

Ser Lys Thr Lys Gly Thr Glu Lys Ile Ile Ala Glu Asn Glu Arg
            2195                2200                2205

Leu Arg Lys Glu Leu Lys Lys Glu Thr Asp Ala Ala Glu Lys Leu
            2210                2215                2220

Arg Ile Ala Lys Asn Asn Leu Glu Ile Leu Asn Glu Lys Met Thr
            2225                2230                2235

Val Gln Leu Glu Glu Thr Gly Lys Arg Leu Gln Phe Ala Glu Ser
            2240                2245                2250

Arg Gly Pro Gln Leu Glu Gly Ala Asp Ser Lys Ser Trp Lys Ser
            2255                2260                2265

Ile Val Val Thr Arg Met Tyr Glu Thr Lys Leu Lys Glu Leu Glu
            2270                2275                2280

Thr Asp Ile Ala Lys Lys Asn Gln Ser Ile Thr Asp Leu Lys Gln
            2285                2290                2295

Leu Val Lys Glu Ala Thr Glu Arg Glu Gln Lys Val Asn Lys Tyr
            2300                2305                2310

Asn Glu Asp Leu Glu Gln Gln Ile Lys Ile Leu Lys His Val Pro
            2315                2320                2325

Glu Gly Ala Glu Thr Glu Gln Gly Leu Lys Arg Glu Leu Gln Val
            2330                2335                2340

Leu Arg Leu Ala Asn His Gln Leu Asp Lys Glu Lys Ala Glu Leu
            2345                2350                2355

Ile His Gln Ile Glu Ala Asn Lys Asp Gln Ser Gly Ala Glu Ser
            2360                2365                2370

Thr Ile Pro Asp Ala Asp Gln Leu Lys Glu Lys Ile Lys Asp Leu
            2375                2380                2385
```

```
Glu Thr Gln Leu Lys Met Ser Asp Leu Glu Lys Gln His Leu Lys
    2390            2395                2400

Glu Glu Ile Lys Lys Leu Lys Lys Glu Leu Glu Asn Phe Asp Pro
    2405            2410                2415

Ser Phe Phe Glu Glu Ile Glu Asp Leu Lys Tyr Asn Tyr Lys Glu
    2420            2425                2430

Glu Val Lys Lys Asn Ile Leu Leu Glu Glu Lys Val Lys Lys Leu
    2435            2440                2445

Ser Glu Gln Leu Gly Val Glu Leu Thr Ser Pro Val Ala Ala Ser
    2450            2455                2460

Glu Glu Phe Glu Asp Glu Glu Ser Pro Val Asn Phe Pro Ile
    2465            2470                2475

Tyr

<210> SEQ ID NO 2
<211> LENGTH: 1116
<212> TYPE: PRT
<213> ORGANISM: Artificial Sequence
<220> FEATURE:
<223> OTHER INFORMATION: Synthetic Polypeptide

<400> SEQUENCE: 2

Thr Glu Asn Ile Ser Gln Gly Asp Arg Ile Ser Glu Arg Lys Leu Asp
1               5                   10                  15

Leu Leu Ser Leu Lys Asn Met Ser Glu Ala Gln Ser Lys Asn Glu Phe
            20                  25                  30

Leu Ser Arg Glu Leu Ile Glu Lys Glu Arg Asp Leu Glu Arg Ser Arg
        35                  40                  45

Thr Val Ile Ala Lys Phe Gln Asn Lys Leu Lys Glu Leu Val Glu Glu
    50                  55                  60

Asn Lys Gln Leu Glu Glu Gly Met Lys Glu Ile Leu Gln Ala Ile Lys
65                  70                  75                  80

Glu Met Gln Lys Asp Pro Asp Val Lys Gly Gly Glu Thr Ser Leu Ile
                85                  90                  95

Ile Pro Ser Leu Glu Arg Leu Val Asn Ala Ile Glu Ser Lys Asn Ala
            100                 105                 110

Glu Gly Ile Phe Asp Ala Ser Leu His Leu Lys Ala Gln Val Asp Gln
        115                 120                 125

Leu Thr Gly Arg Asn Glu Glu Leu Arg Gln Glu Leu Arg Glu Ser Arg
    130                 135                 140

Lys Glu Ala Ile Asn Tyr Ser Gln Gln Leu Ala Lys Ala Asn Leu Lys
145                 150                 155                 160

Ile Asp His Leu Glu Lys Glu Thr Ser Leu Leu Arg Gln Ser Glu Gly
                165                 170                 175

Ser Asn Val Val Phe Lys Gly Ile Asp Leu Pro Asp Gly Ile Ala Pro
            180                 185                 190

Ser Ser Ala Ser Ile Ile Asn Ser Gln Asn Glu Tyr Leu Ile His Leu
        195                 200                 205

Leu Gln Glu Leu Glu Asn Lys Glu Lys Lys Leu Lys Asn Leu Glu Asp
    210                 215                 220

Ser Leu Glu Asp Tyr Asn Arg Lys Phe Ala Val Ile Arg His Gln Gln
225                 230                 235                 240

Ser Leu Leu Tyr Lys Glu Tyr Leu Ser Glu Lys Glu Thr Trp Lys Thr
                245                 250                 255
```

```
Glu Ser Lys Thr Ile Lys Glu Glu Lys Arg Lys Leu Glu Asp Gln Val
            260                 265                 270

Gln Gln Asp Ala Ile Lys Val Lys Glu Tyr Asn Asn Leu Leu Asn Ala
        275                 280                 285

Leu Gln Met Asp Ser Asp Glu Met Lys Lys Ile Leu Ala Glu Asn Ser
    290                 295                 300

Arg Lys Ile Thr Val Leu Gln Val Asn Glu Lys Ser Leu Ile Arg Gln
305                 310                 315                 320

Tyr Thr Thr Leu Val Glu Leu Glu Arg Gln Leu Arg Lys Glu Asn Glu
                325                 330                 335

Lys Gln Lys Asn Glu Leu Leu Ser Met Glu Ala Glu Val Cys Glu Lys
            340                 345                 350

Ile Gly Cys Leu Gln Arg Phe Lys Glu Met Ala Ile Phe Lys Ile Ala
        355                 360                 365

Ala Leu Gln Lys Val Val Asp Asn Ser Val Ser Leu Ser Glu Leu Glu
    370                 375                 380

Leu Ala Asn Lys Gln Tyr Asn Glu Leu Thr Ala Lys Tyr Arg Asp Ile
385                 390                 395                 400

Leu Gln Lys Asp Asn Met Leu Val Gln Arg Thr Ser Asn Leu Glu His
                405                 410                 415

Leu Glu Cys Glu Asn Ile Ser Leu Lys Glu Gln Val Glu Ser Ile Asn
            420                 425                 430

Lys Glu Leu Glu Ile Thr Lys Glu Lys Leu His Thr Ile Glu Gln Ala
        435                 440                 445

Trp Glu Gln Glu Thr Lys Leu Gly Asn Glu Ser Ser Met Asp Lys Ala
    450                 455                 460

Lys Lys Ser Ile Thr Asn Ser Asp Ile Val Ser Ile Ser Lys Lys Ile
465                 470                 475                 480

Thr Met Leu Glu Met Lys Glu Leu Asn Glu Arg Gln Arg Ala Glu His
                485                 490                 495

Cys Gln Lys Met Tyr Glu His Leu Arg Thr Ser Leu Lys Gln Met Glu
            500                 505                 510

Glu Arg Asn Phe Glu Leu Glu Thr Lys Phe Ala Glu Leu Thr Lys Ile
        515                 520                 525

Asn Leu Asp Ala Gln Lys Val Glu Gln Met Leu Arg Asp Glu Leu Ala
    530                 535                 540

Asp Ser Val Ser Lys Ala Val Ser Asp Ala Asp Arg Gln Arg Ile Leu
545                 550                 555                 560

Glu Leu Glu Lys Asn Glu Met Glu Leu Lys Val Glu Val Ser Lys Leu
                565                 570                 575

Arg Glu Ile Ser Asp Ile Ala Arg Arg Gln Val Glu Ile Leu Asn Ala
            580                 585                 590

Gln Gln Gln Ser Arg Asp Lys Glu Val Glu Ser Leu Arg Met Gln Leu
        595                 600                 605

Leu Asp Tyr Gln Ala Gln Ser Asp Glu Lys Ser Leu Ile Ala Lys Leu
    610                 615                 620

His Gln His Asn Val Ser Leu Gln Leu Ser Glu Ala Thr Ala Leu Gly
625                 630                 635                 640

Lys Leu Glu Ser Ile Thr Ser Lys Leu Gln Lys Met Glu Ala Tyr Asn
                645                 650                 655

Leu Arg Leu Glu Gln Lys Leu Asp Glu Lys Glu Gln Ala Leu Tyr Tyr
            660                 665                 670

Ala Arg Leu Glu Gly Arg Asn Arg Ala Lys His Leu Arg Gln Thr Ile
```

-continued

```
                675                 680                 685
Gln Ser Leu Arg Arg Gln Phe Ser Gly Ala Leu Pro Leu Ala Gln Gln
            690                 695                 700
Glu Lys Phe Ser Lys Thr Met Ile Gln Leu Gln Asn Asp Lys Leu Lys
705                 710                 715                 720
Ile Met Gln Glu Met Lys Asn Ser Gln Gln Glu His Arg Asn Met Glu
                725                 730                 735
Asn Lys Thr Leu Glu Met Glu Leu Lys Leu Lys Gly Leu Glu Glu Leu
            740                 745                 750
Ile Ser Thr Leu Lys Asp Thr Lys Gly Ala Gln Lys Val Ile Asn Trp
        755                 760                 765
His Met Lys Ile Glu Glu Leu Arg Leu Gln Glu Leu Lys Leu Asn Arg
    770                 775                 780
Glu Leu Val Lys Asp Lys Glu Ile Lys Tyr Leu Asn Asn Ile Ile
785                 790                 795                 800
Ser Glu Tyr Glu Arg Thr Ile Ser Ser Leu Glu Glu Ile Val Gln
                805                 810                 815
Gln Asn Lys Phe His Glu Glu Arg Gln Met Ala Trp Asp Gln Arg Glu
            820                 825                 830
Val Asp Leu Glu Arg Gln Leu Asp Ile Phe Asp Arg Gln Asn Glu
        835                 840                 845
Ile Leu Asn Ala Ala Gln Lys Phe Glu Glu Ala Thr Gly Ser Ile Pro
    850                 855                 860
Asp Pro Ser Leu Pro Leu Pro Asn Gln Leu Glu Ile Ala Leu Arg Lys
865                 870                 875                 880
Ile Lys Glu Asn Ile Arg Ile Leu Glu Thr Arg Ala Thr Cys Lys
                885                 890                 895
Ser Leu Glu Glu Lys Leu Lys Glu Lys Glu Ser Ala Leu Arg Leu Ala
            900                 905                 910
Glu Gln Asn Ile Leu Ser Arg Asp Lys Val Ile Asn Glu Leu Arg Leu
        915                 920                 925
Arg Leu Pro Ala Thr Ala Glu Arg Glu Lys Leu Ile Ala Glu Leu Gly
    930                 935                 940
Arg Lys Glu Met Glu Pro Lys Ser His His Thr Leu Lys Ile Ala His
945                 950                 955                 960
Gln Thr Ile Ala Asn Met Gln Ala Arg Leu Asn Gln Lys Glu Glu Val
                965                 970                 975
Leu Lys Lys Tyr Gln Arg Leu Leu Glu Lys Ala Arg Glu Glu Gln Arg
            980                 985                 990
Glu Ile Val Lys Lys His Glu Glu Asp Leu His Ile Leu His His Arg
        995                 1000                1005
Leu Glu Leu Gln Ala Asp Ser Ser Leu Asn Lys Phe Lys Gln Thr
    1010                1015                1020
Ala Trp Asp Leu Met Lys Gln Ser Pro Thr Pro Val Pro Thr Asn
    1025                1030                1035
Lys His Phe Ile Arg Leu Ala Glu Met Glu Gln Thr Val Ala Glu
    1040                1045                1050
Gln Asp Asp Ser Leu Ser Ser Leu Leu Val Lys Leu Lys Lys Val
    1055                1060                1065
Ser Gln Asp Leu Glu Arg Gln Arg Glu Ile Thr Glu Leu Lys Val
    1070                1075                1080
Lys Glu Phe Glu Asn Ile Lys Leu Gln Leu Gln Glu Asn His Glu
    1085                1090                1095
```

```
Asp Glu  Val Lys Lys Val Lys  Ala Glu Val Glu Asp  Leu Lys Tyr
    1100             1105             1110

Leu Leu Asp
    1115
```

<210> SEQ ID NO 3
<211> LENGTH: 601
<212> TYPE: PRT
<213> ORGANISM: Artificial Sequence
<220> FEATURE:
<223> OTHER INFORMATION: Synthetic Polypeptide

<400> SEQUENCE: 3

```
Thr Glu Asn Ile Ser Gln Gly Asp Arg Ile Ser Glu Arg Lys Leu Asp
1               5                   10                  15

Leu Leu Ser Leu Lys Asn Met Ser Glu Ala Gln Ser Lys Asn Glu Phe
            20                  25                  30

Leu Ser Arg Glu Leu Ile Glu Lys Glu Arg Asp Leu Glu Arg Ser Arg
        35                  40                  45

Thr Val Ile Ala Lys Phe Gln Asn Lys Leu Lys Glu Leu Val Glu Glu
    50                  55                  60

Asn Lys Gln Leu Glu Glu Gly Met Lys Glu Ile Leu Gln Ala Ile Lys
65                  70                  75                  80

Glu Met Gln Lys Asp Pro Asp Val Lys Gly Gly Glu Thr Ser Leu Ile
                85                  90                  95

Ile Pro Ser Leu Glu Arg Leu Val Asn Ala Ile Glu Ser Lys Asn Ala
            100                 105                 110

Glu Gly Ile Phe Asp Ala Ser Leu His Leu Lys Ala Gln Val Asp Gln
        115                 120                 125

Leu Thr Gly Arg Asn Glu Glu Leu Arg Gln Glu Leu Arg Glu Ser Arg
    130                 135                 140

Lys Glu Ala Ile Asn Tyr Ser Gln Gln Leu Ala Lys Ala Asn Leu Lys
145                 150                 155                 160

Ile Asp His Leu Glu Lys Glu Thr Ser Leu Leu Arg Gln Ser Glu Gly
                165                 170                 175

Ser Asn Val Val Phe Lys Gly Ile Asp Leu Pro Asp Gly Ile Ala Pro
            180                 185                 190

Ser Ser Ala Ser Ile Ile Asn Ser Gln Asn Glu Tyr Leu Ile His Leu
        195                 200                 205

Leu Gln Glu Leu Glu Asn Lys Glu Lys Lys Leu Lys Asn Leu Glu Asp
    210                 215                 220

Ser Leu Glu Asp Tyr Asn Arg Lys Phe Ala Val Ile Arg His Gln Gln
225                 230                 235                 240

Ser Leu Leu Tyr Lys Glu Tyr Leu Ser Glu Lys Glu Thr Trp Lys Thr
                245                 250                 255

Glu Ser Lys Thr Ile Lys Glu Leu Lys Arg Lys Leu Glu Asp Gln Val
            260                 265                 270

Gln Gln Asp Ala Ile Lys Val Lys Glu Tyr Asn Asn Leu Leu Asn Ala
        275                 280                 285

Leu Gln Met Asp Ser Asp Glu Met Lys Lys Ile Leu Ala Glu Asn Ser
    290                 295                 300

Arg Lys Ile Thr Val Leu Gln Val Asn Glu Lys Ser Leu Ile Arg Gln
305                 310                 315                 320

Tyr Thr Thr Leu Val Glu Leu Glu Arg Gln Leu Arg Lys Glu Asn Glu
                325                 330                 335
```

```
Lys Gln Lys Asn Glu Leu Leu Ser Met Glu Ala Glu Val Cys Glu Lys
            340                 345                 350

Ile Gly Cys Leu Gln Arg Phe Lys Glu Met Ala Ile Phe Lys Ile Ala
            355                 360                 365

Ala Leu Gln Lys Val Val Asp Asn Ser Val Ser Leu Ser Glu Leu Glu
        370                 375                 380

Leu Ala Asn Lys Gln Tyr Asn Glu Leu Thr Ala Lys Tyr Arg Asp Ile
385                 390                 395                 400

Leu Gln Lys Asp Asn Met Leu Val Gln Arg Thr Ser Asn Leu Glu His
                405                 410                 415

Leu Glu Cys Glu Asn Ile Ser Leu Lys Glu Gln Val Glu Ser Ile Asn
            420                 425                 430

Lys Glu Leu Glu Ile Thr Lys Glu Lys Leu His Thr Ile Glu Gln Ala
        435                 440                 445

Trp Glu Gln Glu Thr Lys Leu Gly Asn Glu Ser Ser Met Asp Lys Ala
    450                 455                 460

Lys Lys Ser Ile Thr Asn Ser Asp Ile Val Ser Ile Ser Lys Lys Ile
465                 470                 475                 480

Thr Met Leu Glu Met Lys Glu Leu Asn Glu Arg Gln Arg Ala Glu His
                485                 490                 495

Cys Gln Lys Met Tyr Glu His Leu Arg Thr Ser Leu Lys Gln Met Glu
            500                 505                 510

Glu Arg Asn Phe Glu Leu Glu Thr Lys Phe Ala Glu Leu Thr Lys Ile
        515                 520                 525

Asn Leu Asp Ala Gln Lys Val Glu Gln Met Leu Arg Asp Glu Leu Ala
    530                 535                 540

Asp Ser Val Ser Lys Ala Val Ser Asp Ala Asp Arg Gln Arg Ile Leu
545                 550                 555                 560

Glu Leu Glu Lys Asn Glu Met Glu Leu Lys Val Glu Val Ser Lys Leu
                565                 570                 575

Arg Glu Ile Ser Asp Ile Ala Arg Arg Gln Val Glu Ile Leu Asn Ala
            580                 585                 590

Gln Gln Gln Ser Arg Asp Lys Glu Val
            595                 600

<210> SEQ ID NO 4
<211> LENGTH: 515
<212> TYPE: PRT
<213> ORGANISM: Artificial Sequence
<220> FEATURE:
<223> OTHER INFORMATION: Synthetic Polypeptide

<400> SEQUENCE: 4

Glu Ser Leu Arg Met Gln Leu Leu Asp Tyr Gln Ala Gln Ser Asp Glu
1               5                   10                  15

Lys Ser Leu Ile Ala Lys Leu His Gln His Asn Val Ser Leu Gln Leu
            20                  25                  30

Ser Glu Ala Thr Ala Leu Gly Lys Leu Glu Ser Ile Thr Ser Lys Leu
        35                  40                  45

Gln Lys Met Glu Ala Tyr Asn Leu Arg Leu Glu Gln Lys Leu Asp Glu
    50                  55                  60

Lys Glu Gln Ala Leu Tyr Tyr Ala Arg Leu Glu Gly Arg Asn Arg Ala
65                  70                  75                  80

Lys His Leu Arg Gln Thr Ile Gln Ser Leu Arg Arg Gln Phe Ser Gly
                85                  90                  95
```

```
Ala Leu Pro Leu Ala Gln Gln Glu Lys Phe Ser Lys Thr Met Ile Gln
            100                 105                 110

Leu Gln Asn Asp Lys Leu Lys Ile Met Gln Glu Met Lys Asn Ser Gln
        115                 120                 125

Gln Glu His Arg Asn Met Glu Asn Lys Thr Leu Glu Met Glu Leu Lys
    130                 135                 140

Leu Lys Gly Leu Glu Glu Leu Ile Ser Thr Leu Lys Asp Thr Lys Gly
145                 150                 155                 160

Ala Gln Lys Val Ile Asn Trp His Met Lys Ile Glu Leu Arg Leu
            165                 170                 175

Gln Glu Leu Lys Leu Asn Arg Glu Leu Val Lys Asp Lys Glu Ile
        180                 185                 190

Lys Tyr Leu Asn Asn Ile Ile Ser Glu Tyr Glu Arg Thr Ile Ser Ser
    195                 200                 205

Leu Glu Glu Glu Ile Val Gln Gln Asn Lys Phe His Glu Arg Gln
    210                 215                 220

Met Ala Trp Asp Gln Arg Glu Val Asp Leu Glu Arg Gln Leu Asp Ile
225                 230                 235                 240

Phe Asp Arg Gln Gln Asn Glu Ile Leu Asn Ala Ala Gln Lys Phe Glu
            245                 250                 255

Glu Ala Thr Gly Ser Ile Pro Asp Pro Ser Leu Pro Leu Pro Asn Gln
            260                 265                 270

Leu Glu Ile Ala Leu Arg Lys Ile Lys Glu Asn Ile Arg Ile Ile Leu
        275                 280                 285

Glu Thr Arg Ala Thr Cys Lys Ser Leu Glu Glu Lys Leu Lys Glu Lys
        290                 295                 300

Glu Ser Ala Leu Arg Leu Ala Glu Gln Asn Ile Leu Ser Arg Asp Lys
305                 310                 315                 320

Val Ile Asn Glu Leu Arg Leu Arg Leu Pro Ala Thr Ala Glu Arg Glu
            325                 330                 335

Lys Leu Ile Ala Glu Leu Gly Arg Lys Glu Met Glu Pro Lys Ser His
            340                 345                 350

His Thr Leu Lys Ile Ala His Gln Thr Ile Ala Asn Met Gln Ala Arg
        355                 360                 365

Leu Asn Gln Lys Glu Glu Val Leu Lys Lys Tyr Gln Arg Leu Leu Glu
    370                 375                 380

Lys Ala Arg Glu Glu Gln Arg Glu Ile Val Lys Lys His Glu Glu Asp
385                 390                 395                 400

Leu His Ile Leu His His Arg Leu Glu Leu Gln Ala Asp Ser Ser Leu
            405                 410                 415

Asn Lys Phe Lys Gln Thr Ala Trp Asp Leu Met Lys Gln Ser Pro Thr
            420                 425                 430

Pro Val Pro Thr Asn Lys His Phe Ile Arg Leu Ala Glu Met Glu Gln
        435                 440                 445

Thr Val Ala Glu Gln Asp Asp Ser Leu Ser Ser Leu Leu Val Lys Leu
    450                 455                 460

Lys Lys Val Ser Gln Asp Leu Glu Arg Gln Arg Glu Ile Thr Glu Leu
465                 470                 475                 480

Lys Val Lys Glu Phe Glu Asn Ile Lys Leu Gln Leu Gln Glu Asn His
            485                 490                 495

Glu Asp Glu Val Lys Lys Val Lys Ala Glu Val Glu Asp Leu Lys Tyr
            500                 505                 510
```

Leu Leu Asp
    515

<210> SEQ ID NO 5
<211> LENGTH: 3606
<212> TYPE: DNA
<213> ORGANISM: Artificial Sequence
<220> FEATURE:
<223> OTHER INFORMATION: Synthetic Polynucleotide

<400> SEQUENCE: 5

| | | | | | |
|---|---|---|---|---|---|
| actgaaaaca | tttctcaagg | agatagaata | agtgaaagaa | aattggattt | attgagcctc | 60 |
| aaaaatatga | gtgaagcaca | atcaaagaat | gaatttcttt | caagagaact | aattgaaaaa | 120 |
| gaaagagatt | tagaaaggag | taggacagtg | atagccaaat | ttcagaataa | attaaaagaa | 180 |
| ttagttgaag | aaaataagca | acttgaagaa | ggtatgaaag | aaatattgca | agcaattaag | 240 |
| gaaatgcaga | aagatcctga | tgttaaagga | ggagaaacat | ctctaattat | ccctagcctt | 300 |
| gaaagactag | ttaatgctat | agaatcaaag | aatgcagaag | gaatctttga | tgcgagtctg | 360 |
| catttgaaag | cccaagttga | tcagcttacc | ggaagaaatg | aagaattaag | acaggagctc | 420 |
| agggaatctc | ggaagagggc | tataaattat | tcacagcagt | tggcaaaagc | taatttaaag | 480 |
| atagaccatc | ttgaaaaaga | aactagtctt | ttacgacaat | cagaaggatc | gaatgttgtt | 540 |
| tttaaaggaa | ttgacttacc | tgatgggata | gcaccatcta | gtgccagtat | cattaattct | 600 |
| cagaatgaat | atttaataca | tttgttacag | gaactagaaa | ataagaaaa | aaagttaaag | 660 |
| aatttagaag | attctcttga | agattacaac | agaaaatttg | ctgtaattcg | tcatcaacaa | 720 |
| agtttgttgt | ataaagaata | cctaagtgaa | aaggagacct | ggaaaacaga | atctaaaaca | 780 |
| ataaaagagg | aaaagagaaa | acttgaggat | caagtccaac | aagatgctat | aaaagtaaaa | 840 |
| gaatataata | atttgctcaa | tgctcttcag | atggattcgg | atgaaatgaa | aaaaatactt | 900 |
| gcagaaaata | gtaggaaaat | tactgttttg | caagtgaatg | aaaaatcact | tataaggcaa | 960 |
| tatacaaacct | tagtagaatt | ggagcgacaa | cttagaaaag | aaaatgagaa | gcaaaagaat | 1020 |
| gaattgttgt | caatggaggc | tgaagtttgt | gaaaaaattg | ggtgtttgca | aagatttaag | 1080 |
| gaaatggcca | ttttcaagat | tgcagctctc | caaaaagttg | tagataatag | tgtttctttg | 1140 |
| tctgaactag | aactggctaa | taaacagtac | aatgaactga | ctgctaagta | cagggacatc | 1200 |
| ttgcaaaaag | ataatatgct | tgttcaaaga | caagtaact | tggaacacct | ggagtgtgaa | 1260 |
| aacatctcct | aaaagaaca | agtggagtct | ataaataaag | aactggagat | taccaaggaa | 1320 |
| aaacttcaca | ctattgaaca | agcctgggaa | caggaaacta | aattaggtaa | tgaatctagc | 1380 |
| atggataagg | caaagaaatc | aataaccaac | agtgacattg | tttccatttc | aaaaaaaata | 1440 |
| actatgctgg | aaatgaagga | attaaatgaa | aggcagcggg | ctgaacattg | tcaaaaaatg | 1500 |
| tatgaacact | tacggacttc | gttaaagcaa | atggaggaac | gtaattttga | attggaaacc | 1560 |
| aaatttgctg | agcttaccaa | aatcaatttg | gatgcacaga | aggtggaaca | gatgttaaga | 1620 |
| gatgaattag | ctgatagtgt | gagcaaggca | gtaagtgatg | ctgataggca | acggattcta | 1680 |
| gaattagaga | agaatgaaat | ggaactaaaa | gttgaagtgt | caaaactgag | agagatttct | 1740 |
| gatattgcca | gaagacaagt | tgaaattttg | aatgcacaac | aacaatctag | ggacaaggaa | 1800 |
| gtaactgaaa | acatttctca | aggagataga | ataagtgaaa | gaaaattgga | tttattgagc | 1860 |
| ctcaaaaata | tgagtgaagc | acaatcaaag | aatgaatttc | tttcaagaga | actaattgaa | 1920 |
| aaagaaagag | atttagaaag | gagtaggaca | gtgatagcca | aatttcagaa | taaattaaaa | 1980 |

```
gaattagttg aagaaaataa gcaacttgaa gaaggtatga agaaatatt gcaagcaatt      2040 aaggaaatgc agaagatcc tgatgttaaa ggaggagaaa catctctaat tatccctagc      2100
cttgaaagac tagttaatgc tatagaatca agaatgcag aaggaatctt tgatgcgagt      2160
ctgcatttga agcccaagt tgatcagctt accggaagaa atgaagaatt aagacaggag      2220
ctcagggaat ctcggaaaga ggctataaat tattcacagc agttggcaaa agctaattta     2280
aagatagacc atcttgaaaa agaaactagt cttttacgac aatcagaagg atcgaatgtt     2340
gtttttaaag gaattgactt acctgatggg atagcaccat ctagtgccag tatcattaat     2400
tctcagaatg aatatttaat acatttgtta caggaactag aaaataaaga aaaaagtta     2460 aagaatttag aagattctct tgaagattac aacagaaaat ttgctgtaat tcgtcatcaa     2520
caaagtttgt tgtataaaga atacctaagt gaaaaggaga cctggaaaac agaatctaaa    2580
acaataaaag aggaaaagag aaaacttgag gatcaagtcc aacaagatgc tataaaagta    2640
aaagaatata ataatttgct caatgctctt cagatggatt cggatgaaat gaaaaaaata    2700
cttgcagaaa atagtaggaa aattactgtt ttgcaagtga atgaaaaatc acttataagg    2760
caatatacaa ccttagtaga attggagcga caacttagaa aagaaaatga gaagcaaaag    2820
aatgaattgt tgtcaatgga ggctgaagtt tgtgaaaaaa ttgggtgttt gcaaagattt    2880
aaggaaatgg ccattttcaa gattgcagct ctccaaaaag ttgtagataa tagtgtttct    2940
ttgtctgaac tagaactggc taataaacag tacaatgaac tgactgctaa gtacagggac    3000
atcttgcaaa aagataatat gcttgttcaa agaacaagta acttggaaca cctggagtgt    3060
gaaaacatct ccttaaaaga acaagtggag tctataaata aagaactgga gattaccaag    3120
gaaaaacttc acactattga acaagcctgg gaacaggaaa ctaaattagg taatgaatct    3180
agcatggata aggcaaagaa atcaataacc aacagtgaca ttgtttccat ttcaaaaaaa    3240
ataactatgc tggaaatgaa ggaattaaat gaaaggcagc gggctgaaca ttgtcaaaaa    3300
atgtatgaac acttacggac ttcgttaaag caaatggagg aacgtaattt tgaattggaa    3360
accaaatttg ctgagcttac caaaatcaat ttggatgcac agaaggtgga acagatgtta    3420
agagatgaat tagctgatag tgtgagcaag gcagtaagtg atgctgatag caacggatt    3480 ctagaattag agaagaatga aatggaacta aaagttgaag tgtcaaaact gagagagatt    3540
tctgatattg ccagaagaca agttgaaatt tgaatgcac aacaacaatc tagggacaag    3600
gaagta                                                               3606

<210> SEQ ID NO 6
<211> LENGTH: 1803
<212> TYPE: DNA
<213> ORGANISM: Artificial Sequence
<220> FEATURE:
<223> OTHER INFORMATION: Synthetic Polynucleotide

<400> SEQUENCE: 6
actgaaaaca tttctcaagg agatagaata agtgaaagaa aattggattt attgagcctc       60
aaaaatatga gtgaagcaca atcaaagaat gaatttcttt caagagaact aattgaaaaa      120
gaaagagatt tagaaaggag taggacagtg atagccaaat ttcagaataa attaaaagaa      180
ttagttgaag aaaataagca acttgaagaa ggtatgaaag aaatattgca agcaattaag      240
gaaatgcaga agatcctga tgttaaagga gagaaacat ctctaattat ccctagcctt       300
gaaagactag ttaatgctat agaatcaag aatgcagaag aatcttga tgcgagtctg       360 catttgaaag cccaagttga tcagcttacc ggaagaaatg aagaattaag acaggagctc      420
```

```
agggaatctc ggaaagaggc tataaattat tcacagcagt tggcaaaagc taatttaaag      480
atagaccatc ttgaaaaaga aactagtctt ttacgacaat cagaaggatc gaatgttgtt      540
tttaaaggaa ttgacttacc tgatgggata gcaccatcta gtgccagtat cattaattct      600
cagaatgaat atttaataca tttgttacag aactagaaaa ataaagaaaa aaagttaaag      660
aatttagaag attctcttga agattacaac agaaatttg ctgtaattcg tcatcaacaa       720
agtttgttgt ataagaata cctaagtgaa aaggagacct ggaaaacaga atctaaaaca       780
ataaaagagg aaaagagaaa acttgaggat caagtccaac aagatgctat aaaagtaaaa      840
gaatataata atttgctcaa tgctcttcag atggattcgg atgaaatgaa aaaaatactt      900
gcagaaaata gtaggaaaat tactgttttg caagtgaatg aaaaatcact tataaggcaa      960 tatcaacct tagtagaatt ggagcgacaa cttagaaaag aaaatgagaa gcaaaagaat       1020
gaattgttgt caatggaggc tgaagtttgt gaaaaaattg ggtgtttgca agatttaag      1080 gaaatggcca ttttcaagat tgcagctctc caaaagttg tagataatag tgtttctttg       1140
tctgaactag aactggctaa taaacagtac aatgaactga ctgctaagta cagggacatc      1200
ttgcaaaaag ataatatgct tgttcaaaga acaagtaact tggaacaccct ggagtgtgaa     1260 aacatctcct taaaagaaca agtggagtct ataaataaag aactggagat taccaaggaa     1320
aaacttcaca ctattgaaca agcctgggaa caggaaacta aattaggtaa tgaatctagc     1380
atggataagg caaagaaatc aataaccaac agtgacattg tttccatttc aaaaaaaata    1440
actatgctgg aaatgaagga attaaatgaa aggcagcggg ctgaacattg tcaaaaaatg     1500
tatgaacact tacggacttc gttaaagcaa atggaggaac gtaattttga attggaaacc    1560 aaattgctg agcttaccaa aatcaattg gatgcacaga aggtggaaca gatgttaaga      1620
gatgaattag ctgatagtgt gagcaaggca gtaagtgatg ctgataggca acggattcta     1680
gaattagaga agaatgaaat ggaactaaaa gttgaagtgt caaaactgag agagatttct     1740
gatattgcca aagacaagt tgaaattttg aatgcacaac aacaatctag ggacaaggaa     1800
gta                                                                    1803

<210> SEQ ID NO 7
<211> LENGTH: 1545
<212> TYPE: DNA
<213> ORGANISM: Artificial Sequence
<220> FEATURE:
<223> OTHER INFORMATION: Synthetic Polynucleotide

<400> SEQUENCE: 7
gagtccctca gaatgcaact gctagactat caggcacagt ctgatgaaaa gtcgctcatt       60
gccaagttgc accaacataa tgtctctctt caactgagtg aggctactgc tcttggtaag      120
ttggagtcaa ttacatctaa actgcagaag atggaggcct acaacttgcg cttagagcag      180
aaacttgatg aaaagaaca ggctctctat tatgctcgtt tggagggaag aaacagagca      240
aaacatctgc gccaaacaat tcagtctcta cgacgacagt ttagtggagc tttacccttg      300
gcacaacagg aaaagttctc caaaacaatg attcaactac aaaatgacaa acttaagata      360
atgcaagaaa tgaaaaattc tcaacaagaa catagaaata tggagaacaa acattggag      420 atggaattaa aattaaaggg cctggaagag ttaataagca cttttaaagga taccaaagga     480 gcccaaaagg taatcaactg gcatatgaaa atagaagaac ttcgtcttca agaacttaaa     540
ctaaatcggg aattagtcaa ggataaagaa gaaataaaat atttgaataa cataatttct     600
```

```
gaatatgaac gtacaatcag cagtcttgaa aagaaattg tgcaacagaa caagtttcat      660
gaagaaagac aaatggcctg ggatcaaaga gaagttgacc tggaacgcca actagacatt      720
tttgaccgtc agcaaaatga aatactaaat gcggcacaaa agtttgaaga agctacagga      780
tcaatccctg accctagttt gccccttcca aatcaacttg agatcgctct aaggaaaatt      840
aaggagaaca ttcgaataat tctagaaaca cgggcaactt gcaaatcact agaagagaaa      900
ctaaaagaga aagaatctgc tttaaggtta gcagaacaaa atatactgtc aagagacaaa      960
gtaatcaatg aactgaggct tcgattgcct gccactgcag aaagagaaaa gctcatagct     1020
gagctaggca gaaagagat ggaaccaaaa tctcaccaca cattgaaaat tgctcatcaa      1080
accattgcaa acatgcaagc aaggttaaat caaaagaag aagtattaaa gaagtatcaa      1140
cgtcttctag aaaagccag agaggagcaa agagaaattg tgaagaaaca tgaggaagac     1200
cttcatattc ttcatcacag attagaacta caggctgata gttcactaaa taaattcaaa     1260
caaacggctt gggatttaat gaaacagtct cccactccag ttcctaccaa caagcatttt     1320
attcgtctgg ctgagatgga acagacagta gcagaacaag atgactctct ttcctcactc     1380
ttggtcaaac taagaaagt atcacaagat ttggagagac aaagagaaat cactgaatta     1440
aaagtaaaag aatttgaaaa tatcaaatta cagcttcaag aaaaccatga agatgaagtg     1500
aaaaaagtaa aagcggaagt agaggattta agtatcttc tggac                     1545

<210> SEQ ID NO 8
<211> LENGTH: 7972
<212> TYPE: DNA
<213> ORGANISM: Homo sapiens

<400> SEQUENCE: 8
atttgaagtc ctcgttccac gccttctcat catcctgaac accgagctct gggactccgg       60
cggagaatct aaacgtaaag catcacccac ggtcgtgaac tgtaggctct cctggcatcc      120
gggatcttat tctggccttg gcggagttgg ggatggtgtc gcctagcagc cgctgccgct      180
ttggcttgct cgggaccatt tggctggacc cagagtccgc gtggaaccgc gatagggatc      240
tgtcagggcc cgcggccggg tccagcttgg tggttgcggt agtgagaggc ctccgctggt      300
tgccaggctt ggtctagagg tggagcacag tgaaagaatt caagatgcca cctaatataa      360
actggaaaga ataatgaaa gttgacccag atgacctgcc ccgtcaagaa gaactggcag      420
ataatttatt gatttcctta tccaaggtgg aagtaaatga gctaaaaagt gaaaagcaag      480
aaaatgtgat acaccttttc agaattactc agtcactaat gaagatgaaa gctcaagaag      540
tggagctggc tttggaagaa gtagaaaaag ctggagaaga acaagcaaaa tttgaaaatc      600
aattaaaaac taaagtaatg aaactggaaa atgaactgga gatggctcag cagtctgcag      660
gtggacgaga tactcggttt ttacgtaatg aaatttgcca acttgaaaaa caattagaac      720
aaaaagatag agaattggag gacatggaaa aggagttgga gaaagagaag aaagttaatg      780
agcaattggc tcttcgaaat gaggaggcag aaaatgaaaa cagcaaatta agaagagaga      840
acaaacgtct aaagaaaaag aatgaacaac tttgtcagga tattattgac taccagaaac      900
aaatagattc acagaaagaa acactttat caagaagagg ggaagacagt gactaccgat      960
cacagttgtc taaaaaaaac tatgagctta tccaatatct tgatgaaatt cagactttaa     1020
cagaagctaa tgagaaaatt gaagttcaga atcaagaaat gagaaaaaat ttagaagagt     1080
ctgtacagga aatggagaag atgactgatg aatataatag aatgaaagct attgtgcatc     1140
agacagataa tgtaatagat cagttaaaaa aagaaaacga tcattatcaa cttcaagtgc     1200
```

```
aggagcttac agatcttctg aaatcaaaaa atgaagaaga tgatccaatt atggtagctg    1260
tcaatgcaaa agtagaagaa tggaagctaa ttttgtcttc taaagatgat gaaattattg    1320
agtatcagca aatgttacat aacctaaggg agaaacttaa gaatgctcag cttgatgctg    1380
ataaaagtaa tgttatggct ctacagcagg gtatacagga acgagacagt caaattaaga    1440
tgctcaccga acaagtagaa caatatacaa agaaatgga aagaatact tgtattattg      1500 aagatttgaa aaatgagctc caaagaaaca aaggtgcttc aacccttct caacagactc     1560 atatgaaaat tcagtcaacg ttagacattt taaaagagaa aactaaagag gctgagagaa    1620
cagctgaact ggctgaggct gatgctaggg aaaaggataa agaattagtt gaggctctga    1680
agaggttaaa agattatgaa tcgggagtat atggtttaga agatgctgtc gttgaaataa    1740
agaattgtaa aaaccaaatt aaaataagag atcgagagat tgaaatatta acaaaggaaa    1800
tcaataaact tgaattgaag atcagtgatt tccttgatga aaatgaggca cttagagagc    1860
gtgtgggcct tgaaccaaag acaatgattg atttaactga atttagaaat agcaaacact    1920
taaaacagca gcagtacaga gctgaaaacc agattctttt gaaagagatt gaaagtctag    1980
aggaagaacg acttgatctg aaaaaaaaaa ttcgtcaaat ggctcaagaa agaggaaaaa    2040
gaagtgcaac ttcaggatta accactgagg acctgaacct aactgaaaac atttctcaag    2100
gagatagaat aagtgaaaga aaattggatt tattgagcct caaaaatatg agtgaagcac    2160
aatcaaagaa tgaatttctt tcaagagaac taattgaaaa agaaagagat ttagaaagga    2220
gtaggacagt gatagccaaa tttcagaata aattaaaaga attagttgaa gaaaataagc    2280
aacttgaaga aggtatgaaa gaaatattgc aagcaattaa ggaaatgcag aaagatcctg    2340
atgttaaagg aggagaaaca tctctaatta tccctagcct tgaaagacta gttaatgcta    2400
tagaatcaaa gaatgcagaa ggaatctttg atgcgagtct gcatttgaaa gcccaagttg    2460
atcagcttac cggaagaaat gaagaattaa gacaggagct cagggaatct cggaaagagg    2520
ctataaatta ttcacagcag ttggcaaaag ctaatttaaa gatagaccat cttgaaaaag    2580
aaactagtct tttacgacaa tcagaaggat cgaatgttgt ttttaaagga attgacttac    2640
ctgatgggat agcaccatct agtgccagta tcattaattc tcagaatgaa tatttaatac    2700
atttgttaca ggaactagaa aataaagaaa aaagttaaaa gaatttagaa gattctcttg    2760
aagattacaa cagaaaattt gctgtaattc gtcatcaaca aagtttgttg tataaagaat    2820
acctaagtga aaaggagacc tggaaaacag aatctaaaac aataaaagag gaaaagagaa    2880
aacttgagga tcaagtccaa caagatgcta taaaagtaaa agaatataat aatttgctca    2940
atgctcttca gatggattcg gatgaaatga aaaaaatact tgcagaaaat agtaggaaaa    3000 ttactgttt gcaagtgaat gaaaaatcac ttataaggca atatacaacc ttagtagaat     3060
tggagcgaca acttagaaaa gaaaatgaga agcaaaagaa tgaattgttg tcaatggagg    3120
ctgaagtttg tgaaaaaatt gggtgtttgc aaagatttaa ggaaatggcc attttcaaga    3180
ttgcagctct ccaaaaagtt gtagataata gtgtttcttt gtctgaacta gaactggcta    3240
ataaacagta caatgaactg actgctaagt acagggacat cttgcaaaaa gataatatgc    3300
ttgttcaaag aacaagtaac ttggaacacc tggagtgtga aacatctcc ttaaaagaac     3360 aagtggagtc tataaataaa gaactggaga ttaccaagga aaaacttcac actattgaac    3420
aagcctggga acaggaaact aaattaggta atgaatctag catggataag gcaaagaaat    3480
caataaccaa cagtgacatt gtttccattt caaaaaaaat aactatgctg gaaatgaagg    3540
```

```
aattaaatga aaggcagcgg gctgaacatt gtcaaaaaat gtatgaacac ttacggactt      3600
cgttaaagca aatggaggaa cgtaattttg aattggaaac caaatttgct gagcttacca      3660
aaatcaattt ggatgcacag aaggtggaac agatgttaag agatgaatta gctgatagtg      3720
tgagcaaggc agtaagtgat gctgataggc aacggattct agaattagag aagaatgaaa      3780
tggaactaaa agttgaagtg tcaaaactga gagagatttc tgatattgcc agaagacaag      3840
ttgaaatttt gaatgcacaa caacaatcta gggacaagga agtagagtcc ctcagaatgc      3900
aactgctaga ctatcaggca cagtctgatg aaaagtcgct cattgccaag ttgcaccaac      3960
ataatgtctc tcttcaactg agtgaggcta ctgctcttgg taagttggag tcaattacat      4020
ctaaactgca gaagatggag gcctacaact tgcgcttaga gcagaaactt gatgaaaaag      4080
aacaggctct ctattatgct cgtttggagg gaagaaacag agcaaaacat ctgcgccaaa      4140
caattcagtc tctacgacga cagtttagtg gagctttacc cttggcacaa caggaaaagt      4200
tctccaaaac aatgattcaa ctacaaaatg acaaacttaa gataatgcaa gaaatgaaaa      4260
attctcaaca agaacataga aatatggaga acaaacatt ggagatggaa ttaaaattaa       4320
agggcctgga agagttaata agcactttaa aggataccaa aggagcccaa aaggtaatca      4380
actggcatat gaaaatagaa gaacttcgtc ttcaagaact taaactaaat cgggaattag      4440
tcaaggataa agaagaaata aaatatttga ataacataat ttctgaatat gaacgtacaa      4500
tcagcagtct tgaagaagaa attgtgcaac agaacaagtt tcatgaagaa agacaaatgg      4560
cctgggatca aagagaagtt gacctggaac gccaactaga cattttttgac cgtcagcaaa      4620 atgaaatact aaatgcggca caaaagtttg aagaagctac aggatcaatc cctgaccctaa      4680 gtttgcccct tccaaatcaa cttgagatcg ctctaaggaa aattaaggag aacattcgaa      4740
taattctaga aacacgggca acttgcaaat cactagaaga gaaactaaaa gagaaagaat      4800
ctgctttaag gttagcagaa caaaatatac tgtcaagaga caagtaatc aatgaactga       4860 ggcttcgatt gcctgccact gcagaaagag aaaagctcat agctgagcta ggcagaaaag      4920
agatggaacc aaaatctcac cacacattga aaattgctca tcaaaccatt gcaaacatgc      4980
aagcaaggtt aaatcaaaaa gaagaagtat taaagaagta tcaacgtctt ctagaaaaag      5040
ccagagagga gcaaagagaa attgtgaaga acatgaggaa agaccttcat attcttcatc      5100
acagattaga actacaggct gatagttcac taaataaatt caaacaaacg cttgggatt      5160 taatgaaaca gtctcccact ccagttccta ccaacaagca ttttattcgt ctggctgaga      5220
tggaacagac agtagcagaa caagatgact ctctttcctc actcttggtc aaactaaaga      5280
aagtatcaca agatttggag agacaaagag aaatcactga attaaaagta aaagaatttg      5340
aaaatatcaa attacagctt caagaaaacc atgaagatga agtgaaaaaa gtaaagcgg       5400 aagtagagga tttaaagtat cttctggacc agtcacaaaa ggagtcacag tgtttaaaat      5460
ctgaacttca ggctcaaaaa gaagcaaatt caagagctcc aacaactaca atgagaaatc      5520
tagtagaacg gctaaagagc caattagcct tgaaggagaa acaacagaaa gcacttagtc      5580
gggcactttt agaactccgg gcagaaatga cagcagctgc tgaagaacgt attatttctg      5640
caacttctca aaaagaggcc catctcaatg ttcaacaaat cgttgatcga catactagag      5700
agctaaagac acaagttgaa gatttaaatg aaaatctttt aaaattgaaa gaagcactta      5760
aaacaagtaa aaacagagaa aactcactaa ctgataattt gaatgactta aataatgaac      5820
tgcaaaagaa acaaaaagcc tataataaaa tacttagaga gaaagaggaa attgatcaag      5880
agaatgatga actgaaaagg caaattaaaa gactaaccag tggattacag ggcaaacccc      5940
```

```
tgacagataa taaacaaagt ctaattgaag aactccaaag gaaagttaaa aaactagaga    6000
accaattaga gggaaaggtg gaggaagtag acctaaaacc tatgaaagaa aagaatgcta    6060
aagaagaatt aattaggtgg gaagaaggta aaaagtggca agccaaaata gaaggaattc    6120
gaaacaagtt aaaagagaaa gaggggggaag tctttacttt aacaaagcag ttgaatactt    6180
tgaaggatct ttttgccaaa gccgataaag agaaacttac tttgcagagg aaactaaaaa    6240
caactggcat gactgttgat caggttttgg gaatacgagc tttggagtca gaaaagaat    6300 tggaagaatt aaaaaagaga atcttgact tagaaaatga tatattgtat atgagggccc    6360
accaagctct tcctcgagat tctgttgtag aagatttaca tttacaaaat agatacctcc    6420
aagaaaaact tcatgcttta gaaaacagt tttcaaagga tacatattct aagccttcaa    6480
tttcaggaat agagtcagat gatcattgtc agagagaaca ggagcttcag aaggaaaact    6540
tgaagttgtc atctgaaaat attgaactga aatttcagct tgaacaagca aataaagatt    6600
tgccaagatt aaagaatcaa gtcagagatt tgaaggaaat gtgtgaattt cttaagaaag    6660
aaaaagcaga agttcagcgg aaacttggcc atgttagagg gtctggtaga agtggaaaga    6720
caatcccaga actggaaaaa accattggtt taatgaaaaa agtagttgaa aaagtccaga    6780
gagaaaatga acagttgaaa aaagcatcag gaatattgac tagtgaaaaa atggctaata    6840
ttgagcagga aaatgaaaaa ttgaaggctg aattagaaaa acttaaagct catcttgggc    6900
atcagttgag catgcactat gaatccaaga ccaaaggcac agaaaaaatt attgctgaaa    6960
atgaaaggct tcgtaaagaa cttaaaaaag aaactgatgc tgcagagaaa ttacggatag    7020
caaagaataa tttagagata ttaaatgaga agatgacagt tcaactagaa gagactggta    7080
agagattgca gtttgcagaa agcagaggtc cacagcttga aggtgctgac agtaagagct    7140
ggaaatccat tgtggttaca agaatgtatg aaaccaagtt aaaagaattg gaaactgata    7200
ttgccaaaaa aaatcaaagc attactgacc ttaaacagct tgtaaaagaa gcaacagaga    7260
gagaacaaaa agttaacaaa tacaatgaag accttgaaca acagattaag attcttaaac    7320
atgttcctga aggtgctgag acagagcaag gccttaaacg ggagcttcaa gttcttagat    7380
tagctaatca tcagctggat aaagagaaag cagaattaat ccatcagata gaagctaaca    7440
aggaccaaag tggagctgaa agcaccatac ctgatgctga tcaactaaag gaaaaaataa    7500
aagatctaga gacacagctc aaaatgtcag atctagaaaa gcagcatttg aaggaggaaa    7560
taaagaagct gaaaaagaa ctggaaaatt ttgatccttc attttttgaa gaaattgaag    7620
atcttaagta taattacaag gaagaagtga agaagaatat tctcttagaa gagaaggtaa    7680
aaaaactttc agaacaattg ggagttgaat taactagccc tgttgctgct tctgaagagt    7740
ttgaagatga agaagaaagt cctgttaatt tccccattta ctaaaggtca cctataaact    7800
ttgtttcatt taactatttta ttaactttat aagttaaata tacttggaaa taagcagttc    7860
tccgaactgt agtatttcct tctcactacc ttgtaccttt atacttagat tggaattctt    7920
aataaataaa attatatgaa attttcaact tattaaaaaa aaaaaaaaa aa             7972
```

<210> SEQ ID NO 9
<211> LENGTH: 738
<212> TYPE: PRT
<213> ORGANISM: Artificial Sequence
<220> FEATURE:
<223> OTHER INFORMATION: Synthetic Polypeptide

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Gln Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
    355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
            405                 410                 415

Thr Phe Glu Asp Val Pro Phe His Ser Ser Tyr Ala His Ser Gln Ser
```

-continued

```
              420             425             430
Leu Asp Arg Leu Met Asn Pro Leu Ile Asp Gln Tyr Leu Tyr Tyr Leu
        435             440             445

Ser Arg Thr Gln Thr Thr Gly Gly Thr Ala Asn Thr Gln Thr Leu Gly
        450             455             460

Phe Ser Gln Gly Gly Pro Asn Thr Met Ala Asn Gln Ala Lys Asn Trp
465             470             475             480

Leu Pro Gly Pro Cys Tyr Arg Gln Gln Arg Val Ser Thr Thr Thr Gly
                485             490             495

Gln Asn Asn Ser Asn Phe Ala Trp Thr Ala Gly Thr Lys Tyr His
        500             505             510

Leu Asn Gly Arg Asn Ser Leu Ala Asn Pro Gly Ile Ala Met Ala Thr
        515             520             525

His Lys Asp Asp Glu Glu Arg Phe Phe Pro Ser Asn Gly Ile Leu Ile
        530             535             540

Phe Gly Lys Gln Asn Ala Ala Arg Asp Asn Ala Asp Tyr Ser Asp Val
545             550             555             560

Met Leu Thr Ser Glu Glu Ile Lys Thr Thr Asn Pro Val Ala Thr
                565             570             575

Glu Glu Tyr Gly Ile Val Ala Asp Asn Leu Gln Gln Asn Thr Ala
            580             585             590

Pro Gln Ile Gly Thr Val Asn Ser Gln Gly Ala Leu Pro Gly Met Val
        595             600             605

Trp Gln Asn Arg Asp Val Tyr Leu Gln Gly Pro Ile Trp Ala Lys Ile
        610             615             620

Pro His Thr Asp Gly Asn Phe His Pro Ser Pro Leu Met Gly Gly Phe
625             630             635             640

Gly Leu Lys His Pro Pro Gln Ile Leu Ile Lys Asn Thr Pro Val
                645             650             655

Pro Ala Asp Pro Pro Thr Thr Phe Asn Gln Ser Lys Leu Asn Ser Phe
                660             665             670

Ile Thr Gln Tyr Ser Thr Gly Gln Val Ser Val Glu Ile Glu Trp Glu
        675             680             685

Leu Gln Lys Glu Asn Ser Lys Arg Trp Asn Pro Glu Ile Gln Tyr Thr
        690             695             700

Ser Asn Tyr Tyr Lys Ser Thr Ser Val Asp Phe Ala Val Asn Thr Glu
705             710             715             720

Gly Val Tyr Ser Glu Pro Arg Pro Ile Gly Thr Arg Tyr Leu Thr Arg
                725             730             735

Asn Leu
```

MINIGENE THERAPY

RELATED APPLICATIONS

This application is a National Stage Application of PCT/US2018/026230, filed Apr. 5, 2018, entitled "MINIGENE THERAPY", which claims the benefit under 35 U.S.C. § 119(e) of the filing date of U.S. Provisional Application Serial No. 62/481,727, filed on Apr. 5, 2017, entitled "CEP290 MINIGENE THERAPY", the entire contents of each application which are incorporated by reference herein.

GOVERNMENT SUPPORT

This invention was made with government support under grant numbers EY022372, EY029050, NS076991, AI100263, and HL131471, awarded by the National Institutes of Health. The government has certain rights in the invention.

BACKGROUND

Ciliopathies represent a group of diseases and disorders characterized by abnormal cilial formation or function. For example ocular ciliopathies may lead to retinal degeneration, reduced visual acuity, and/or blindness. CEP290-associated Leber congenital amaurosis (LCA) is one of the most common and severe forms of retinal degenerative diseases. However, no treatment or cure currently exists. Generally, the large size of cilia-associated genes, for example the CEP290 gene (~8 kb), has limited the development of successful therapy using conventional Adeno-associated Viral (AAV) vector-mediated gene delivery approaches. Use of genome editing (such as CRISPR/Cas9 approach) and antisense oligonucleotides can have off-target effects and are typically applicable to only one type of mutation in a cilia-associated gene. Accordingly, novel compositions and methods for treating ciliopathies are needed.

SUMMARY

Aspects of the disclosure relate to compositions and methods useful for delivering minigenes to a subject. Accordingly, the disclosure is based, in part, on gene therapy vectors, such as viral (e.g., rAAV) vectors, comprising one or more gene fragments encoding a therapeutic gene product, such as a protein or peptide (e.g., a minigene), and optionally one or more inhibitory nucleic acids that target an endogenous gene variant (e.g., mutant) that is associated with a disease or disorder (e.g., a gene associated with a ciliopathy). In some embodiments, the one or more inhibitory nucleic acids do not silence gene expression of the gene product encoded by the minigene. In some embodiments, methods are provided for treating ciliopathies (e.g., ocular ciliopathies), for example disorders and diseases characterized by a mutation or deletion of a cilia-associated gene, such as the CEP290 gene which is associated with Leber congenital amaurosis (LCA).

Accordingly, in some aspects, the disclosure relates to a viral vector comprising an expression cassette comprising a first isolated nucleic acid sequence encoding a therapeutic minigene and a second isolated nucleic acid sequence encoding one or more inhibitory nucleic acids, wherein the expression cassette is flanked by viral replication sequences, and wherein the one or more inhibitory nucleic acids do not bind to the isolated nucleic acid encoding the therapeutic minigene.

The disclosure is based, in part, on the unexpected discovery that AAV-mediated delivery of CEP290 gene fragments (e.g. encoding CEP290 protein fragments) lacking the "M region" to cells (e.g., ocular cells) of a subject having a disease or disorder characterized by a mutation or deletion of the CEP290 gene restores or improves cilial length and rescues or improves photoreceptor function. This discovery is surprising in view of previous disclosures, for example US 2016/0185832, which describes that the "M region" of the CEP290 gene is necessary to mediate microtubule localization and cilium formation. In some embodiments, the Examples section of this disclosure describes domains (e.g., fragments) of CEP290 protein that retain function in photoreceptors and can be delivered using the conventional AAV vectors.

Accordingly, in some aspects, the disclosure provides an isolated nucleic acid comprising: a first region comprising a first adeno-associated virus (AAV) inverted terminal repeat (ITR), or a variant thereof; and, a second region comprising a transgene encoding a CEP290 protein fragment, wherein the CEP290 protein fragment does not comprise amino acid positions 1695 to 1966 of SEQ ID NO: 1.

In some aspects, the disclosure provides an isolated nucleic acid comprising: a first region comprising a first adeno-associated virus (AAV) inverted terminal repeat (ITR), or a variant thereof; and, a second region comprising a transgene encoding a CEP290 protein fragment, wherein the CEP290 protein fragment comprises at least 500 contiguous amino acids of SEQ ID NO: 1. In some embodiments, the at least 500 contiguous amino acids comprises or consists of a sequence selected from SEQ ID NOs: 2, 3 and 4.

In some embodiments, the second region does not comprise amino acid positions 1695 to 1966 of SEQ ID NO: 1. In some embodiments, the transgene comprises no more than 1120 contiguous amino acids of SEQ ID NO: 1.

In some embodiments, the transgene comprises amino acid positions 580 to 1695 of SEQ ID NO: 1. In some embodiments, the CEP290 protein fragment encoded by the transgene comprises a sequence set forth in SEQ ID NO: 2. In some embodiments, the CEP290 protein fragment encoded by the transgene comprises amino acid positions 580 to 1180 of SEQ ID NO: 1, or amino acid positions 1181 to 1695 of SEQ ID NO: 1. In some embodiments, the CEP290 protein fragment encoded by the transgene comprises or consists of a sequence set forth in SEQ ID NO: 3 or 4.

In some embodiments, the transgene comprises or consists of a nucleic acid sequence selected from SEQ ID NO: 5, 6 and 7.

In some embodiments, the transgene further comprises one or more inhibitory nucleic acids, such as dsRNA, siRNA, shRNA, miRNA, artificial miRNA (amiRNA), etc. In some embodiments, the one or more inhibitory nucleic acids inhibit expression of endogenously-expressed CEP290 in a subject but do not inhibit expression of a CEP290 protein fragment encoded by the transgene.

In some embodiments, the transgene further comprises a promoter. In some embodiments, the promoter is a chicken beta-actin (CBA) promoter or a tissue-specific promoter. In some embodiments, the tissue specific promoter is an eye-specific promoter, optionally a retinoschisin promoter, K12 promoter, a rhodopsin promoter, a rod-specific promoter, a cone-specific promoter, a rhodopsin kinase promoter (e.g., GRK1 promoter), or interphotoreceptor retinoid-binding protein proximal (IRBP) promoter. In some embodiments, the promoter is an RNA pol II promoter or an RNA pol III promoter.

In some embodiments, the isolated nucleic acid further comprises a third region comprising a second adeno-associated virus (AAV) inverted terminal repeat (ITR), or a variant thereof.

In some embodiments, the first region and/or the third region is an AAV1 ITR, AAV2 ITR, AAV5 ITR, AAV6 ITR, AAV6.2 ITR, AAV7 ITR, AAV8 ITR, AAV9 ITR, AAV10 ITR, AAV11 ITR, or a variant thereof. In some embodiments, the first region and/or the third region is an AAV2 ITR or a variant thereof.

In some aspects, the disclosure provides a vector comprising an isolated nucleic acid as described by the disclosure. In some embodiments, the vector is a plasmid.

In some aspects, the disclosure provides a host cell comprising an isolated nucleic acid, or a vector as described by the disclosure.

In some aspects, the disclosure provides a recombinant adeno-associated virus (rAAV) comprising: a capsid protein; and, an isolated nucleic acid as described by the disclosure. In some embodiments, the capsid protein is AAV8 capsid protein or AAV5 capsid protein. In some embodiments, the capsid protein comprises the sequence set forth in SEQ ID NO: 9.

In some embodiments, the rAAV is a self-complementary AAV (scAAV).

In some embodiments, the rAAV is formulated for delivery to the eye.

In some aspects, the disclosure provides a composition comprising an rAAV as described by the disclosure, and a pharmaceutically acceptable excipient.

In some aspects, the disclosure provides methods for treating a disease or disorder (e.g., a monogenic disease, a ciliopathy, etc.) in a subject in need thereof, the methods comprising administering to a subject having the disease or disorder (e.g. a monogenic disease, a ciliopathy, etc.) a therapeutically effective amount of an isolated nucleic acid, or a rAAV as described by the disclosure.

In some embodiments, the methods further comprise the step of administering to the subject one or more inhibitory nucleic acids (e.g., one or more expression constructs encoding one or more inhibitory nucleic acids). In some embodiments, the one or more inhibitory nucleic acids inhibit expression of one or more genes associated with the disease or disorder (e.g., monogenic disease, ciliopathy, etc.). In some embodiments, the one or more inhibitory nucleic acids do not inhibit expression of a transgene encoded by an isolated nucleic acid or rAAV as described by the disclosure.

In some aspects, the disclosure provides a method for treating an ocular ciliopathy in a subject in need thereof, the method comprising administering to a subject having an ocular ciliopathy a therapeutically effective amount of an isolated nucleic acid, or a rAAV as described by the disclosure.

In some embodiments, the ocular ciliopathy is associated with a mutation of the CEP290 gene in the subject or a deletion of the CEP290 gene in the subject. In some embodiments, the mutation or deletion of CEP290 gene results in retinal degeneration, photoreceptor degeneration, retinal dysfunction, and/or loss of vision.

In some embodiments, the ocular ciliopathy is Leber congenital amaurosis (LCA), Joubert syndrome, Bardet-Biedl syndrome, Meckel syndrome, Usher syndrome, Nephronophthisis, or Senior-Løken syndrome. In some embodiments, the ocular ciliopathy is Leber congenital amaurosis (LCA).

In some embodiments, the mutation in the CEP290 gene is an intronic mutation, a nonsense mutation, a frameshift mutation, a missense mutation, or any combination thereof.

In some embodiments, the subject is human and the CEP290 gene mutation occurs at position c.2991+1655, optionally wherein the mutation is A1655G.

In some embodiments, the administration results in delivery of the isolated nucleic acid or rAAV to the eye of the subject. In some embodiments, the administration is via injection, optionally subretinal injection or intravitreal injection. In some embodiments, the administration is topical administration to the eye of the subject. In some embodiments, an isolated nucleic acid or rAAV as described by the disclosure is administered more than once to a subject (e.g., 2, 3, 4, 5, or more times). In some embodiments, the administrations are spaced more than 4 weeks apart.

In some embodiments, the method further comprises administering one or more inhibitory nucleic acids to the subject, wherein the one or more inhibitory nucleic acids does not bind to a nucleic acid sequence encoding amino acid residues 580 to 1180 of SEQ ID NO: 1, or 1181 to 1695 of SEQ ID NO: 1.

BRIEF DESCRIPTION OF DRAWINGS

Molecular mass marker is shown in kDa.

FIG. 7A shows Cep290$^{rd16}$ mice subretinally injected at P0/P1 stage with indicated miniCEP290s or GFP, and analyzed by ERG at 3 weeks post injection. Age-matched uninjected WT or Cep290$^{rd16}$ (littermates) mice were used as controls for ERG. The ERG a-wave is represented by arrows while b-wave vis depicted using arrowheads. Data represent analysis of at least 6 mice. ***: p<0.0001; ns: not significant. FIG. 7B shows scotopic a-wave and b-wave amplitude for mice subretinally injected at P0/P1 stage with indicated miniCEP290s or GFP, and analyzed by ERG at 3 weeks post injection.

FIG. 8A shows Cep290$^{rd16}$ retinas injected with indicated miniCEP290$^{580-1180}$ or GFP stained with DAPI. FIG. 8B shows Cep290$^{rd16}$ retinas injected with indicated miniCEP290$^{580-1180}$ or GFP assessed by ultrathin sectioning. ONL (outer nuclear layer) is marked with vertical lines. WT retinal section is shown for comparison. INL: inner nuclear layer. FIG. 8C shows improved expression of RDS detected in the miniCEP290$^{580-1180}$ injected Cep290$^{rd16}$ mice. GFP staining marks the injected regions. FIG. 8D shows retinal cryosections of Cep290$^{rd16}$ mice injected with the indicated miniCEP290s were stained with GFP (injected regions), rhodopsin (RHO; rod-specific; or M-opsin (MOP; cone-specific) antibodies and DAPI (nuclei). Outer segment (OS)-enriched opsin staining is detected in the miniCEP290$^{580-1180}$-injected retinas. Dramatically reduced expression of opsins is detected in the miniCEP290$^{2037-2479}$-injected retinas. ONL: outer nuclear layer; INL: inner nuclear layer; GCL: ganglion cell layer.

DETAILED DESCRIPTION

Figure 1:
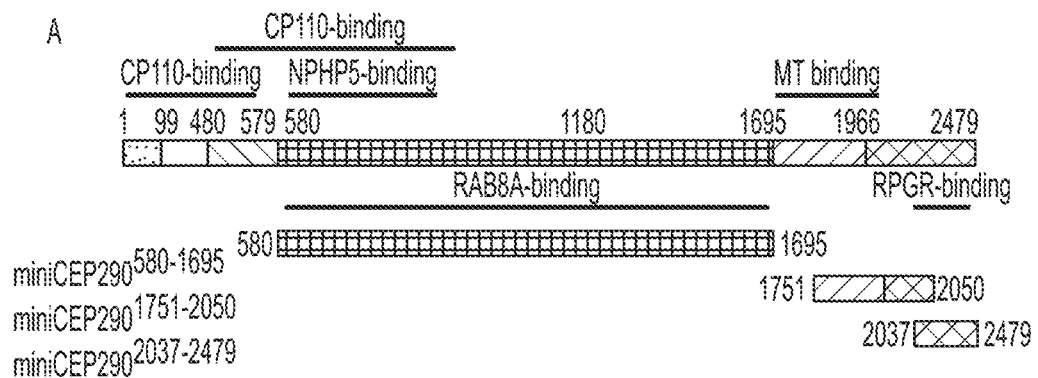
FIG. 1 shows schematic depiction of the full-length CEP290 gene representing the locations of distinct protein interaction domains.

In some aspects, the disclosure relates to compositions and methods useful for treating certain genetic diseases, for example monogenic diseases, ciliopathies, etc. Monogenic diseases are diseases that are diseases that result from abnormal expression or function of a single allele of a gene. Examples of monogenic diseases include but are not limited to thalassemia, sickle cell anemia, hemophilia, cystic fibrosis, Tay Sachs disease, Fragile X syndrome, Huntington's disease, etc. Ciliopathies are genetic disorders that affect the expression or function of cellular cilia. Examples of ciliopathies include but are not limited to Alstrom syndrome, Bardet-Biedl syndrome, Joubert syndrome, Merckel syndrome, nephronophthisis, orofaciodigital syndrome, Senior-Locken syndrome, polycystic kidney disease, primary ciliary dyskinesia, and situs *inversus*.

The disclosure is based, in part, on gene therapy vectors, such as viral (e.g., rAAV) vectors, comprising one or more gene fragments encoding a therapeutic gene product, such as a protein or peptide (e.g., a minigene), and optionally one or more inhibitory nucleic acids that target an endogenous gene variant (e.g., mutant) that is associated with a disease or disorder (e.g., a gene associated with a ciliopathy).

A gene therapy vector may be a viral vector (e.g., a lentiviral vector, an adeno-associated virus vector, etc.), a plasmid, a closed-ended DNA (e.g., ceDNA), etc. In some embodiments, a gene therapy vector is a viral vector. In some embodiments, an expression cassette encoding a minigene is flanked by one or more viral replication sequences, for example lentiviral long terminal repeats (LTRs) or adeno-associated virus (AAV) inverted terminal repeats (ITRS).

As used herein, "minigene" refers to an isolated nucleic acid sequence encoding a recombinant peptide or protein where one or more non-essential elements of the corresponding gene encoding the naturally-occurring peptide or protein have been removed and where the peptide or protein encoded by the minigene retains function of the corresponding naturally-occurring peptide or protein. A "therapeutic minigene" refers to a minigene encoding a peptide or protein useful for treatment of a genetic disease, for example dystrophin, dysferlin, Factor VIII, Amyloid precursor protein (APP), Tyrosinase (Tyr), etc. Minigenes are known in the art and are described, for example by Karpati and Acsadi (1994) *Clin Invest Med* 17(5):499-509; Plantier et al. (2001) *Thromb Haemost.* 86(2):596-603; and Xiao et al. (2007) *World J. Gastroenterol.* 13(2):244-9.

Generally, an isolated nucleic acid encoding a minigene (e.g., a therapeutic minigene) is between about 10% and about 99% (e.g., about 10%, about 15%, about 20%, about 25%, about 30%, about 40% about 50%, about 60%, about 70%, about 75%, about 80%, about 90%, about 99%, etc.) truncated with respect to a nucleic acid sequence encoding the corresponding naturally-occurring wild-type protein. For example, in some embodiments, a minigene encoding a CEP290 protein fragment is about 76% truncated (e.g., comprises about 24% of the nucleic acid sequence) compared to a wild-type CEP290 gene.

In some embodiments, a gene therapy vector further comprises one or more inhibitory nucleic acids that do not silence gene expression of the gene product encoded by the minigene but do silence gene expression of an endogenous protein corresponding to a wild-type or disease-associated variant of the protein encoded by the minigene. For example, in some embodiments, a gene therapy vector comprises a minigene encoding a CEP290 protein fragment and one or more inhibitory nucleic acids (e.g., dsRNA, siRNA, shRNA, miRNA, amiRNA, etc.) that inhibit expression of endogenously expressed CEP290 (e.g., a CEP290 mutant selected from c.2991+1655A>G, c.2249T>G, c.7341dupA, c.2118_2122dupTCAGG, c.3814C>T, c.679_680delGA, c.265dupA, c.180+1G?T, c.1550delT, c.4115_4116delTA, c.4966G>T, and c.5813_5817delCTTTA) but do not inhibit expression of the CEP290 fragment encoded by the minigene. The skilled artisan will also appreciate that, in some embodiments, one or more inhibitory nucleic acids that that inhibit expression of endogenously expressed CEP290 but do not inhibit expression of the CEP290 fragment encoded by the minigene may be administered to a subject in a manner that is separate from the gene therapy construct.

Methods for Treating Ocular Ciliopathies

Aspects of the invention relate to certain protein-encoding transgenes (e.g., fragments of human CEP290) that when delivered to a subject are effective for promoting growth of ocular cilia (e.g., cilia of photoreceptors) and rescue of photoreceptor structure and function in the subject. Accordingly, methods and compositions described by the disclosure are useful, in some embodiments, for the treatment of ocular ciliopathies associated with mutations or deletions of CEP290 gene, such as Leber congenital amaurosis (LCA), Joubert syndrome, Bardet-Biedl syndrome, Meckel syndrome, Usher syndrome, and Senior-Løken syndrome.

Methods for delivering a transgene (e.g., a gene encoding a CEP290 protein or a fragment thereof) to a subject are provided by the disclosure. The methods typically involve administering to a subject an effective amount of an isolated nucleic acid encoding a CEP290 protein fragment, or a rAAV comprising a nucleic acid for expressing a CEP290 protein fragment.

The human CEP290 gene consists of 52 exons, which encode for a protein of ~290 kDa (2479 amino acids). In some embodiments, the human CEP290 gene encodes a protein comprising the amino acid sequence set forth in SEQ ID NO: 1, and as described as GenBank Accession Number (NP_079390.3). In some embodiments, the human CEP290 gene (e.g., NCBI Reference Sequence: NM_025114.3) comprises a sequence set forth in SEQ ID NO: 8.

CEP290 is a multidomain protein and contains numerous coiled-coil domains distributed over the entire length of the protein. In addition, the CEP290 protein contains membrane and microtubule-binding domains and myosin-tail homology domain. Typically, CEP290 predominantly localizes to the centrosomes and transition zone of primary cilia and to the CC of photoreceptors. Previous publications have observed that the domain of CEP290 that localizes the protein to centrosomes (e.g., the "M region" of the CEP290 gene, as described in US 2016/0185832) is necessary to mediate microtubule localization and cilium formation. In some embodiments, the "M region" refers to amino acid residues 1695 to 1966 of human CEP290, as described in US 2016/0185832.

Aspects of the instant disclosure are based, in part, on the surprising discovery that certain CEP290 fragments lacking the "M" region mediate effective rescue of cilial formation and photoreceptor rescue when expressed in a subject in need thereof, for example via administration of a viral vector (e.g., rAAV).

Accordingly in some aspects, the disclosure provides a transgene encoding a CEP290 protein fragment, wherein the CEP290 protein fragment does not comprise amino acid positions 1695 to 1966 (e.g., a region encompassing the "M" region) of SEQ ID NO: 1. A "CEP protein fragment" refers to a 2 to 2479 (e.g., any integer between 2 and 2479) amino acid portion of a CEP290 protein. In some embodiments, the CEP protein fragment comprises a contiguous amino acid portion (e.g., amino acids 580 to 1180) of CEP290 (e.g., SEQ ID NO: 1). In some embodiments, the CEP protein fragment comprises one or more (e.g., 2, 3, 4, 5, 6, 7, 8, 9, 10, or more) interrupted amino acid portions (e.g., amino acids 1 to 10, 580 to 1180 and 1967 to 2470) of CEP290 (e.g., SEQ ID NO: 1)

In some embodiments, the CEP290 protein fragment comprises at least 500 contiguous amino acids of SEQ ID NO: 1. For example, in some embodiments, the CEP290 protein fragment comprises (or consists of) amino acids 580 to 1695, or amino acids 580 to 1180, or amino acids 1181 to 1695, of CEP290 (e.g., SEQ ID NO: 1). In some embodiments, the at least 500 contiguous amino acids comprises or consists of a sequence selected from SEQ ID NOs: 2, 3 and 4. In some embodiments, the disclosure provides a transgene comprising a nucleic acid (e.g., isolated nucleic acid) encoding a CEP290 protein fragment. In some embodiments, the transgene comprises or consists of a nucleic acid sequence selected from SEQ ID NO: 5, 6 and 7.

In some embodiments, the transgenes encoding a CEP290 fragment described by the disclosure mediate cilial growth and photoreceptor rescue, and are therefore useful for treating ciliopathies, for example ocular ciliopathies. Generally, a ciliopathy" refers to a disease or disorder characterized by defective (or lack of) protein function resulting in abnormal formation or function of cilia in a cell of a subject. An "ocular ciliopathy" is a ciliopathy where abnormal formation or function of cilial occurs in ocular cells (e.g., rods, cones, photoreceptor cells, etc.) of a subject, typically resulting in retinal degeneration, loss of vision and blindness. Examples of ciliopathies include but are not limited to earlier onset developmental anomalies such as Meckel Gruber Syndrome and Joubert Syndrome, to relatively later onset diseases, such as Bardet-Biedl Syndrome, Senior-Loken Syndrome, and Usher Syndrome. In some embodiments, retinal dystrophies (e.g., due to an ocular ciliopathy) are more commonly presented in a nonsyndromic manner.

In some embodiments, the ocular ciliopathy is Leber congenital amaurosis (LCA). Generally, LCA is a clinically and genetically heterogeneous disease with early onset severe retinal degeneration starting either at birth or by 5-7 years of age. Generally, a mutation or mutations in CEP290 account for >26% of LCA (LCA10; OMIM 611755). In some embodiments, LCA is characterized by a deletion of the CEP290 gene in a subject. Generally, a mutation in CEP290 that results in LCA may be an intronic mutation, a nonsense mutation, a frameshift mutation, a missense mutation, or any combination thereof. Examples of CEP290 gene mutations associated with LCA include but are not limited to c.2991+1655A>G, c.2249T>G, c.7341dupA, c.2118_2122dupTCAGG, c.3814C>T, c.679_680delGA, c.265dupA, c.180+1G?T, c.1550delT, c.4115_4116delTA, c.4966G>T, and c.5813_5817delCTTTA, for example as described by den Hollander et al. (2006) Am J Hum Genet. 79(3):556-561. In some embodiments, the mutation in CEP290 is a deep intronic mutation, for example at position c.2991+1655A. In some embodiments, the deep intronic mutation is c.2991+1655A>G.

Deletions and or mutations in a CEP290 gene of a subject (e.g., a subject having or suspected of having a ciliopathy associated with a deletion or mutation of CEP290 gene) may be identified from a sample obtained from the subject (e.g., a DNA sample, RNA sample, blood sample, or other biological sample) by any method known in the art. For example, in some embodiments, a nucleic acid (e.g., DNA, RNA, or a combination thereof) is extracted from a biological samples obtained from a subject and nucleic acid sequencing is performed in order to identify a mutation in the CEP290 gene. Examples of nucleic acids sequencing techniques include but are not limited to Maxam-Gilbert sequencing, pyrosequencing, chain-termination sequencing, massively parallel signature sequencing, single-molecule sequencing, nanopore sequencing, Illumina sequencing, etc. In some embodiments, a mutation or deletion in CEP290 gene is detected indirectly, for example by quantifying CEP290 protein expression (e.g., by Western blot) or function (e.g., by analyzing cilial growth, structure, function, etc.), or by direct sequencing of the DNA and comparing the sequence obtained to a control DNA sequence (e.g., a wild-type CEP290 DNA sequence).

In some aspects, the disclosure provides a method for treating an ocular ciliopathy in a subject in need thereof, the method comprising administering to a subject having an ocular ciliopathy a therapeutically effective amount of an isolated nucleic acid, or a rAAV, as described by the disclosure.

An "effective amount" of a substance is an amount sufficient to produce a desired effect. In some embodiments, an effective amount of an isolated nucleic acid (e.g., an isolated nucleic acid comprising a transgene encoding a CEP290 protein fragment as described herein) is an amount sufficient to transfect (or infect in the context of rAAV mediated delivery) a sufficient number of target cells of a target tissue of a subject. In some embodiments, a target tissue is ocular tissue (e.g., photoreceptor cells, rod cells, cone cells, retinal ganglion cells, retinal cells, etc.). In some embodiments, an effective amount of an isolated nucleic acid (e.g., which may be delivered via an rAAV) may be an amount sufficient to have a therapeutic benefit in a subject, e.g., to increase or supplement the expression of a gene or protein of interest (e.g., CEP290), to improve in the subject one or more symptoms of disease (e.g., a symptom of an ocular ciliopathy, such as LCA), etc. The effective amount will depend on a variety of factors such as, for example, the species, age, weight, health of the subject, and the tissue to be targeted, and may thus vary among subject and tissue as described elsewhere in the disclosure.

Isolated Nucleic Acids

In some aspects, the disclosure provides isolated nucleic acids that are useful for expressing human CEP290, or a fragment thereof. A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

The isolated nucleic acids of the invention may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more proteins (e.g., human CEP290, or a fragment thereof). The transgene may also comprise a region encoding, for example, a miRNA binding site, and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, and variants thereof. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV5, AAV6, AAV6.2, AAV7, AAV8, AAV9, AAV10, AAV11, and variants thereof. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) *Molecular Therapy* 16(10): 1648-1656.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., miRNA).

A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P etal., Human Gene Therapy, 2000; 11: 1921-1931.; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter. In some embodiments, a promoter is a U6 promoter. In some embodiments, a promoter is a chicken beta-actin (CBA) promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the tissue-specific promoter is an eye-specific promoter. Examples of eye-specific promoters include but are not limited to a retinoschisin promoter, K12 promoter, a rhodopsin promoter, a rod-specific promoter, a cone-specific promoter, a rhodopsin kinase promoter, a GRK1 promoter, an interphotoreceptor retinoid-binding protein proximal (IRBP) promoter, and an opsin promoter (e.g., a red opsin promoter, a blue opsin promoter, etc.).

In some embodiments, a promoter is a RNA polymerase III (pol III) promoter. Non-limiting examples of pol III promoters include U6 and H1 promoter sequences. In some embodiments, a promoter is a RNA polymerase II (pol II) promoter. Non-limiting examples of pol II promoters include T7, T3, SP6, RSV, and cytomegalovirus promoter sequences. In some embodiments, a pol III promoter sequence drives expression of one or more inhibitory nucleic acids and a pol II promoter sequence drives expression of a minigene.

Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772, the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV2, AAV3, AAV4, AAV5, AAV6, AAV8, AAVrh8, AAV9, and AAV10. In some embodiments, an AAV capsid protein is of a serotype derived from a non-human primate, for example AAVrh8 serotype. In some embodiments, the AAV capsid protein is of a serotype that has tropism for the eye of a subject, for example an AAV (e.g., AAV5, AAV6, AAV6.2, AAV7, AAV8, AAV9, AAVrh.8, AAVrh.10, AAVrh.39 and AAVrh.43) that transduces ocular cells of a subject more efficiently than other vectors. In some embodiments, an AAV capsid protein is of an AAV8 serotype or an AAV5 serotype. In some embodiments, the AAV capsid protein comprises the sequence set forth in SEQ ID NO: 9.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a protein (e.g., a CEP290 protein fragment). In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene. The foregoing methods for packaging recombinant vectors in desired AAV capsids to produce the rAAVs of the disclosure are not meant to be limiting and other suitable methods will be apparent to the skilled artisan.

rAAV-Mediated Delivery of CEP290 Transgenes to the Eye

Methods for delivering a transgene to ocular (e.g., photoreceptors, such as rod cells or cone cells, retinal cells, etc.) tissue in a subject are provided herein. The methods typically involve administering to a subject an effective amount of a rAAV comprising a nucleic acid for expressing a transgene (e.g., a CEP290 protein fragment) in the subject. An "effective amount" of a rAAV is an amount sufficient to infect a sufficient number of cells of a target tissue in a subject. In some embodiments, a target tissue is ocular (e.g., photoreceptor, retinal, etc.) tissue. An effective amount of a rAAV may be an amount sufficient to have a therapeutic benefit in a subject, e.g., to improve in the subject one or more symptoms of disease, e.g., a symptom of an ocular ciliopathy (e.g., an ocular ciliopathy associated with a deletion or mutation of CEP290 gene, such as LCA). In some cases, an effective amount of a rAAV may be an amount sufficient to produce a stable somatic transgenic animal model. The effective amount will depend on a variety of factors such as, for example, the species, age, weight, health of the subject, and the ocular tissue to be targeted, and may thus vary among subject and tissue.

An effective amount may also depend on the rAAV used. The invention is based, in part on the recognition that rAAV comprising capsid proteins having a particular serotype (e.g., AAV5, AAV6, AAV6.2, AAV7, AAV8, AAV9, AAVrh.8, AAVrh.10, AAVrh.39, and AAVrh.43) mediate more efficient transduction of ocular (e.g., photoreceptor, retinal, etc.) tissue that rAAV comprising capsid proteins having a different serotype. Thus in some embodiments, the rAAV comprises a capsid protein of an AAV serotype selected from the group consisting of: AAV5, AAV6, AAV6.2, AAV7, AAV8, AAV9, AAVrh.8, AAVrh.10, AAVrh.39, and AAVrh.43. In some embodiments, the rAAV comprises a capsid protein of AAV8 serotype (SEQ ID NO: 9). In some embodiments, the capsid protein comprises an amino acid sequence that is at least 70%, at least 80%, at least 90%, at least 95%, or at least 99% identical to SEQ ID NO: 9. In some embodiments, the capsid protein is AAV5 capsid protein.

In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

An effective amount may also depend on the mode of administration. For example, targeting an ocular (e.g., photoreceptor, retinal, etc.) tissue by intrastromal administration or subcutaneous injection may require different (e.g., higher or lower) doses, in some cases, than targeting an ocular (e.g., photoreceptor, retinal, etc.) tissue by another method (e.g., systemic administration, topical administration). In some embodiments, intrastromal injection (IS) of rAAV having certain serotypes (e.g., AAV5, AAV6, AAV6.2, AAV7, AAV8, AAV9, AAVrh.8, AAVrh.10, AAVrh.39, and AAVrh.43) mediates efficient transduction of ocular (e.g., corneal, photoreceptor, retinal, etc.) cells. Thus, in some embodiments, the injection is intrastromal injection (IS). In some embodiments, the administration is via injection, optionally subretinal injection or intravitreal injection. In some embodiments, the injection is topical administration (e.g., topical administration to an eye). In some cases, multiple doses of a rAAV are administered.

Without wishing to be bound by any particular theory, efficient transduction of ocular (e.g., photoreceptor, retinal, etc.) cells by rAAV described herein may be useful for the treatment of a subject having an ocular disease (e.g., an ocular ciliopathy). Accordingly, methods and compositions for treating ocular disease are also provided herein. In some aspects, the disclosure provides a method for treating an ocular ciliopathy (e.g., an ocular ciliopathy associated with a deletion or mutation of CEP290 gene), the method comprising: administering to a subject having or suspected of having an ocular ciliopathy an effective amount of rAAV, wherein the rAAV comprises (i) a capsid protein having a serotype selected from the group consisting of AAV5, AAV6, AAV6.2, AAV7, AAV8, AAV9, AAVrh.8, AAVrh.10, AAVrh.39, and AAVrh.43, and (ii) a nucleic acid comprising a promoter operably linked to a transgene (e.g., a transgene encoding a CEP290 protein fragment as described by the disclosure).

In some embodiments, administration of a rAAV (or isolated nucleic acid) as described by the disclosure results in transduction of a cell or cells comprising a cilium, optionally a photoreceptor sensory cilium. The photoreceptor (PR) sensory cilium is nucleated from the basal body at the apical surface of the inner segment. As the microtubules extend, they form a doublet microtubule structure, called the connecting cilium (CC). The CC is analogous to the transition zone of a prototypic cilium and extends into the outer segment (OS) of the photoreceptor cell. The CC is acts as a conduit for unidirectional or bidirectional transport of cargo moieties between the inner and the outer segments. The CC also acts as a 'gatekeeper' to regulate the entry or exit of the cargo, which aids in the maintenance of its unique composition. In some embodiments, administration of a rAAV (or isolated nucleic acid) as described by the disclosure results in growth or formation of a photoreceptor sensory cilium, a connecting cilium, or a combination thereof.

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

Delivery of the rAAVs to a mammalian subject may be by, for example, intraocular injection or topical administration (e.g., eye drops). In some embodiments, the intraocular injection is intrastromal injection, subconjunctival injection, or intravitreal injection. In some embodiments, the injection is not topical administration. Combinations of administration methods (e.g., topical administration and intrastromal injection) can also be used.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue (e.g., ocular tissue, such as photoreceptor, retinal, etc., tissue) and to provide sufficient levels of gene transfer and expression without undue adverse effects. Examples of pharmaceutically acceptable routes of administration include, but are not limited to, direct delivery to the selected organ (e.g., subretinal delivery to the eye), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of an rAAV is an amount sufficient to target infect an animal, target a desired tissue. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^9$ rAAV genome copies is effective to target ocular tissue (e.g., corneal tissue). In some embodiments, a dose more concentrated than $10^9$ rAAV genome copies is toxic when administered to the eye of a subject. In some embodiments, an effective amount is produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to target tissue, e.g., direct to ocular tissue (e.g., photoreceptor, retinal, etc., tissue) However, in certain circumstances it may be desirable to separately or in addition deliver the rAAV-based therapeutic constructs via another route, e.g., subcutaneously, intrapancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by intravitreal injection or sub-retinal injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a rAAV, the kit comprising a container housing an isolated nucleic acid comprising a transgene encoding a CEP290 protein fragment having the amino acid sequence set forth in any one of SEQ ID NOs: 2-4. In some embodiments, the kit further comprises a container housing an isolated nucleic acid encoding an AAV capsid protein, for example an AAV8 capsid protein (e.g., SEQ ID NO: 9).

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

Exemplary embodiments of the invention will be described in more detail by the following examples. These embodiments are exemplary of the invention, which one skilled in the art will recognize is not limited to the exemplary embodiments.

Examples

Therapeutic Strategies for CEP290-LCA

The relative sparing of the central region of the CEP290-LCA patient retinas indicates that gene therapy may be a viable option for visual restoration in patients. However, progress in the development of mutation-independent gene replacement strategies for CEP290-LCA has been delayed largely because of unsuitability of the long CEP290 gene to be packaged into conventional AAV vector system for gene therapy. This example describes delivery of CEP290 fragments via AAV to treat CEP290-LCA. In some embodiments, the described CEP290 fragments restore cilial growth and photoreceptor function in a mutation-independent manner, and are thus useful for treatment of nonsyndromic LCA and retinal degeneration in systemic ciliopathies due to CEP290 mutations.

The full-length CEP290 cDNA is ~8 kb long, which generally exceeds the packaging limit of conventional AAV vectors. A schematic depiction of the full-length CEP290 gene representing the locations of distinct protein interaction domains is shown in FIG. 1. Here, CEP290 fragments that retain function in photoreceptors (PR) and can be delivered using the conventional AAV vectors were identified. As CEP290 is a ciliary protein and regulates cilia growth, an in vitro assay of cilia growth was developed in order to use as a surrogate marker to test the function of shorter CEP290 regions. It was observed that mouse embryonic fibroblasts (MEFs) derived from a Cep290-mutant (Cep290$^{rd16}$) mouse, which recapitulates the early onset severe PR degeneration phenotype, have fewer ciliated cells and the cells that formed cilia were shorter compared to controls. This observation is consistent with previous studies that revealed fewer and shorter cilia in fibroblasts derived from CEP290-LCA patient samples.

Figure 2A:
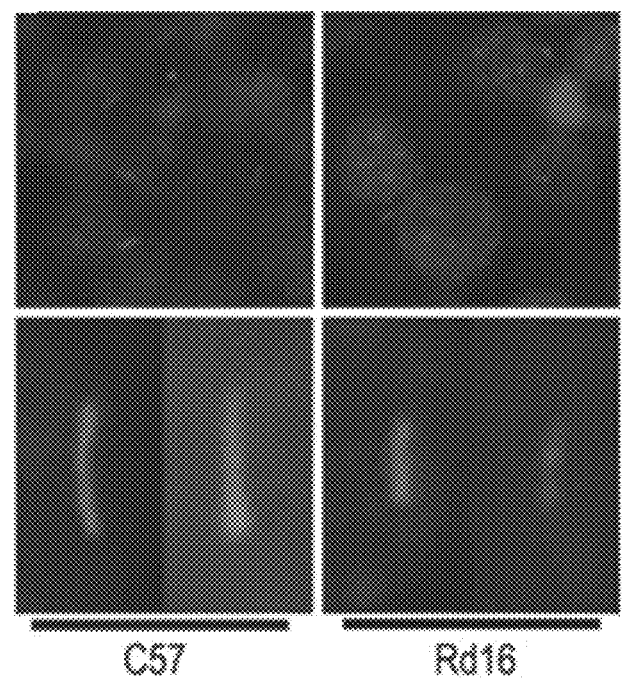
FIG. 2A shows microscopy data relating to cilial number and length in mouse embryonic fibroblasts (MEFs) from wild-type (WT) and Cep290$^{rd16}$ mice that were serum-starved for 24 h (for cilia growth) and then stained with anti-acetylated α-tubulin antibody (cilia marker). The lower images depict higher magnification of cilia.
Figure 2B:
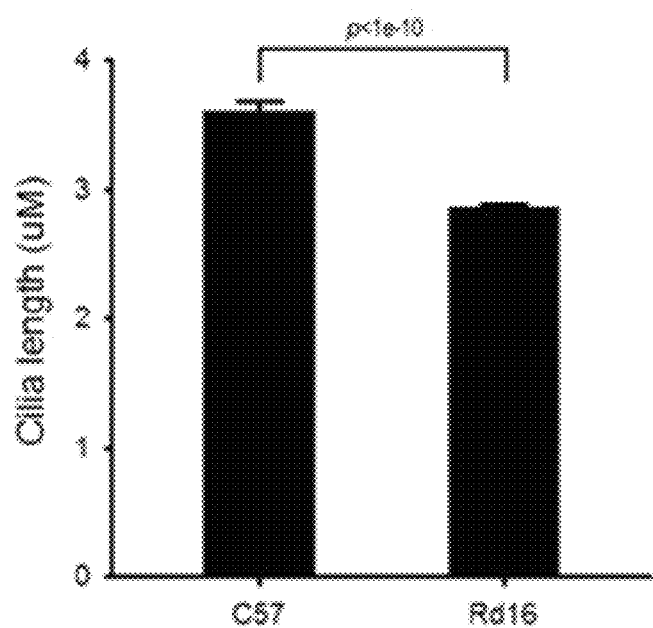
FIG. 2B shows a statistically significant decrease in the length of cilia in mutant MEFs.

As shown in FIGS. 2A-2B, cilia of Cep290$^{rd16}$ MEFs are ~2.7 μm in length as compared to controls, which have ~3.8 μm long cilia. In addition, fewer cells with cilia were detected among Cep290$^{rd16}$ MEFs as compared to controls.

Figure 3:
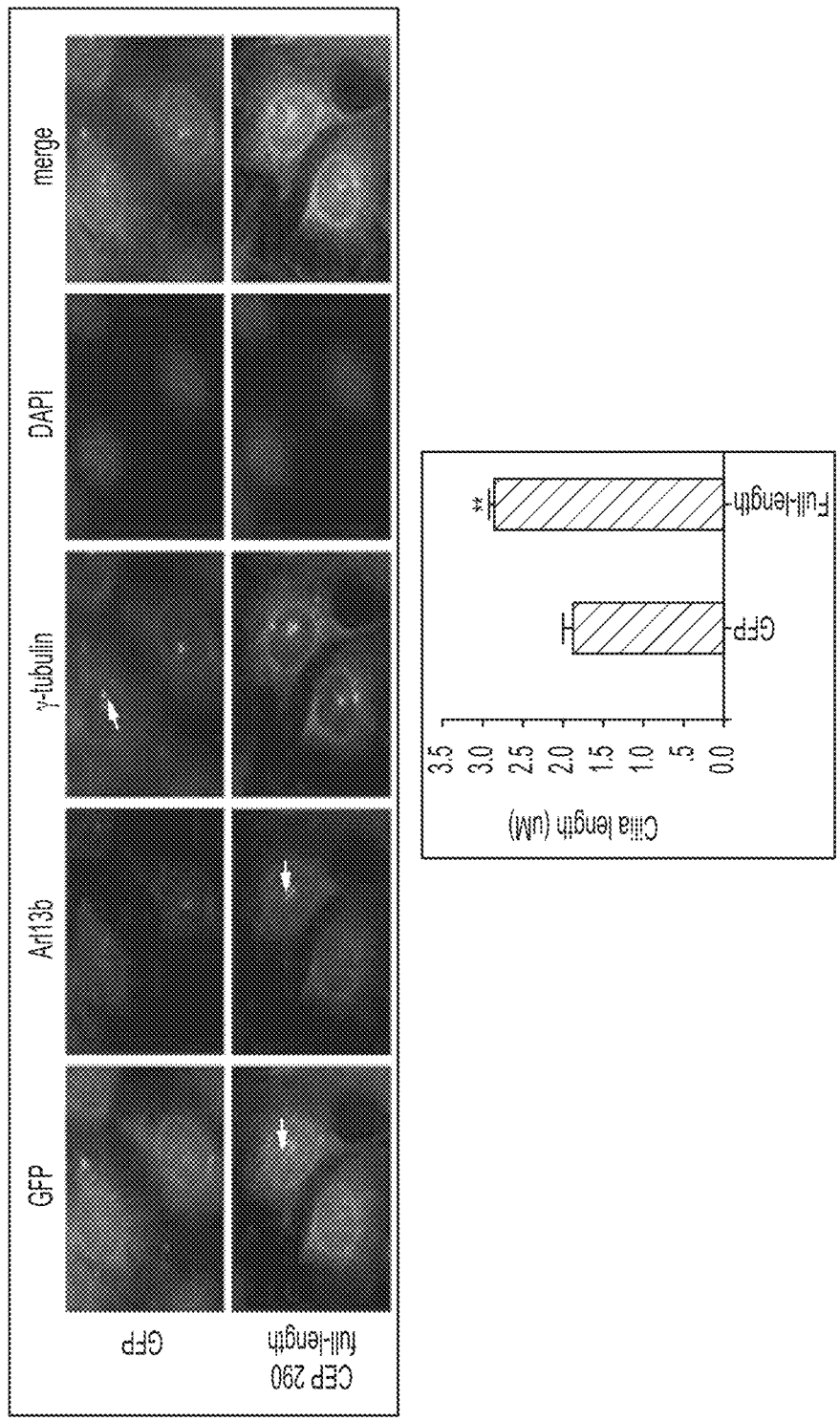
FIG. 3 shows Cep290$^{rd16}$ MEFs transfected with constructs encoding GFP or GFP-CEP290, followed by staining with ARL13b (cilia marker) and γ-tubulin. A significant increase in cilia length of cells expressing full-length CEP290 was observed. GFP-encoding construct was used as negative control. **: $p<0.001$.

Next, the effect of expressing full-length human CEP290 protein on cilia length in Cep290$^{rd16}$ MEFs was investigated. It was observed that the full-length human CEP290 protein correctly localizes to cilia, as determined by co-staining with ARL13b, which is a cilia marker (FIG. 3). Expressing GFP protein did not result in its localization to cilia. Additionally, measurement of cilia length showed that expression of CEP290 protein significantly rescued the cilia length of Cep290$^{rd16}$ MEFs as compared to expression of GFP.

Construction of vCEP290

Figure 4A:
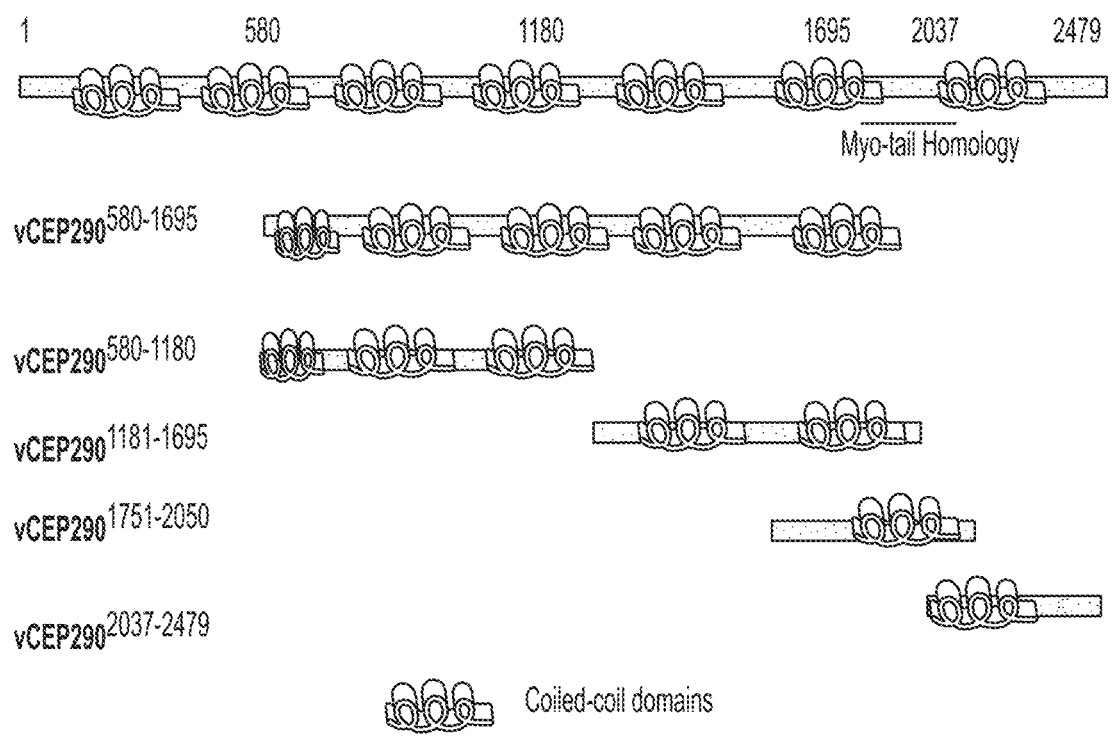
FIG. 4A shows a schematic representation of the human CEP290 protein and deleted variants. Myo-tail: Myosin tail homology domain. Additional protein-interaction domains are also not shown.
Figure 4B:
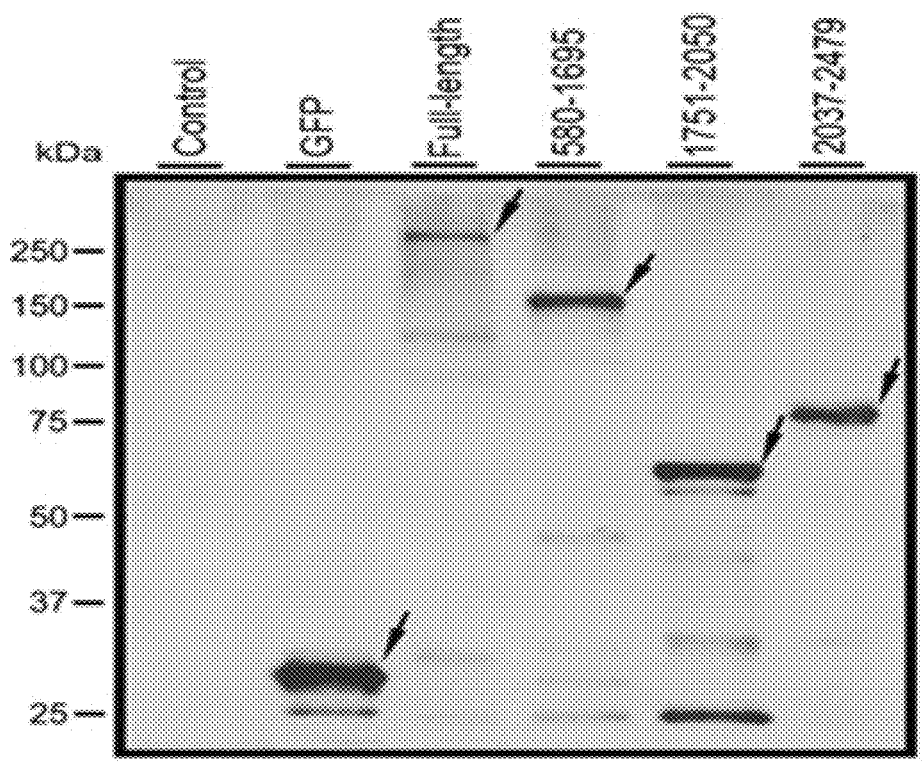
FIG. 4B shows immunoblot analysis using anti-GFP antibody of mouse fibroblasts transiently transfected with the constructs described in FIG. 4A. Specific protein bands (depicted by arrows) were detected indicating that the deleted variants are stably expressed in cells.
Figure 9:
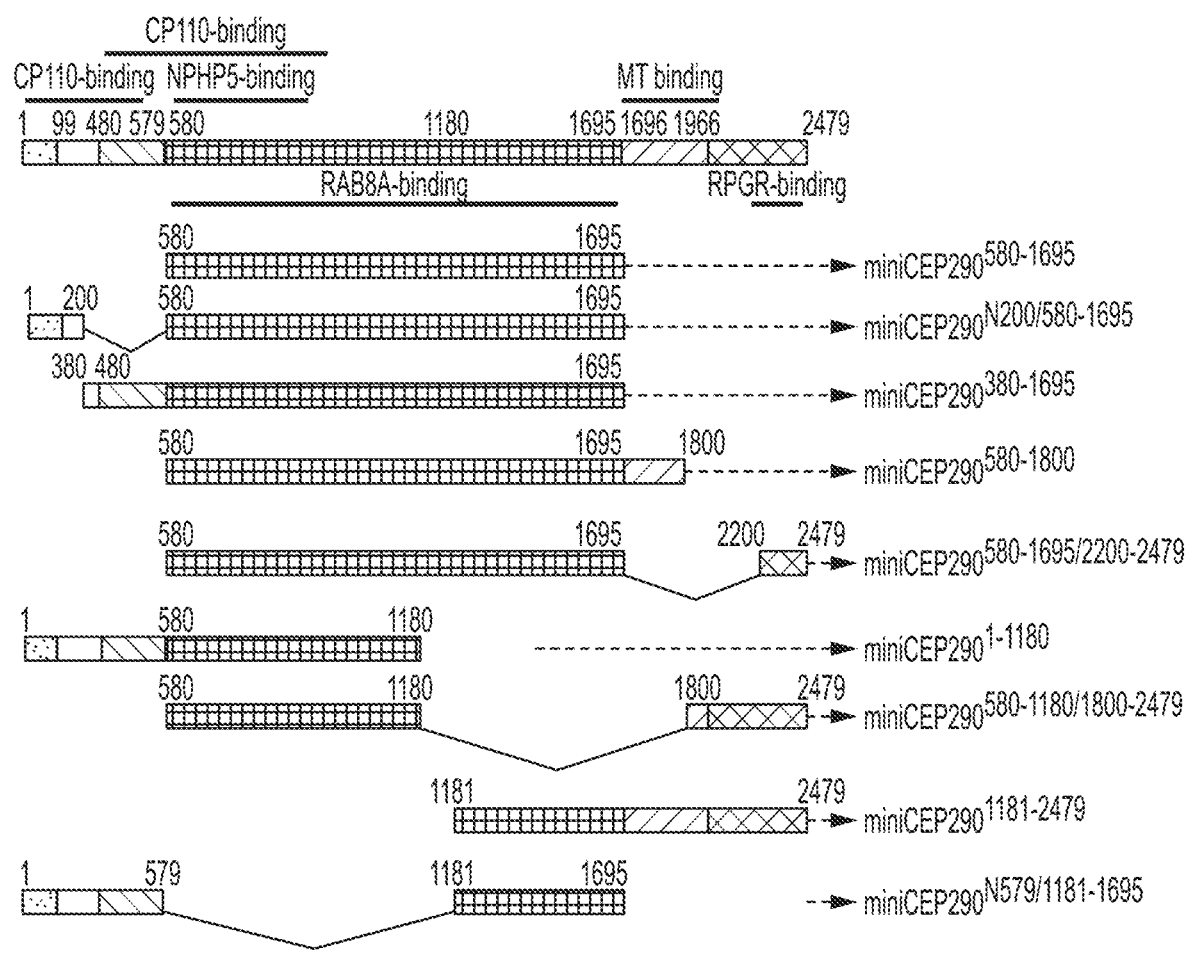
FIG. 9 shows additional embodiments of CEP290 minigenes.

The CEP290 gene encodes a predominantly coiled-coil protein. Constructs that removed repetitive domains of human CEP290, such as plasmids encoding GFP-fused miniCEP290$^{580-1695}$, miniCEP290$^{1751-2050}$ and miniCEP290$^{2037-2479}$ (FIG. 4A), were produced. Variants were cloned into pEGFP-C1 vector expressing the gene under the control of CMV promoter. The constructs express stable CEP290 protein fragments as determined by immunoblot analysis of protein extracts from transiently transfected mouse embryonic fibroblasts (FIG. 4B; see arrows). To test the functional potential of the miniCEP290s, a surrogate assay system using Cep290$^{rd16}$ MEFs (mouse embryonic fibroblasts) was used. FIG. 9 shows additional examples of CEP290 variants.

Effect of vCEP290 on Cilia Length

Figure 5A:
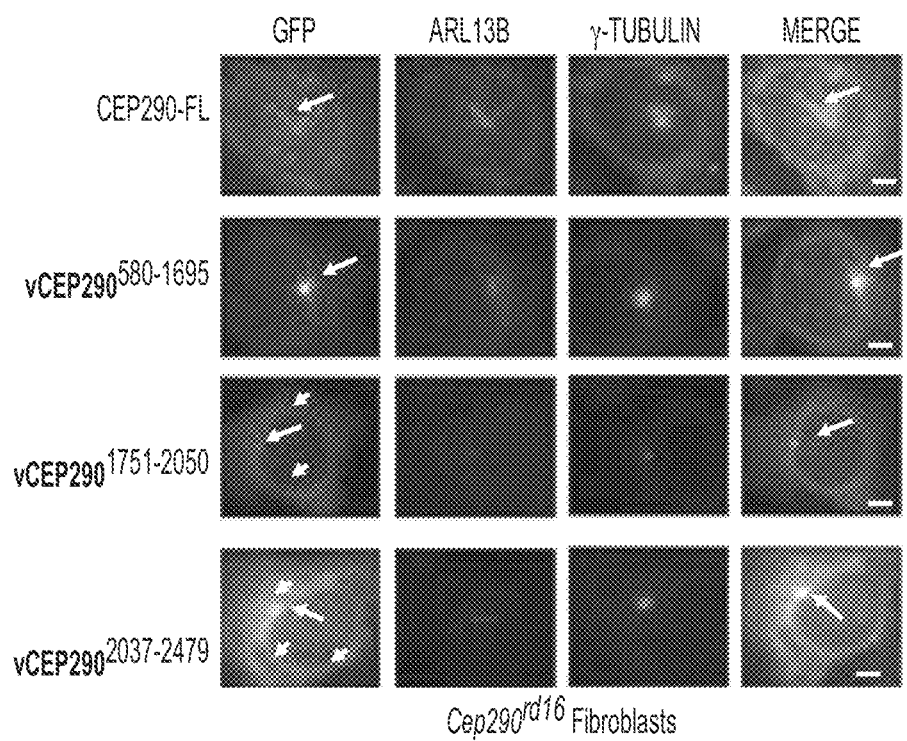
FIG. 5A shows immunostaining of Cep290$^{rd16}$ fibroblasts transiently transfected with plasmid encoding GFP-fused full-length (FL) CEP290 and indicated variants with GFP, γ-tubulin, ARL13B antibodies. Nuclei were stained with DAPI. Longer arrows indicate basal body/ciliary localization of the proteins whereas shorter arrows mark the diffuse staining.
Figure 5B:
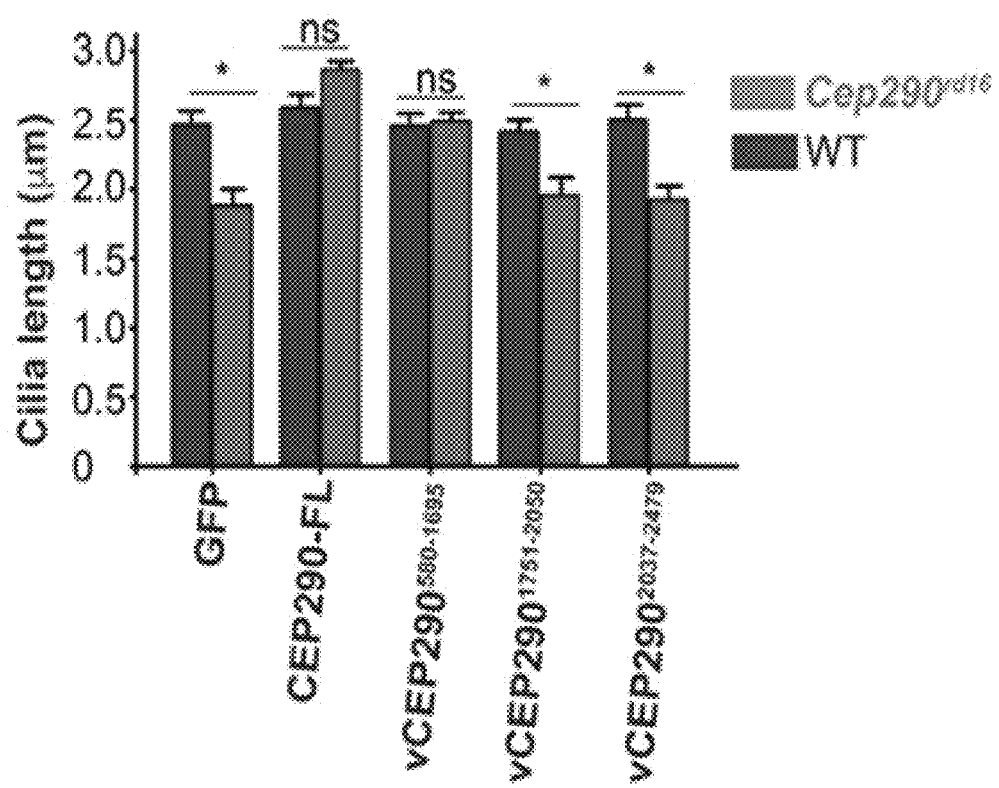
FIG. 5B shows cilia length of cells (n>200) described in FIG. 5A quantified using ImageJ. *: $p<0.001$. ns: not significant.

As shown in FIG. 5A, expression of different GFP-vCEP290-encoding plasmids into Cep290$^{rd16}$ or wild type mouse embryonic fibroblasts indicates that vCEP290$^{580-1695}$ localizes predominantly to the basal bodies (co-localization with γ-tubulin) and proximal cilia (co-localization with ADP-Ribosylation Factor-Like 13B; ARL13B; ciliary marker). Expression of other variants indicated a relatively diffuse pattern of localization. The ability of the vCEP290 to modulate cilia length in Cep290$^{rd16}$ fibroblasts was then assessed. As shown in FIG. 5B, cilia length of the mutant fibroblasts was significantly increased when vCEP290$^{580-1695}$ was expressed. Other variants, and the negative control expressing only GFP, did not reveal a change in the cilia length of the fibroblasts. No effect on cilia length of the wild type fibroblasts was observed.

Figure 6A:
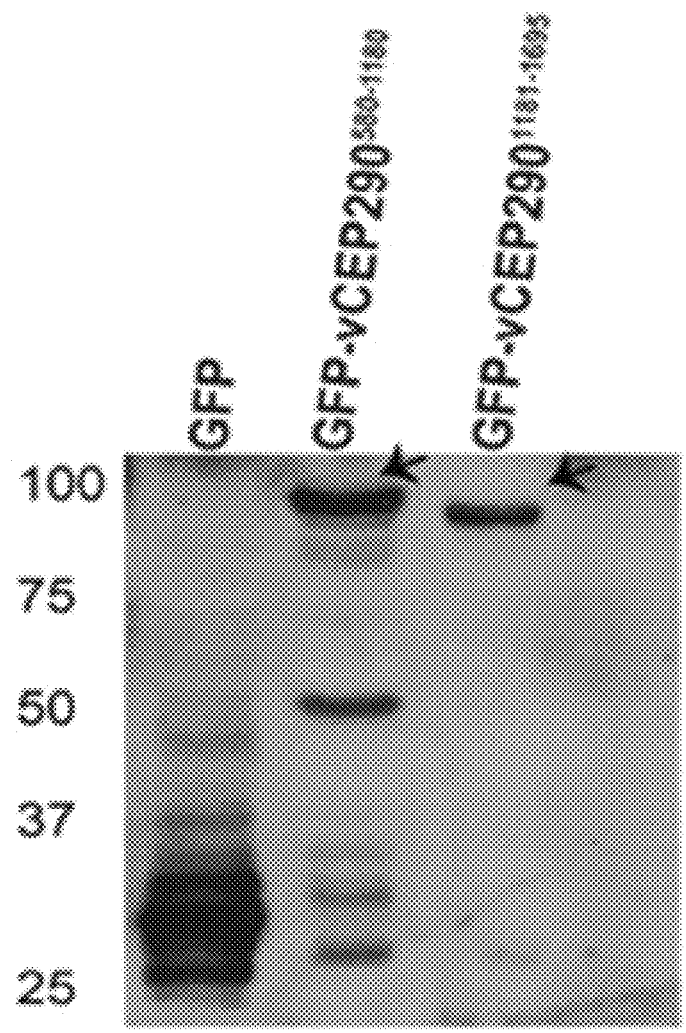
FIG. 6A shows immunoblot analysis of Cep290$^{rd16}$ fibroblasts transiently transfected with plasmid encoding GFP alone or GFP-fused indicated variants, using anti-GFP antibody. Arrows point to the expected size protein product.
Figure 6B:
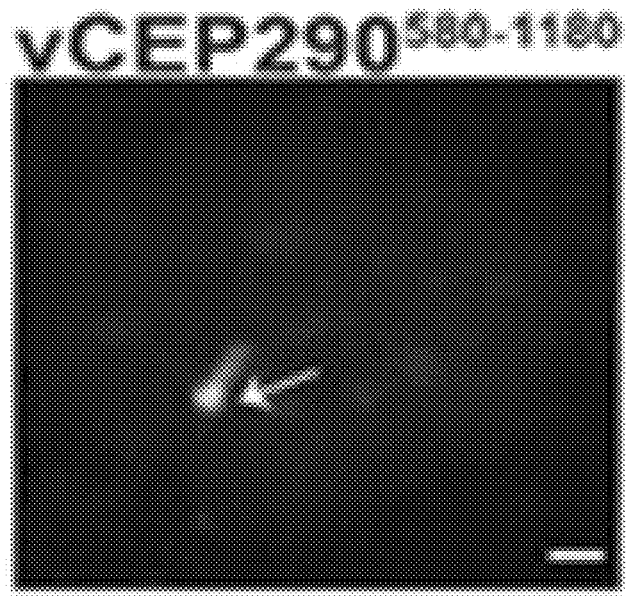
FIG. 6B shows immunostaining of the cells using GFP and ARL13B (cilia marker) antibodies. Nuclei were stained with DAPI. Arrows indicate basal body/ciliary localization of the proteins.
Figure 6B:
Figure 6C:
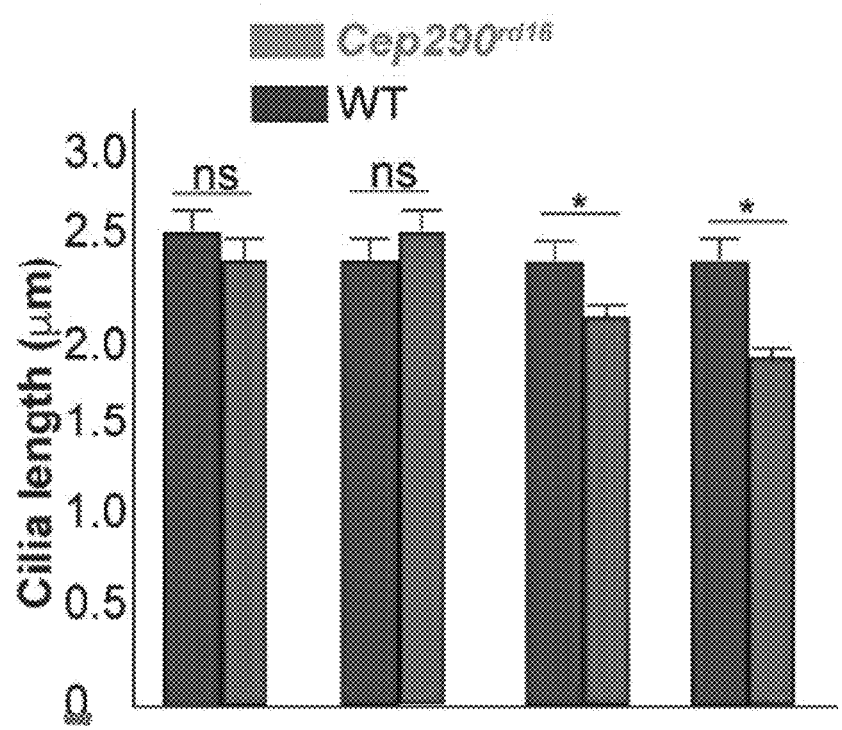
FIG. 6C shows the cilia length of the cells (n>200) quantified using ImageJ. *: p<0.001.
Figure 7A:
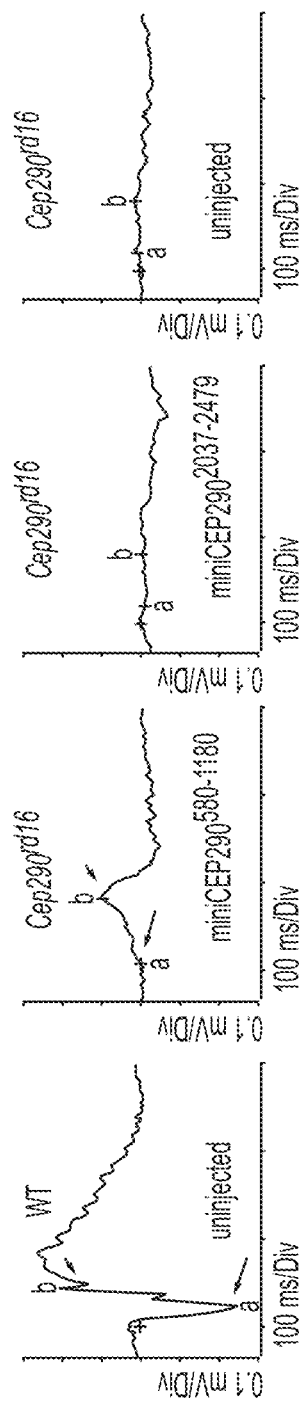
FIGS. 7A-7B show in vivo physiological rescue potential of miniCEP290$^{580-1180}$.
Figure 7B:
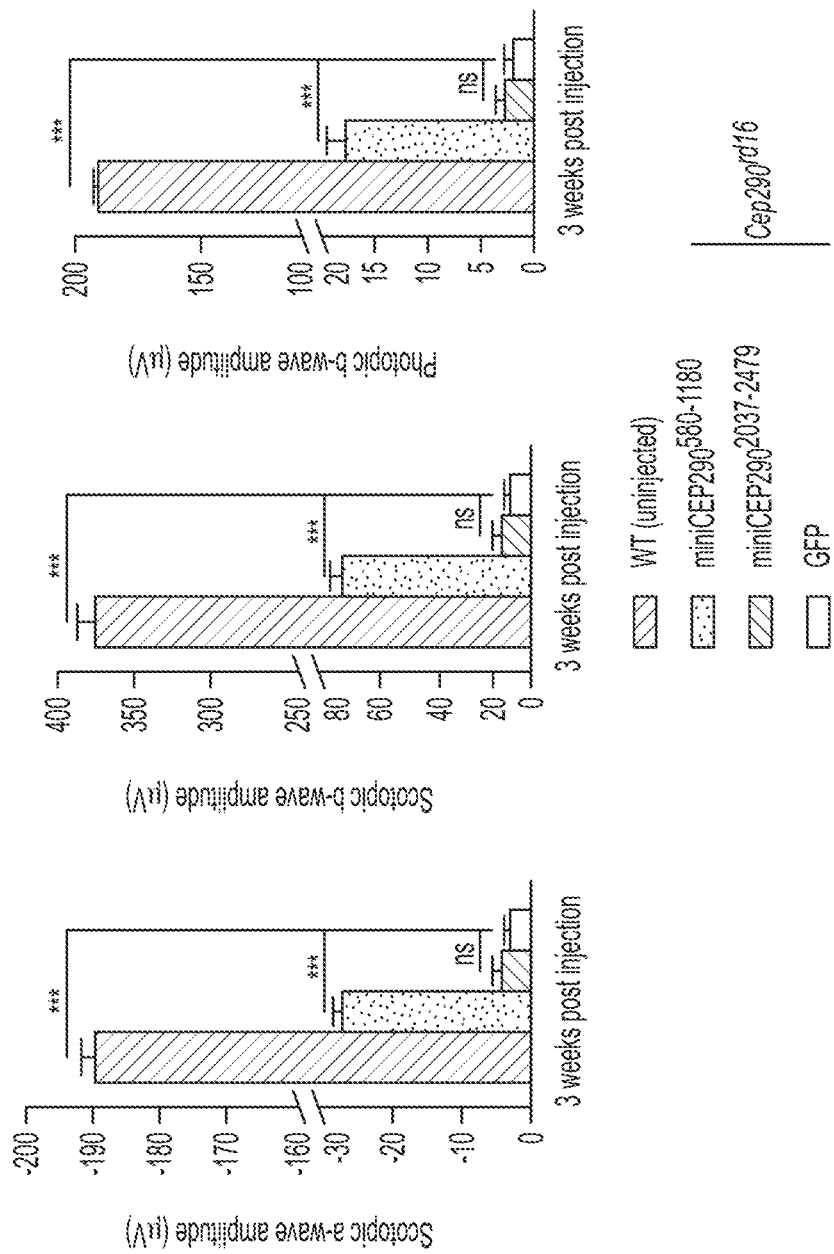
Figure 10:
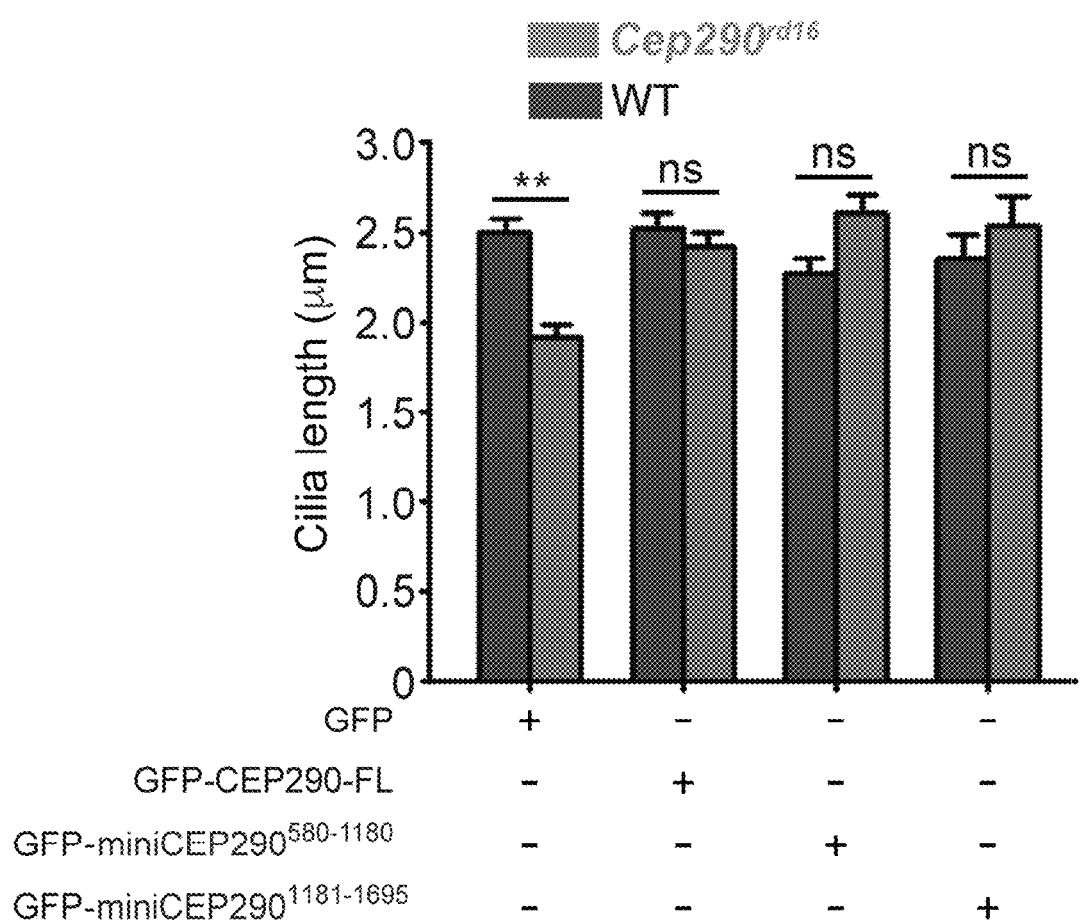
FIG. 10 shows the cilia length of Cep290$^{rd16}$ fibroblasts transiently transfected with plasmid encoding GFP alone or GFP-fused indicated variants, using anti-GFP antibody (n>200) quantified using ImageJ.
Figure 11:
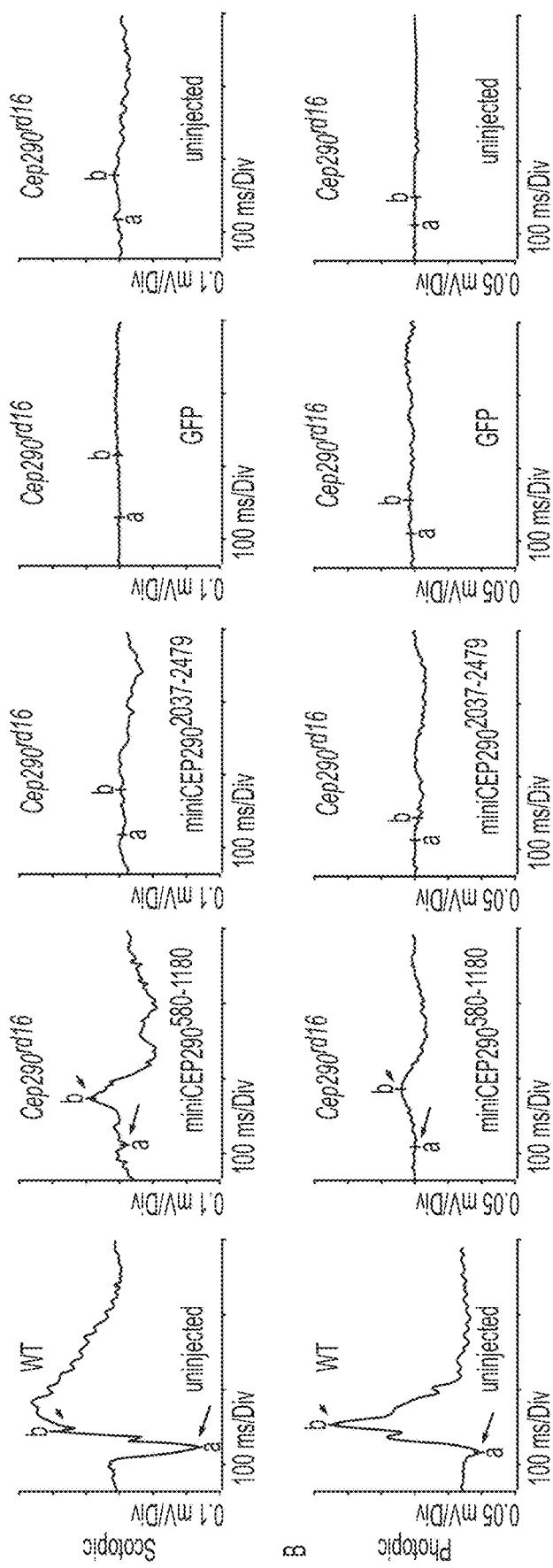
FIG. 11 shows Cep290$^{rd16}$ mice subretinally injected at P0/P1 stage with indicated miniCEP290s or GFP, and analyzed by ERG at 3 weeks post injection. Age-matched uninjected WT or Cep290$^{rd16}$ (littermates) mice were used as controls for ERG. The ERG a-wave is represented by arrows while b-wave vis depicted using arrowheads. Data represent analysis of at least 6 mice. ***: p<0.0001; ns: not significant.
Figure 12:
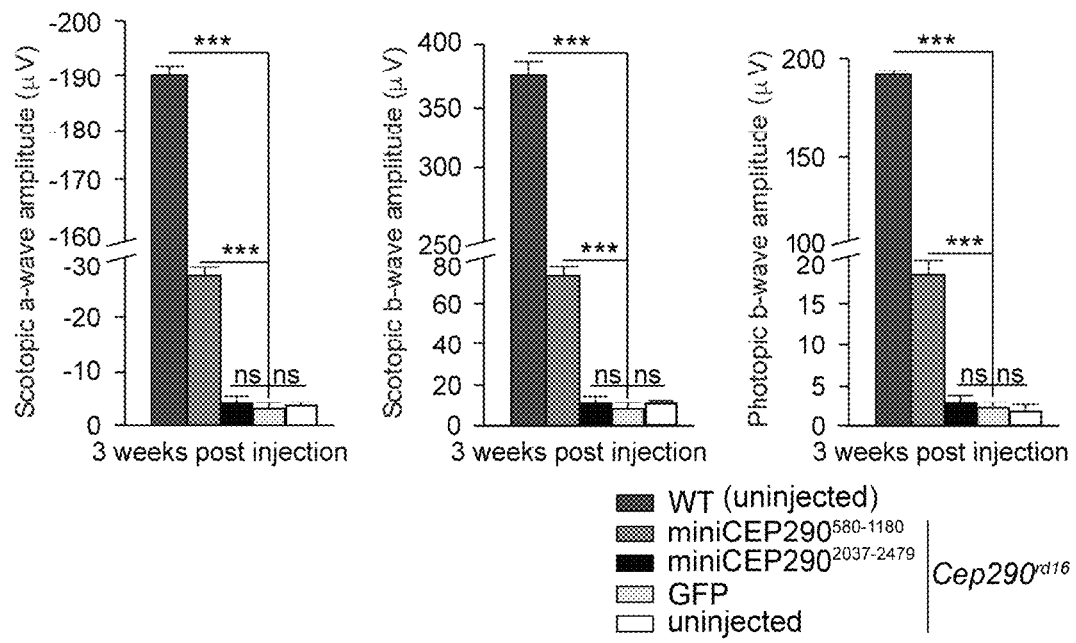
FIG. 12 shows scotopic a-wave and b-wave amplitude for mice subretinally injected at P0/P1 stage with indicated miniCEP290s or GFP, and analyzed by ERG at 3 weeks post injection Scotopic (a- and b-waves) and photopic b-wave analysis of the injected mice performed at 4 and 5 weeks post injection and compared to the ERG at 3 weeks are shown. Age-matched uninjected WT and GFP-injected Cep290$^{rd16}$ mice were used as controls.
Figure 12:
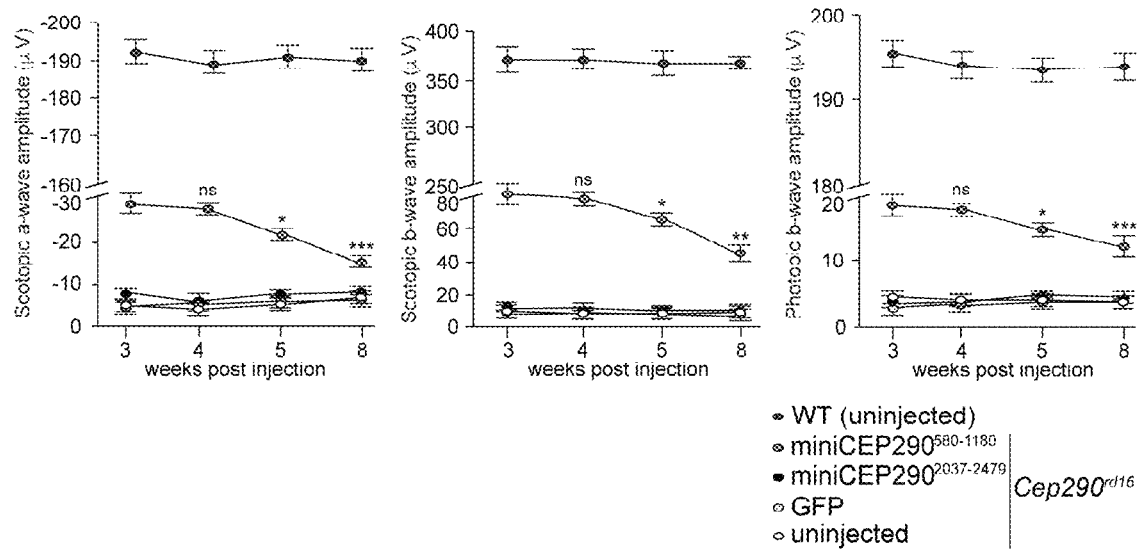

Whether further shortening vCEP290$^{580-1695}$ will result in a cilia length rescue was then investigated. Plasmids encoding GFP-fused vCEP290$^{580-1180}$ and vCEP290$^{1181-1695}$ were produced and their expression, localization and potential to rescue cilia length in Cep290$^{rd16}$ fibroblasts were tested. Both variants exhibited optimal expression as determined by immunoblotting using anti-GFP antibody, and localization to cilia (FIGS. 6A-6B). Data for vCEP290$^{1181-1695}$ indicate predominant localization to the base of cilia and diffuse staining around the basal body. Cilia rescue assay data indicate that expression of either variant results in a significant increase in the cilia length of Cep290$^{rd16}$ fibroblasts (FIG. 6C and FIG. 10).

Potential of vCEP290 In Vivo

Functionality of vCEP290 constructs in vivo was investigated. vCEP290$^{580-1180}$, vCEP290$^{1181-1695}$ and vCEP290$^{2037-2479}$ (as negative control since it did not rescue the cilia length defect in the fibroblasts) were cloned into an AAV2 vector having a CBA promoter and containing an IRES (internal ribosome entry site) between the gene of interest (e.g., vCEP290) and GFP. This permits both CEP290 and GFP to be translated from a single bicistronic mRNA and assists in identifying transduced photoreceptors using an anti-GFP antibody. Each rAAV (e.g., AAV2/8-CBA-vCep290$^{580-1180}$-IRES-GFP, AAV2/8-CBA-vCep290$^{1181-1695}$-IRES-GFP, AAV2/8-CBA-vCep290$^{2037-2472}$-IRES-GFP, and negative control AAV2/8-CBA-GFP) were injected at $8\times10^9$ vg/eye in 1 μl volume into the subretinal space of Cep290$^{rd16}$ pups at P0 stage. The mice were assessed for PR function and retinal morphology up to 5 weeks after injection.

Analysis of PR function by electroretinography (ERG) at 3 weeks post-injection revealed improvement (25-30%) in both scotopic (rod PR-mediated) and photopic (cone PR-mediated) (FIGS. 7A-7B, and FIGS. 11-12) responses of the miniCEP290$^{580-1180}$-injected mice. No improvement was detected using miniCEP290$^{2037-2479}$ or GFP. Further analysis revealed that the improvement in the ERG was stable up to 4 weeks post injection.

Figure 8A:
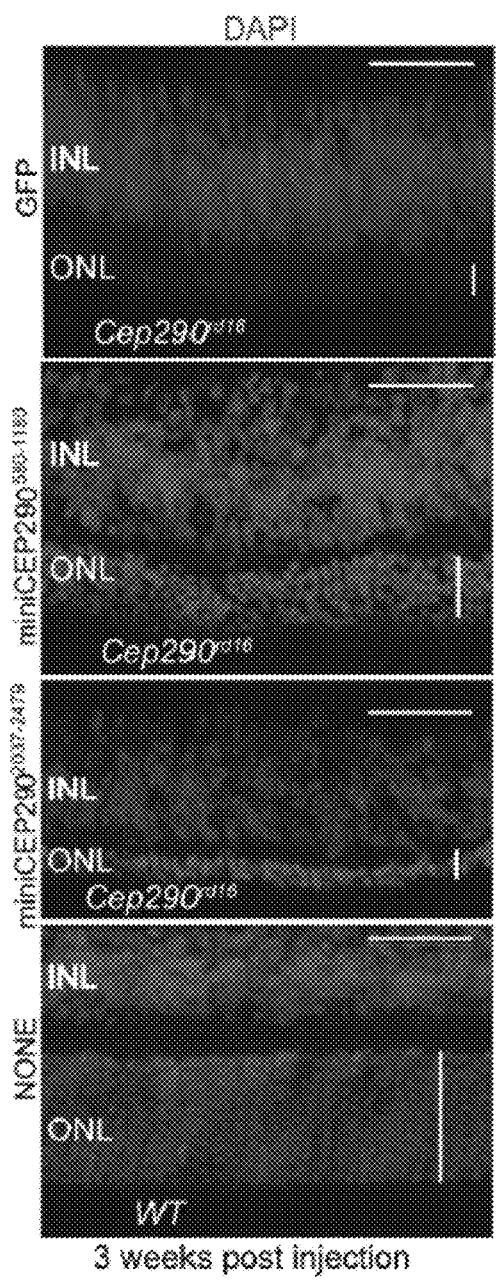
FIGS. 8A-8D show in vivo morphological rescue of photoreceptors by miniCEP290$^{580-1180}$
Figure 8B:
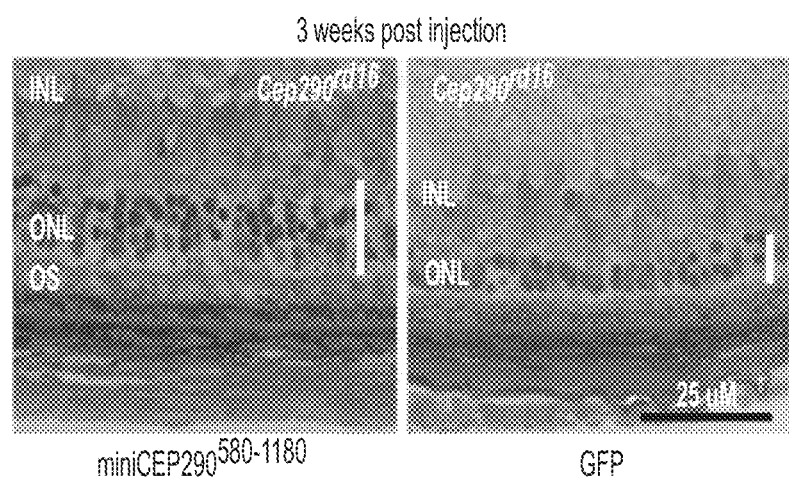

The number of layers of the ONL, which correlates with PR survival, were also counted in retinal cryosections: ~6-7 layers were observed in Cep290$^{rd16}$ retinas injected with miniCep290$^{580-1180}$; 4-5 layers were observed in Cep290$^{rd16}$ retinas injected with miniCep290$^{1181-1695}$ and 2-3 layers were observed in retinas injected with miniCep290$^{2037-2472}$ or GFP (equivalent to uninjected Cep290$^{rd16}$ at 3 weeks of age), as shown in FIG. 8A. It was also observed that ultrathin sections of the CEP290$^{rd16}$ retinas injected with miniCEP290$^{580-1180}$ exhibited significant preservation of the outer nuclear layer (ONL) (FIG. 8B).

Figure 8C:
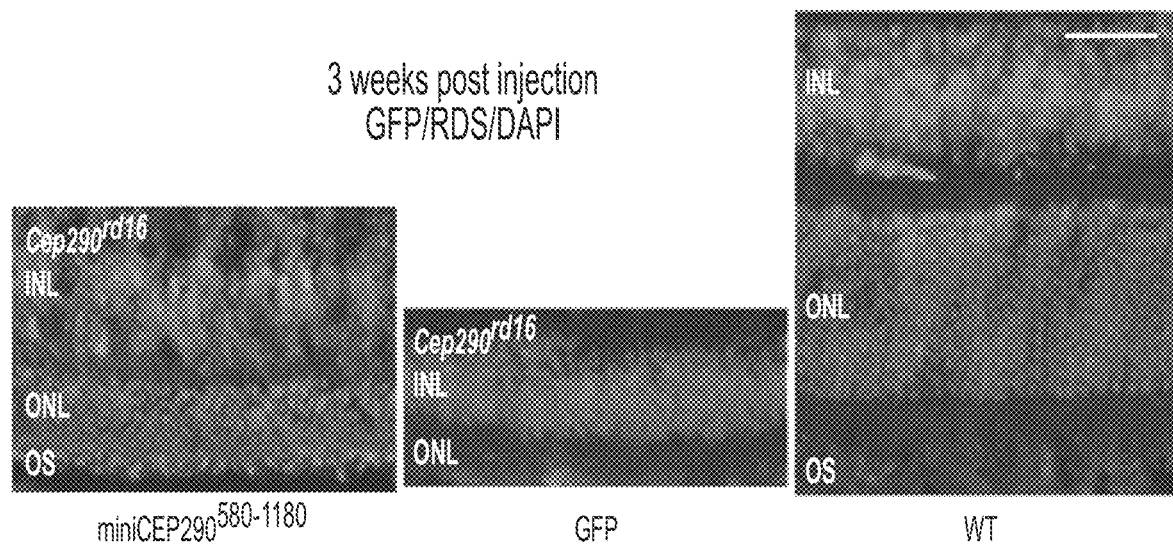
Figure 8D:
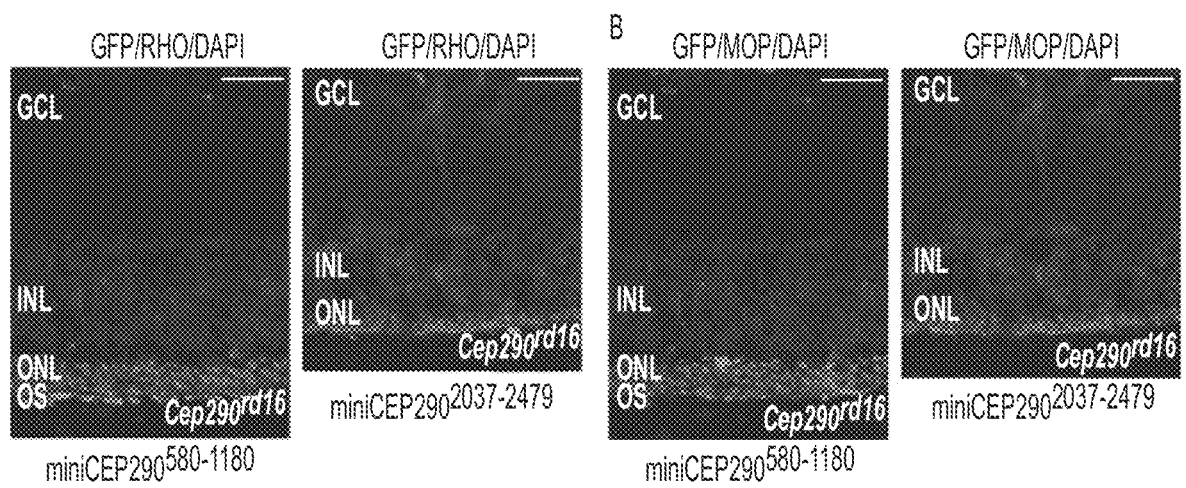

The structural preservation of photoreceptor (PR) outer segment in the miniCEP290$^{580-1180}$-injected mice was examined by staining with peripherin-RDS (retinal degeneration slow, PR outer segment marker 45). RDS is a structural protein that specifically localizes to the outer segment (OS) discs and maintains the OS structure. The miniCEP290$^{580-1180}$-injected Cep290rd16 mice exhibited improved RDS localization to the outer segment as compared to undetectable RDS expression in the GFP-injected mice (FIG. 8C). The expression of rhodopsin and cone opsins, two of the key phototransduction proteins, was also examined. Undetectable opsin expression was detected in the miniCEP290$^{2037-2479}$-injected retinas. However, the miniCEP290$^{580-1180}$-injected retinas revealed detectable expression of rhodopsin and cone opsins in the outer segments (FIG. 8D). Some staining of cone opsins in the inner segment and outer nuclear layer was also observed. Overall, the data indicate that the expression of miniCEP290$^{580-1180}$ can improve the function, morphology and opsin trafficking of CEP290$^{rd16}$ retinas.

Materials and Methods

Cell Culture, Transient Transfection and Immunostaining

MEFs derived from the WT and Cep290$^{rd16}$ mice were maintained in DMEM with 10% FBS. Transient transfection with GFP-CEP290-FL or GFP-miniCEP290s was performed using Lipofectamine 2000 (Thermo Fisher). The transfected cells were either harvested for immunoblotting or were serum-starved to induce cilia growth. The ciliated cells were then immunostained, imaged under Leica microscope (DM5500). Images were then processed for cilia length evaluation using Image J.

Constructs and AAV Production

For in vitro experiments, full-length or miniCEP290-expressing cDNAs were cloned into pEGFP-C1 plasmid expressing GFP-tagged proteins under the control of CMV promoter. For AAV production, the miniCEP290-encoding cDNAs were cloned into a pAAV2 vector plasmid between a CMVenhancer/CBA (chicken β-actin) promoter upstream of IRES (internal ribosome entry site) GFP and β-globin intron. This expression cassette was flanked with AAV2 inverted terminal repeats (ITRs). The recombinant AAV2 genomes were packaged with AAV8 capsid by HEK293-triple transfection method and purified by CsCl gradient centrifugation method.

Subretinal Injection

Wild type C57BL6/J mice were obtained from a commercial source. The Cep290$^{rd16}$ mice were also obtained. The Cep290$^{rd16}$ mouse pups (P0/P1) were subretinally injected unilaterally with $8 \times 10^9$ vg/µl (total volume 1 µl) of the virus.

ERG and Immunofluorescence Microscopy of the Retina

Scotopic and photopic ERGs were performed. For scotopic response, mice were dark adapted overnight and all procedures were performed under dim red light. Light adapted (photopic) ERGs were recorded after light adaptation with a background illumination of 30 cd/m$^2$ (white 6500 K) for 8 min.

Immunofluorescence microscopy was performed by staining retinal cryosection sections with primary antibodies: rhodopsin, M-opsin, and peripherin-RDS, ARL13B, GFP (Abcam), and γ-tubulin. After washing with PBS (phosphate buffered saline), Alexa-488 or Alexa conjugated secondary antibodies were added and the sections were further incubated for 1h. After washing, nuclei were stained with DAPI and cells were imaged using a Leica microscope (DM5500).

---

SEQUENCES

>Human CEP290 amino acid sequence; NCBI Reference Sequence: NP_079390.3

(SEQ ID NO: 1)

MPPNINWKEIMKVDPDDLPRQEELADNLLISLSKVEVNELKSEKQENVIHLFRITQSLMK

MKAQEVELALEEVEKAGEEQAKFENQLKTKVMKLENELEMAQQSAGGRDTRFLRNEI

CQLEKQLEQKDRELEDMEKELEKEKKVNEQLALRNEEAENENSKLRRENKRLKKKNE

QLCQDIIDYQKQIDSQKETLLSRRGEDSDYRSQLSKKNYELIQYLDEIQTLTEANEKIEVQ

NQEMRKNLEESVQEMEKMTDEYNRMKAIVHQTDNVIDQLKKENDHYQLQVQELTDL

LKSKNEEDDPIMVAVNAKVEEWKLILSSKDDEIIEYQQMLHNLREKLKNAQLDADKSN

VMALQQGIQERDSQIKMLTEQVEQYTKEMEKNTCIIEDLKNELQRNKGASTLSQQTHM

KIQSTLDILKEKTKEAERTAELAEADAREKDKELVEALKRLKDYESGVYGLEDAVVEIK

NCKNQIKIRDREIEILTKEINKLELKISDFLDENEALRERVGLEPKTMIDLTEFRNSKHLK

QQQYRAENQILLKEIESLEEERLDLKKKIRQMAQERGKRSATSGLTTEDLNLTENISQGD

RISERKLDLLSLKNMSEAQSKNEFLSRELIEKERDLERSRTVIAKFQNKLKELVEENKQL

EEGMKEILQAIKEMQKDPDVKGGETSLIIPSLERLVNAIESKNAEGIFDASLHLKAQVDQ

LTGRNEELRQELRESRKEAINYSQQLAKANLKIDHLEKETSLLRQSEGSNVVFKGIDLPD

GIAPSSASTINSQNEYLIHLLQELENKEKKLKNLEDSLEDYNRKFAVIRHQQSLLYKEYLS

EKETWKTESKTIKEEKRKLEDQVQQDAIKVKEYNNLLNALQMDSDEMKKILAENSRKI

TVLQVNEKSLIRQYTTLVELERQLRKENEKQKNELLSMEAEVCEKIGCLQRFKEMAIFKI

AALQKVVDNSVSLSELELANKQYNELTAKYRDILQKDNMLVQRTSNLEHLECENISLK

EQVESINKELEITKEKLHTIEQAWEQETKLGNESSMDKAKKSITNSDIVSISKKITMLEMK

ELNERQRAEHCQKMYEHLRTSLKQMEERNFELETKFAELTKINLDAQKVEQMLRDELA

| SEQUENCES |
|---|
| DSVSKAVSDADRQRILELEKNEMELKVEVSKLREISDIARRQVEILNAQQQSRDKEVESL |
| RMQLLDYQAQSDEKSLIAKLHQHNVSLQLSEATALGKLESITSKLQKMEAYNLRLEQK |
| LDEKEQALYYARLEGRNRAKHLRQTIQSLRRQFSGALPLAQQEKFSKTMIQLQNDKLKI |
| MQEMKNSQQEHRNMENKTLEMELKLKGLEELISTLKDTKGAQKVINWHMKIEELRLQ |
| ELKLNRELVKDKEEIKYLNNIISEYERTISSLEEEIVQQNKFHEERQMAWDQREVDLERQ |
| LDIFDRQQNEILNAAQKFEEATGSIPDPSLPLPNQLEIALRKIKENIRIILETRATCKSLEEK |
| LKEKESALRLAEQNILSRDKVINELRLRLPATAEREKLIAELGRKEMEPKSHHTLKIAHQ |
| TIANMQARLNQKEEVLKKYQRLLEKAREEQREIVKKHEEDLHILHHRLELQADSSLNKF |
| KQTAWDLMKQSPTPVPTNKHFIRLAEMEQTVAEQDDSLSSLLVKLKKVSQDLERQREI |
| TELKVKEFENIKLQLQENHEDEVKKVKAEVEDLKYLLDQSQKESQCLKSELQAQKEAN |
| SRAPTTTMRNLVERLKSQLALKEKQQKALSRALLELRAEMTAAAEERIISATSQKEAHL |
| NVQQIVDRHTRELKTQVEDLNENLLKLKEALKTSKNRENSLTDNLNDLNNELQKKQKA |
| YNKILREKEEIDQENDELKRQIKRLTSGLQGKPLTDNKQSLIEELQRKVKKLENQLEGK |
| VEEVDLKPMKEKNAKEELIRWEEGKKWQAKIEGIRNKLKEKEGEVFTLTKQLNTLKDL |
| FAKADKEKLTLQRKLKTTGMTVDQVLGIRALESEKELEELKKRNLDLENDILYMRAHQ |
| ALPRDSVVEDLHLQNRYLQEKLHALEKQFSKDTYSKPSISGIESDDHCQREQELQKENL |
| KLSSENIELKFQLEQANKDLPRLKNQVRDLKEMCEFLKKEKAEVQRKLGHVRGSGRSG |
| KTIPELEKTIGLMKKVVEKVQRENEQLKKASGILTSEKMANIEQENEKLKAELEKLKAH |
| LGHQLSMHYESKTKGTEKIIAENERLRKELKKETDAAEKLRIAKNNLEILNEKMTVQLE |
| ETGKRLQFAESRGPQLEGADSKSWKSIVVTRMYETKLKELETDIAKKNQSITDLKQLVK |
| EATEREQKVNKYNEDLEQQIKILKHVPEGAETEQGLKRELQVLRLANHQLDKEKAELIH |
| QIEANKDQSGAESTIPDADQLKEKIKDLETQLKMSDLEKQHLKEEIKKLKKELENFDPSF |
| FEEIEDLKYNYKEEVKKNILLEEKVKKLSEQLGVELTSPVAASEEFEDEEESPVNFPIY |
| >CEP290 Fragment (aa580-1695) amino acid sequence<br>(SEQ ID NO: 2)<br>TENISQGDRISERKLDLLSLKNMSEAQSKNEFLSRELIEKERDLERSRTVIAKFQNKLKEL |
| VEENKQLEEGMKEILQAIKEMQKDPDVKGGETSLIIPSLERLVNAIESKNAEGIFDASLH |
| LKAQVDQLTGRNEELRQELRESRKEAINYSQQLAKANLKIDHLEKETSLLRQSEGSNVV |
| FKGIDLPDGIAPSSASIINSQNEYLIHLLQELENKEKKLKNLEDSLEDYNRKFAVIRHQQS |
| LLYKEYLSEKETWKTESKTIKEEKRKLEDQVQQDAIKVKEYNNLLNALQMDSDEMKKI |
| LAENSRKITVLQVNEKSLIRQYTTLVELERQLRKENEKQKNELLSMEAEVCEKIGCLQR |
| FKEMAIFKIAALQKVVDNSVSLSELELANKQYNELTAKYRDILQKDNMLVQRTSNLEH |
| LECENISLKEQVESINKELEITKEKLHTIEQAWEQETKLGNESSMDKAKKSITNSDIVSIS |
| KKITMLEMKELNERQRAEHCQKMYEHLRTSLKQMEERNFELETKFAELTKINLDAQKV |
| EQMLRDELADSVSKAVSDADRQRILELEKNEMELKVEVSKLREISDIARRQVEILNAQQ |
| QSRDKEVESLRMQLLDYQAQSDEKSLIAKLHQHNVSLQLSEATALGKLESITSKLQKME |
| AYNLRLEQKLDEKEQALYYARLEGRNRAKHLRQTIQSLRRQFSGALPLAQQEKFSKTM |
| IQLQNDKLKIMQEMKNSQQEHRNMENKTLEMELKLKGLEELISTLKDTKGAQKVINW |
| HMKIEELRLQELKLNRELVKDKEEIKYLNNIISEYERTISSLEEEIVQQNKFHEERQMAW |
| DQREVDLERQLDIFDRQQNEILNAAQKFEEATGSIPDPSLPLPNQLEIALRKIKENIRIILET |

RATCKSLEEKLKEKESALRLAEQNILSRDKVINELRLRLPATAEREKLIAELGRKEMEPK

SHHTLKIAHQTIANMQARLNQKEEVLKKYQRLLEKAREEQREIVKKHEEDLHILHHRLE

LQADSSLNKFKQTAWDLMKQSPTPVPTNKHFIRLAEMEQTVAEQDDSLSSLLVKLKKV

SQDLERQREITELKVKEFENIKLQLQENHEDEVKKVKAEVEDLKYLLD

>CEP290 Fragment (aa580-1180) amino acid sequence
(SEQ ID NO: 3)
TENISQGDRISERKLDLLSLKNMSEAQSKNEFLSRELIEKERDLERSRTVIAKFQNKLKEL

VEENKQLEEGMKEILQAIKEMQKDPDVKGGETSLIIPSLERLVNAIESKNAEGIFDASLH

LKAQVDQLTGRNEELRQELRESRKEAINYSQQLAKANLKIDHLEKETSLLRQSEGSNVV

FKGIDLPDGIAPSSASIINSQNEYLIHLLQELENKEKKLKNLEDSLEDYNRKFAVIRHQQS

LLYKEYLSEKETWKTESKTIKEEKRKLEDQVQQDAIKVKEYNNLLNALQMDSDEMKKI

LAENSRKITVLQVNEKSLIRQYTTLVELERQLRKENEKQKNELLSMEAEVCEKIGCLQR

FKEMAIFKIAALQKVVDNSVSLSELELANKQYNELTAKYRDILQKDNMLVQRTSNLEH

LECENISLKEQVESINKELEITKEKLHTIEQAWEQETKLGNESSMDKAKKSITNSDIVSIS

KKITMLEMKELNERQRAEHCQKMYEHLRTSLKQMEERNFELETKFAELTKINLDAQKV

EQMLRDELADSVSKAVSDADRQRILELEKNEMELKVEVSKLREISDIARRQVEILNAQQ

QSRDKEV

>CEP290 Fragment (aa1181-1695) amino acid sequence
(SEQ ID NO: 4)
ESLRMQLLDYQAQSDEKSLIAKLHQHNVSLQLSEATALGKLESITSKLQKMEAYNLRLE

QKLDEKEQALYYARLEGRNRAKHLRQTIQSLRRQFSGALPLAQQEKFSKTMIQLQNDK

LKIMQEMKNSQQEHRNMENKTLEMELKLKGLEELISTLKDTKGAQKVINWHMKIEELR

LQELKLNRELVKDKEEIKYLNNIISEYERTISSLEEEIVQQNKFHEERQMAWDQREVDLE

RQLDIFDRQQNEILNAAQKFEEATGSIPDPSLPLPNQLEIALRKIKENIRIILETRATCKSLE

EKLKEKESALRLAEQNILSRDKVINELRLRLPATAEREKLIAELGRKEMEPKSHHTLKIA

HQTIANMQARLNQKEEVLKKYQRLLEKAREEQREIVKKHEEDLHILHHRLELQADSSL

NKFKQTAWDLMKQSPTPVPTNKHFIRLAEMEQTVAEQDDSLSSLLVKLKKVSQDLERQ

REITELKVKEFENIKLQLQENHEDEVKKVKAEVEDLKYLLD

>CEP290 Fragment (aa580-1695) nucleic acid sequence
(SEQ ID NO: 5)
ACTGAAAACATTTCTCAAGGAGATAGAATAAGTGAAAGAAAATTGGATTTATTGAG

CCTCAAAAATATGAGTGAAGCACAATCAAAGAATGAATTTCTTTCAAGAGAACTAA

TTGAAAAAGAAAGAGATTTAGAAAGGAGTAGGACAGTGATAGCCAAATTTCAGAA

TAAATTAAAAGAATTAGTTGAAGAAAATAAGCAACTTGAAGAAGGTATGAAAGAA

ATATTGCAAGCAATTAAGGAAATGCAGAAAGATCCTGATGTTAAAGGAGGAGAAA

CATCTCTAATTATCCCTAGCCTTGAAAGACTAGTTAATGCTATAGAATCAAAGAATG

CAGAAGGAATCTTTGATGCGAGTCTGCATTTGAAAGCCCAAGTTGATCAGCTTACC

GGAAGAAATGAAGAATTAAGACAGGAGCTCAGGGAATCTCGGAAAGAGGCTATAA

ATTATTCACAGCAGTTGGCAAAAGCTAATTTAAAGATAGACCATCTTGAAAAAGAA

ACTAGTCTTTTACGACAATCAGAAGGATCGAATGTTGTTTTTAAAGGAATTGACTTA

CCTGATGGGATAGCACCATCTAGTGCCAGTATCATTAATTCTCAGAATGAATATTTA

-continued

| SEQUENCES |
|---|
| ATACATTTGTTACAGGAACTAGAAAATAAAGAAAAAAAGTTAAAGAATTTAGAAG |
| ATTCTCTTGAAGATTACAACAGAAAATTTGCTGTAATTCGTCATCAACAAAGTTTGT |
| TGTATAAAGAATACCTAAGTGAAAAGGAGACCTGGAAAACAGAATCTAAAACAAT |
| AAAAGAGGAAAAGAGAAAACTTGAGGATCAAGTCCAACAAGATGCTATAAAAGTA |
| AAAGAATATAATAATTTGCTCAATGCTCTTCAGATGGATTCGGATGAAATGAAAAA |
| AATACTTGCAGAAAATAGTAGGAAAATTACTGTTTTGCAAGTGAATGAAAATCAC |
| TTATAAGGCAATATACAACCTTAGTAGAATTGGAGCGACAACTTAGAAAAGAAAT |
| GAGAAGCAAAAGAATGAATTGTTGTCAATGGAGGCTGAAGTTTGTGAAAAAATTGG |
| GTGTTTGCAAAGATTTAAGGAAATGGCCATTTTCAAGATTGCAGCTCTCCAAAAAGT |
| TGTAGATAATAGTGTTTCTTTGTCTGAACTAGAACTGGCTAATAAACAGTACAATGA |
| ACTGACTGCTAAGTACAGGGACATCTTGCAAAAAGATAATATGCTTGTTCAAAGAA |
| CAAGTAACTTGGAACACCTGGAGTGTGAAAACATCTCCTTAAAAGAACAAGTGGAG |
| TCTATAAATAAAGAACTGGAGATTACCAAGGAAAAACTTCACACTATTGAACAAGC |
| CTGGGAACAGGAAACTAAATTAGGTAATGAATCTAGCATGGATAAGGCAAAGAAA |
| TCAATAACCAACAGTGACATTGTTTCCATTTCAAAAAAAATAACTATGCTGGAAAT |
| GAAGGAATTAAATGAAAGGCAGCGGGCTGAACATTGTCAAAAAATGTATGAACAC |
| TTACGGACTTCGTTAAAGCAAATGGAGGAACGTAATTTTGAATTGGAAACCAAATT |
| TGCTGAGCTTACCAAAATCAATTTGGATGCACAGAAGGTGGAACAGATGTTAAGAG |
| ATGAATTAGCTGATAGTGTGAGCAAGGCAGTAAGTGATGCTGATAGGCAACGGATT |
| CTAGAATTAGAGAAGAATGAAATGGAACTAAAAGTTGAAGTGTCAAAACTGAGAG |
| AGATTTCTGATATTGCCAGAAGACAAGTTGAAATTTTGAATGCACAACAACAATCT |
| AGGGACAAGGAAGTAACTGAAAACATTTCTCAAGGAGATAGAATAAGTGAAAGAA |
| AATTGGATTTATTGAGCCTCAAAAATATGAGTGAAGCACAATCAAAGAATGAATTT |
| CTTTCAAGAACTAATTGAAAAAGAAAGAGATTTAGAAAGGAGTAGGACAGTGA |
| TAGCCAAATTTCAGAATAAATTAAAAGAATTAGTTGAAGAAAATAAGCAACTTGAA |
| GAAGGTATGAAAGAAATATTGCAAGCAATTAAGGAAATGCAGAAAGATCCTGATG |
| TTAAAGGAGGAGAAACATCTCTAATTATCCCTAGCCTTGAAAGACTAGTTAATGCT |
| ATAGAATCAAAGAATGCAGAAGGAATCTTTGATGCGAGTCTGCATTTGAAAGCCCA |
| AGTTGATCAGCTTACCGGAAGAAATGAAGAATTAAGACAGGAGCTCAGGGAATCTC |
| GGAAAGAGGCTATAAATTATTCACAGCAGTTGGCAAAAGCTAATTTAAAGATAGAC |
| CATCTTGAAAAAGAAACTAGTCTTTTACGACAATCAGAAGGATCGAATGTTGTTTTT |
| AAAGGAATTGACTTACCTGATGGGATAGCACCATCTAGTGCCAGTATCATTAATTCT |
| CAGAATGAATATTTAATACATTTGTTACAGGAACTAGAAAATAAAGAAAAAAAGTT |
| AAAGAATTTAGAAGATTCTCTTGAAGATTACAACAGAAAATTTGCTGTAATTCGTCA |
| TCAACAAAGTTTGTTGTATAAAGAATACCTAAGTGAAAAGGAGACCTGGAAAACAG |
| AATCTAAAACAATAAAAGAGGAAAAGAGAAAACTTGAGGATCAAGTCCAACAAGA |
| TGCTATAAAAGTAAAAGAATATAATAATTTGCTCAATGCTCTTCAGATGGATTCGGA |
| TGAAATGAAAAAAATACTTGCAGAAAATAGTAGGAAAATTACTGTTTTGCAAGTGA |
| ATGAAAAATCACTTATAAGGCAATATACAACCTTAGTAGAATTGGAGCGACAACTT |

| SEQUENCES |
| --- |
| AGAAAAGAAAATGAGAAGCAAAAGAATGAATTGTTGTCAATGGAGGCTGAAGTTT |
| GTGAAAAAATTGGGTGTTTGCAAAGATTTAAGGAAATGGCCATTTTCAAGATTGCA |
| GCTCTCCAAAAAGTTGTAGATAATAGTGTTTCTTTGTCTGAACTAGAACTGGCTAAT |
| AAACAGTACAATGAACTGACTGCTAAGTACAGGGACATCTTGCAAAAAGATAATAT |
| GCTTGTTCAAAGAACAAGTAACTTGGAACACCTGGAGTGTGAAAACATCTCCTTAA |
| AAGAACAAGTGGAGTCTATAAATAAAGAACTGGAGATTACCAAGGAAAAACTTCA |
| CACTATTGAACAAGCCTGGGAACAGGAAACTAAATTAGGTAATGAATCTAGCATGG |
| ATAAGGCAAAGAAATCAATAACCAACAGTGACATTGTTTCCATTTCAAAAAAAATA |
| ACTATGCTGGAAATGAAGGAATTAAATGAAAGGCAGCGGGCTGAACATTGTCAAA |
| AAATGTATGAACACTTACGGACTTCGTTAAAGCAAATGGAGGAACGTAATTTTGAA |
| TTGGAAACCAAATTTGCTGAGCTTACCAAAATCAATTTGGATGCACAGAAGGTGGA |
| ACAGATGTTAAGAGATGAATTAGCTGATAGTGTGAGCAAGGCAGTAAGTGATGCTG |
| ATAGGCAACGGATTCTAGAATTAGAGAAGAATGAAATGGAACTAAAAGTTGAAGT |
| GTCAAAACTGAGAGAGATTTCTGATATTGCCAGAAGACAAGTTGAAATTTTGAATG |
| CACAACAACAATCTAGGGACAAGGAAGTA |

>CEP290 Fragment (aa580-1180) nucleic acid sequence
(SEQ ID NO: 6)
ACTGAAAACATTTCTCAAGGAGATAGAATAAGTGAAAGAAAATTGGATTTATTGAG
CCTCAAAAATATGAGTGAAGCACAATCAAAGAATGAATTTCTTTCAAGAGAACTAA
TTGAAAAAGAAAGAGATTTAGAAAGGAGTAGGACAGTGATAGCCAAATTTCAGAA
TAAATTAAAAGAATTAGTTGAAGAAAATAAGCAACTTGAAGAAGGTATGAAAGAA
ATATTGCAAGCAATTAAGGAAATGCAGAAAGATCCTGATGTTAAAGGAGGAGAAA
CATCTCTAATTATCCCTAGCCTTGAAAGACTAGTTAATGCTATAGAATCAAAGAATG
CAGAAGGAATCTTTGATGCGAGTCTGCATTTGAAAGCCCAAGTTGATCAGCTTACC
GGAAGAAATGAAGAATTAAGACAGGAGCTCAGGGAATCTCGGAAAGAGGCTATAA
ATTATTCACAGCAGTTGGCAAAAGCTAATTTAAAGATAGACCATCTTGAAAAAGAA
ACTAGTCTTTTACGACAATCAGAAGGATCGAATGTTGTTTTTAAAGGAATTGACTTA
CCTGATGGGATAGCACCATCTAGTGCCAGTATCATTAATTCTCAGAATGAATATTTA
ATACATTTGTTACAGGAACTAGAAAATAAAGAAAAAAAGTTAAAGAATTTAGAAG
ATTCTCTTGAAGATTACAACAGAAAATTTGCTGTAATTCGTCATCAACAAAGTTTGT
TGTATAAAGAATACCTAAGTGAAAAGGAGACCTGGAAAACAGAATCTAAAACAAT
AAAAGAGGAAAAGAGAAAACTTGAGGATCAAGTCCAACAAGATGCTATAAAAGTA
AAAGAATATAATAATTTGCTCAATGCTCTTCAGATGGATTCGGATGAAATGAAAAA
AATACTTGCAGAAAATAGTAGGAAAATTACTGTTTTGCAAGTGAATGAAAATCAC
TTATAAGGCAATATACAACCTTAGTAGAATTGGAGCGACAACTTAGAAAAGAAAT
GAGAAGCAAAAGAATGAATTGTTGTCAATGGAGGCTGAAGTTTGTGAAAAAATTGG
GTGTTTGCAAAGATTTAAGGAAATGGCCATTTTCAAGATTGCAGCTCTCCAAAAAGT
TGTAGATAATAGTGTTTCTTTGTCTGAACTAGAACTGGCTAATAAACAGTACAATGA
ACTGACTGCTAAGTACAGGGACATCTTGCAAAAAGATAATATGCTTGTTCAAAGAA

| SEQUENCES |
| --- |
| CAAGTAACTTGGAACACCTGGAGTGTGAAAACATCTCCTTAAAAGAACAAGTGGAG |
| TCTATAAATAAAGAACTGGAGATTACCAAGGAAAAACTTCACACTATTGAACAAGC |
| CTGGGAACAGGAAACTAAATTAGGTAATGAATCTAGCATGGATAAGGCAAAGAAA |
| TCAATAACCAACAGTGACATTGTTTCCATTTCAAAAAAATAACTATGCTGGAAAT |
| GAAGGAATTAAATGAAAGGCAGCGGGCTGAACATTGTCAAAAAATGTATGAACAC |
| TTACGGACTTCGTTAAAGCAAATGGAGGAACGTAATTTTGAATTGGAAACCAATT |
| TGCTGAGCTTACCAAAATCAATTTGGATGCACAGAAGGTGGAACAGATGTTAAGAG |
| ATGAATTAGCTGATAGTGTGAGCAAGGCAGTAAGTGATGCTGATAGGCAACGGATT |
| CTAGAATTAGAGAAGAATGAAATGGAACTAAAAGTTGAAGTGTCAAAACTGAGAG |
| AGATTTCTGATATTGCCAGAAGACAAGTTGAAATTTTGAATGCACAACAACAATCT |
| AGGGACAAGGAAGTA |
| >CEP290 Fragment (aa1181-1695) nucleic acid sequence (SEQ ID NO: 7) GAGTCCCTCAGAATGCAACTGCTAGACTATCAGGCACAGTCTGATGAAAAGTCGCT |
| CATTGCCAAGTTGCACCAACATAATGTCTCTCTTCAACTGAGTGAGGCTACTGCTCT |
| TGGTAAGTTGGAGTCAATTACATCTAAACTGCAGAAGATGGAGGCCTACAACTTGC |
| GCTTAGAGCAGAAACTTGATGAAAAAGAACAGGCTCTCTATTATGCTCGTTTGGAG |
| GGAAGAAACAGAGCAAAACATCTGCGCCAAACAATTCAGTCTCTACGACGACAGTT |
| TAGTGGAGCTTTACCCTTGGCACAACAGGAAAAGTTCTCCAAAACAATGATTCAAC |
| TACAAAATGACAAACTTAAGATAATGCAAGAAATGAAAAATTCTCAACAAGAACAT |
| AGAAATATGGAGAACAAAACATTGGAGATGGAATTAAAATTAAAGGGCCTGGAAG |
| AGTTAATAAGCACTTTAAAGGATACCAAAGGAGCCCAAAAGGTAATCAACTGGCAT |
| ATGAAAATAGAAGAACTTCGTCTTCAAGAACTTAAACTAAATCGGGAATTAGTCAA |
| GGATAAAGAAGAAATAAAATATTTGAATAACATAATTTCTGAATATGAACGTACAA |
| TCAGCAGTCTTGAAGAAGAAATTGTGCAACAGAACAAGTTTCATGAAGAAAGACAA |
| ATGGCCTGGGATCAAAGAGAAGTTGACCTGGAACGCCAACTAGACATTTTTGACCG |
| TCAGCAAAATGAAATACTAAATGCGGCACAAAAGTTTGAAGAAGCTACAGGATCA |
| ATCCCTGACCCTAGTTTGCCCCTTCCAAATCAACTTGAGATCGCTCTAAGGAAAATT |
| AAGGAGAACATTCGAATAATTCTAGAAACACGGGCAACTTGCAAATCACTAGAAGA |
| GAAACTAAAAGAGAAAGAATCTGCTTTAAGGTTAGCAGAACAAAATATACTGTCAA |
| GAGACAAAGTAATCAATGAACTGAGGCTTCGATTGCCTGCCACTGCAGAAAGAGAA |
| AAGCTCATAGCTGAGCTAGGCAGAAAAGAGATGGAACCAAAATCTCACCACACATT |
| GAAAATTGCTCATCAAACCATTGCAAACATGCAAGCAAGGTTAAATCAAAAGAAG |
| AAGTATTAAAGAAGTATCAACGTCTTCTAGAAAAAGCCAGAGAGGAGCAAAGAGA |
| AATTGTGAAGAAACATGAGGAAGACCTTCATATTCTTCATCACAGATTAGAACTAC |
| AGGCTGATAGTTCACTAAATAAATTCAAACAAACGGCTTGGGATTTAATGAAACAG |
| TCTCCCACTCCAGTTCCTACCAACAAGCATTTTATTCGTCTGGCTGAGATGGAACAG |
| ACAGTAGCAGAACAAGATGACTCTCTTTCCTCACTCTTGGTCAAACTAAAGAAAGT |
| ATCACAAGATTTGGAGAGACAAAGAGAAATCACTGAATTAAAAGTAAAAGAATTT |

| SEQUENCES |
| --- |
| GAAAATATCAAATTACAGCTTCAAGAAAACCATGAAGATGAAGTGAAAAAAGTAA |
| AAGCGGAAGTAGAGGATTTAAAGTATCTTCTGGAC |
| >CEP290 nucleic acid sequence; NCBI Reference Sequence: NM_025114.3<br>(SEQ ID NO: 8) |
| ATTTGAAGTCCTCGTTCCACGCCTTCTCATCATCCTGAACACCGAGCTCTGGGACTC |
| CGGCGGAGAATCTAAACGTAAAGCATCACCCACGGTCGTGAACTGTAGGCTCTCCT |
| GGCATCCGGGATCTTATTCTGGCCTTGGCGGAGTTGGGGATGGTGTCGCCTAGCAGC |
| CGCTGCCGCTTTGGCTTGCTCGGGACCATTTGGCTGGACCCAGAGTCCGCGTGGAAC |
| CGCGATAGGGATCTGTCAGGGCCCGCGGCCGGGTCCAGCTTGGTGGTTGCGGTAGT |
| GAGAGGCCTCCGCTGGTTGCCAGGCTTGGTCTAGAGGTGGAGCACAGTGAAAGAAT |
| TCAAGATGCCACCTAATATAAACTGGAAAGAAATAATGAAAGTTGACCCAGATGAC |
| CTGCCCCGTCAAGAAGAACTGGCAGATAATTTATTGATTTCCTTATCCAAGGTGGAA |
| GTAAATGAGCTAAAAAGTGAAAAGCAAGAAAATGTGATACACCTTTTCAGAATTAC |
| TCAGTCACTAATGAAGATGAAAGCTCAAGAAGTGGAGCTGGCTTTGGAAGAAGTAG |
| AAAAAGCTGGAGAAGAACAAGCAAAATTTGAAAATCAATTAAAAACTAAAGTAAT |
| GAAACTGGAAAATGAACTGGAGATGGCTCAGCAGTCTGCAGGTGGACGAGATACTC |
| GGTTTTTACGTAATGAAATTTGCCAACTTGAAAAACAATTAGAACAAAAAGATAGA |
| GAATTGGAGGACATGGAAAAGGAGTTGGAGAAAGAGAAGAAAGTTAATGAGCAAT |
| TGGCTCTTCGAAATGAGGAGGCAGAAAATGAAAACAGCAAATTAAGAAGAGAGAA |
| CAAACGTCTAAAGAAAAAGAATGAACAACTTTGTCAGGATATTATTGACTACCAGA |
| AACAAATAGATTCACAGAAAGAAACACTTTTATCAAGAAGAGGGGAAGACAGTGA |
| CTACCGATCACAGTTGTCTAAAAAAAACTATGAGCTTATCCAATATCTTGATGAAAT |
| TCAGACTTTAACAGAAGCTAATGAGAAAATTGAAGTTCAGAATCAAGAAATGAGAA |
| AAAATTTAGAAGAGTCTGTACAGGAAATGGAGAAGATGACTGATGAATATAATAG |
| AATGAAAGCTATTGTGCATCAGACAGATAATGTAATAGATCAGTTAAAAAAAGAAA |
| ACGATCATTATCAACTTCAAGTGCAGGAGCTTACAGATCTTCTGAAATCAAAAAAT |
| GAAGAAGATGATCCAATTATGGTAGCTGTCAATGCAAAAGTAGAAGAATGGAAGCT |
| AATTTTGTCTTCTAAAGATGATGAAATTATTGAGTATCAGCAAATGTTACATAACCT |
| AAGGGAGAAACTTAAGAATGCTCAGCTTGATGCTGATAAAAGTAATGTTATGGCTC |
| TACAGCAGGGTATACAGGAACGAGACAGTCAAATTAAGATGCTCACCGAACAAGT |
| AGAACAATATACAAAAGAAATGGAAAAGAATACTTGTATTATTGAAGATTTGAAAA |
| ATGAGCTCCAAAGAAACAAAGGTGCTTCAACCCTTTCTCAACAGACTCATATGAAA |
| ATTCAGTCAACGTTAGACATTTTAAAAGAGAAAACTAAAGAGGCTGAGAGAACAGC |
| TGAACTGGCTGAGGCTGATGCTAGGGAAAAGGATAAAGAATTAGTTGAGGCTCTGA |
| AGAGGTTAAAAGATTATGAATCGGGAGTATATGGTTTAGAAGATGCTGTCGTTGAA |
| ATAAAGAATTGTAAAAACCAAATTAAAATAAGAGATCGAGAGATTGAAATATTAAC |
| AAAGGAAATCAATAAACTTGAATTGAAGATCAGTGATTTCCTTGATGAAAATGAGG |
| CACTTAGAGAGCGTGTGGGCCTTGAACCAAAGACAATGATTGATTTAACTGAATTT |
| AGAAATAGCAAACACTTAAAACAGCAGCAGTACAGAGCTGAAAACCAGATTCTTTT |

| SEQUENCES |
| --- |
| GAAAGAGATTGAAAGTCTAGAGGAAGAACGACTTGATCTGAAAAAAAAATTCGT |
| CAAATGGCTCAAGAAAGAGGAAAAAGAAGTGCAACTTCAGGATTAACCACTGAGG |
| ACCTGAACCTAACTGAAAACATTTCTCAAGGAGATAGAATAAGTGAAAGAAAATTG |
| GATTTATTGAGCCTCAAAAATATGAGTGAAGCACAATCAAAGAATGAATTTCTTTC |
| AAGAGAACTAATTGAAAAGAAAGAGATTTAGAAAGGAGTAGGACAGTGATAGCC |
| AAATTTCAGAATAAATTAAAAGAATTAGTTGAAGAAAATAAGCAACTTGAAGAAG |
| GTATGAAAGAAATATTGCAAGCAATTAAGGAAATGCAGAAAGATCCTGATGTTAAA |
| GGAGGAGAAACATCTCTAATTATCCCTAGCCTTGAAAGACTAGTTAATGCTATAGA |
| ATCAAAGAATGCAGAAGGAATCTTTGATGCGAGTCTGCATTTGAAAGCCCAAGTTG |
| ATCAGCTTACCGGAAGAAATGAAGAATTAAGACAGGAGCTCAGGGAATCTCGGAA |
| AGAGGCTATAAATTATTCACAGCAGTTGGCAAAAGCTAATTTAAAGATAGACCATC |
| TTGAAAAGAAACTAGTCTTTTACGACAATCAGAAGGATCGAATGTTGTTTTTAAA |
| GGAATTGACTTACCTGATGGGATAGCACCATCTAGTGCCAGTATCATTAATTCTCAG |
| AATGAATATTTAATACATTTGTTACAGGAACTAGAAAATAAAGAAAAAAAGTTAAA |
| GAATTTAGAAGATTCTCTTGAAGATTACAACAGAAAATTTGCTGTAATTCGTCATCA |
| ACAAAGTTTGTTGTATAAAGAATACCTAAGTGAAAAGGAGACCTGGAAAACAGAAT |
| CTAAAACAATAAAAGAGGAAAAGAGAAAACTTGAGGATCAAGTCCAACAAGATGC |
| TATAAAAGTAAAAGAATATAATAATTTGCTCAATGCTCTTCAGATGGATTCGGATG |
| AAATGAAAAAAATACTTGCAGAAAATAGTAGGAAAATTACTGTTTTGCAAGTGAAT |
| GAAAAATCACTTATAAGGCAATATACAACCTTAGTAGAATTGGAGCGACAACTTAG |
| AAAAGAAAATGAGAAGCAAAAGAATGAATTGTTGTCAATGGAGGCTGAAGTTTGT |
| GAAAAAATTGGGTGTTTGCAAAGATTTAAGGAAATGGCCATTTTCAAGATTGCAGC |
| TCTCCAAAAAGTTGTAGATAATAGTGTTTCTTTGTCTGAACTAGAACTGGCTAATAA |
| ACAGTACAATGAACTGACTGCTAAGTACAGGGACATCTTGCAAAAAGATAATATGC |
| TTGTTCAAAGAACAAGTAACTTGGAACACCTGGAGTGTGAAAACATCTCCTTAAAA |
| GAACAAGTGGAGTCTATAAATAAAGAACTGGAGATTACCAAGGAAAAACTTCACA |
| CTATTGAACAAGCCTGGGAACAGGAAACTAAATTAGGTAATGAATCTAGCATGGAT |
| AAGGCAAAGAAATCAATAACCAACAGTGACATTGTTTCCATTTCAAAAAAAATAAC |
| TATGCTGGAAATGAAGGAATTAAATGAAAGGCAGCGGGCTGAACATTGTCAAAAA |
| ATGTATGAACACTTACGGACTTCGTTAAAGCAAATGGAGGAACGTAATTTTGAATT |
| GGAAACCAAATTTGCTGAGCTTACCAAAATCAATTTGGATGCACAGAAGGTGGAAC |
| AGATGTTAAGAGATGAATTAGCTGATAGTGTGAGCAAGGCAGTAAGTGATGCTGAT |
| AGGCAACGGATTCTAGAATTAGAGAAGAATGAAATGGAACTAAAAGTTGAAGTGT |
| CAAAACTGAGAGAGATTTCTGATATTGCCAGAAGACAAGTTGAAATTTTGAATGCA |
| CAACAACAATCTAGGGACAAGGAAGTAGAGTCCCTCAGAATGCAACTGCTAGACTA |
| TCAGGCACAGTCTGATGAAAAGTCGCTCATTGCCAAGTTGCACCAACATAATGTCTC |
| TCTTCAACTGAGTGAGGCTACTGCTCTTGGTAAGTTGGAGTCAATTACATCTAAACT |
| GCAGAAGATGGAGGCCTACAACTTGCGCTTAGAGCAGAAACTTGATGAAAAAGAA |

-continued

| SEQUENCES |
|---|
| CAGGCTCTCTATTATGCTCGTTTGGAGGGAAGAAACAGAGCAAAACATCTGCGCCA |
| AACAATTCAGTCTCTACGACGACAGTTTAGTGGAGCTTTACCCTTGGCACAACAGG |
| AAAAGTTCTCCAAAACAATGATTCAACTACAAAATGACAAACTTAAGATAATGCAA |
| GAAATGAAAAATTCTCAACAAGAACATAGAAATATGGAGAACAAAACATTGGAGA |
| TGGAATTAAAATTAAAGGGCCTGGAAGAGTTAATAAGCACTTTAAAGGATACCAAA |
| GGAGCCCAAAAGGTAATCAACTGGCATATGAAATAGAAGAACTTCGTCTTCAAGA |
| ACTTAAACTAAATCGGGAATTAGTCAAGGATAAAGAAGAAATAAAATATTTGAATA |
| ACATAATTTCTGAATATGAACGTACAATCAGCAGTCTTGAAGAAGAAATTGTGCAA |
| CAGAACAAGTTTCATGAAGAAAGACAAATGGCCTGGGATCAAAGAGAAGTTGACC |
| TGGAACGCCAACTAGACATTTTTGACCGTCAGCAAAATGAAATACTAAATGCGGCA |
| CAAAAGTTTGAAGAAGCTACAGGATCAATCCCTGACCCTAGTTTGCCCCTTCCAAAT |
| CAACTTGAGATCGCTCTAAGGAAAATTAAGGAGAACATTCGAATAATTCTAGAAAC |
| ACGGGCAACTTGCAAATCACTAGAAGAGAAACTAAAAGAGAAAGAATCTGCTTTA |
| AGGTTAGCAGAACAAAATATACTGTCAAGAGACAAAGTAATCAATGAACTGAGGCT |
| TCGATTGCCTGCCACTGCAGAAAGAGAAAAGCTCATAGCTGAGCTAGGCAGAAAAG |
| AGATGGAACCAAAATCTCACCACACATTGAAAATTGCTCATCAAACCATTGCAAAC |
| ATGCAAGCAAGGTTAAATCAAAAGAAGAAGTATTAAAGAAGTATCAACGTCTTCT |
| AGAAAAAGCCAGAGAGGAGCAAAGAGAAATTGTGAAGAAACATGAGGAAGACCTT |
| CATATTCTTCATCACAGATTAGAACTACAGGCTGATAGTTCACTAAATAAATTCAAA |
| CAAACGGCTTGGGATTTAATGAAACAGTCTCCCACTCCAGTTCCTACCAACAAGCAT |
| TTTATTCGTCTGGCTGAGATGGAACAGACAGTAGCAGAACAAGATGACTCTCTTTCC |
| TCACTCTTGGTCAAACTAAAGAAAGTATCACAAGATTTGGAGAGACAAAGAGAAAT |
| CACTGAATTAAAAGTAAAAGAATTTGAAAATATCAAATTACAGCTTCAAGAAAACC |
| ATGAAGATGAAGTGAAAAAAGTAAAAGCGGAAGTAGAGGATTTAAAGTATCTTCT |
| GGACCAGTCACAAAAGGAGTCACAGTGTTTAAAATCTGAACTTCAGGCTCAAAAAG |
| AAGCAAATTCAAGAGCTCCAACAACTACAATGAGAAATCTAGTAGAACGGCTAAA |
| GAGCCAATTAGCCTTGAAGGAGAAACAACAGAAAGCACTTAGTCGGGCACTTTTAG |
| AACTCCGGGCAGAAATGACAGCAGCTGCTGAAGAACGTATTATTTCTGCAACTTCT |
| CAAAAAGAGGCCCATCTCAATGTTCAACAAATCGTTGATCGACATACTAGAGAGCT |
| AAAGACACAAGTTGAAGATTTAAATGAAAATCTTTTAAAATTGAAAGAAGCACTTA |
| AAACAAGTAAAAACAGAGAAAACTCACTAACTGATAATTTGAATGACTTAAATAAT |
| GAACTGCAAAAGAAACAAAAAGCCTATAATAAAATACTTAGAGAGAAAGAGGAAA |
| TTGATCAAGAGAATGATGAACTGAAAAGGCAAATTAAAAGACTAACCAGTGGATTA |
| CAGGGCAAACCCCTGACAGATAATAAACAAAGTCTAATTGAAGAACTCCAAAGGA |
| AAGTTAAAAAACTAGAGAACCAATTAGAGGGAAAGGTGGAGGAAGTAGACCTAAA |
| ACCTATGAAAGAAAGAATGCTAAAGAAGAATTAATTAGGTGGGAAGAAGGTAAA |
| AAGTGGCAAGCCAAAATAGAAGGAATTCGAAACAAGTTAAAAGAGAAAGAGGGGG |
| AAGTCTTTACTTTAACAAAGCAGTTGAATACTTTGAAGGATCTTTTTGCCAAAGCCG |
| ATAAAGAGAAACTTACTTTGCAGAGGAAACTAAAAACAACTGGCATGACTGTTGAT |

| SEQUENCES |
| --- |

CAGGTTTTGGGAATACGAGCTTTGGAGTCAGAAAAAGAATTGGAAGAATTAAAAAA

GAGAAATCTTGACTTAGAAAATGATATATTGTATATGAGGGCCCACCAAGCTCTTCC

TCGAGATTCTGTTGTAGAAGATTTACATTTACAAAATAGATACCTCCAAGAAAAACT

TCATGCTTTAGAAAAACAGTTTTCAAAGGATACATATTCTAAGCCTTCAATTTCAGG

AATAGAGTCAGATGATCATTGTCAGAGAGAACAGGAGCTTCAGAAGGAAAACTTG

AAGTTGTCATCTGAAAATATTGAACTGAAATTTCAGCTTGAACAAGCAAATAAAGA

TTTGCCAAGATTAAAGAATCAAGTCAGAGATTTGAAGGAAATGTGTGAATTTCTTA

AGAAAGAAAAAGCAGAAGTTCAGCGGAAACTTGGCCATGTTAGAGGGTCTGGTAG

AAGTGGAAAGACAATCCCAGAACTGGAAAAAACCATTGGTTTAATGAAAAAAGTA

GTTGAAAAAGTCCAGAGAGAAAATGAACAGTTGAAAAAAGCATCAGGAATATTGA

CTAGTGAAAAAATGGCTAATATTGAGCAGGAAAATGAAAAATTGAAGGCTGAATTA

GAAAAACTTAAAGCTCATCTTGGGCATCAGTTGAGCATGCACTATGAATCCAAGAC

CAAAGGCACAGAAAAAATTATTGCTGAAAATGAAAGGCTTCGTAAAGAACTTAAA

AAAGAAACTGATGCTGCAGAGAAATTACGGATAGCAAAGAATAATTTAGAGATATT

AAATGAGAAGATGACAGTTCAACTAGAAGAGACTGGTAAGAGATTGCAGTTTGCAG

AAAGCAGAGGTCCACAGCTTGAAGGTGCTGACAGTAAGAGCTGGAAATCCATTGTG

GTTACAAGAATGTATGAAACCAAGTTAAAAGAATTGGAAACTGATATTGCCAAAAA

AAATCAAAGCATTACTGACCTTAAACAGCTTGTAAAAGAAGCAACAGAGAGAGAA

CAAAAAGTTAACAAATACAATGAAGACCTTGAACAACAGATTAAGATTCTTAAACA

TGTTCCTGAAGGTGCTGAGACAGAGCAAGGCCTTAAACGGGAGCTTCAAGTTCTTA

GATTAGCTAATCATCAGCTGGATAAAGAGAAAGCAGAATTAATCCATCAGATAGAA

GCTAACAAGGACCAAAGTGGAGCTGAAAGCACCATACCTGATGCTGATCAACTAAA

GGAAAAAATAAAAGATCTAGAGACACAGCTCAAAATGTCAGATCTAGAAAAGCAG

CATTTGAAGGAGGAAATAAAGAAGCTGAAAAAAGAACTGGAAAATTTTGATCCTTC

ATTTTTTGAAGAAATTGAAGATCTTAAGTATAATTACAAGGAAGAAGTGAAGAAGA

ATATTCTCTTAGAAGAGAAGGTAAAAAAACTTTCAGAACAATTGGGAGTTGAATTA

ACTAGCCCTGTTGCTGCTTCTGAAGAGTTTGAAGATGAAGAAGAAAGTCCTGTTAAT

TTCCCCATTTACTAAAGGTCACCTATAAACTTTGTTTCATTTAACTATTTATTAACTT

TATAAGTTAAATATACTTGGAAATAAGCAGTTCTCCGAACTGTAGTATTTCCTTCTC

ACTACCTTGTACCTTTATACTTAGATTGGAATTCTTAATAAATAAAATTATATGAAA

TTTTCAACTTATTAAAAAAAAAAAAAAAAAA

>AAV8 capsid protein amino acid sequence
(SEQ ID NO: 9)
MAADGYLPDWLEDNLSEGIREWWALKPGAPKPKANQQKQDDGRGLVLPGYKYLGPF

NGLDKGEPVNAADAAALEHDKAYDQQLQAGDNPYLRYNHADAEFQERLQEDTSFGG

NLGRAVFQAKKRVLEPLGLVEEGAKTAPGKKRPVEPSPQRSPDSSTGIGKKGQQPARKR

LNFGQTGDSESVPDPQPLGEPPAAPSGVGPNTMAAGGGAPMADNNEGADGVGSSSGN

WHCDSTWLGDRVITTSTRTWALPTYNNHLYKQISNGTSGGATNDNTYFGYSTPWGYF

DFNRFHCHFSPRDWQRLINNNWGFRPKRLSFKLFNIQVKEVTQNEGTKTIANNLTSTIQ

| SEQUENCES |
|---|
| VFTDSEYQLPYVLGSAHQGCLPPFPADVFMIPQYGYLTLNNGSQAVGRSSFYCLEYFPS |
| QMLRTGNNFQFTYTFEDVPFHSSYAHSQSLDRLMNPLIDQYLYYLSRTQTTGGTANTQT |
| LGFSQGGPNTMANQAKNWLPGPCYRQQRVSTTTGQNNNSNFAWTAGTKYHLNGRNS |
| LANPGIAMATHKDDEERFFPSNGILIFGKQNAARDNADYSDVMLTSEEEIKTTNPVATE |
| EYGIVADNLQQQNTAPQIGTVNSQGALPGMVWQNRDVYLQGPIWAKIPHTDGNFHPSP |
| LMGGFGLKHPPPQILIKNTPVPADPPTTFNQSKLNSFITQYSTGQVSVEIEWELQKENSKR |
| WNPEIQYTSNYYKSTSVDFAVNTEGVYSEPRPIGTRYLTRNL |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels tdistinguish one claim element having a certain name from another element having a same name (but for use of the ordinal term) to distinguish the claim elements. o

What is claimed is:

1. An isolated nucleic acid comprising:
   (i) a first region comprising a first adeno-associated virus (AAV) inverted terminal repeat (ITR), or a variant thereof; and,
   (ii) a second region comprising a transgene encoding a CEP290 protein fragment, wherein the CEP290 protein fragment comprises at least 500 contiguous amino acids of SEQ ID NO: 1, wherein the CEP290 fragment comprises no more than 700 contiguous amino acids of SEQ ID NO: 1, wherein the CEP290 fragment comprises or consists of the sequence set forth in SEQ ID NO: 3, and wherein the CEP290 fragment does not comprise amino acids 1695 to 1966 of SEQ ID NO: 1.

2. The isolated nucleic acid of claim 1, wherein said CEP290 fragment is encoded by a nucleic acid comprising or consisting of the sequence of SEQ ID NO: 6.

3. The isolated nucleic acid of claim 1, wherein the transgene further comprises a promoter.

4. The isolated nucleic acid of claim 3, wherein the promoter is a chicken beta-actin (CBA) promoter, or a tissue specific promoter selected from the group consisting of: an eye-specific promoter, a retinoschisin promoter, K12 promoter, a rhodopsin promoter, a rod-specific promoter, a cone-specific promoter, a rhodopsin kinase promoter, and an interphotoreceptor retinoid-binding protein proximal (IRBP) promoter.

5. The isolated nucleic acid of claim 1, further comprising a third region comprising a second adeno-associated virus (AAV) inverted terminal repeat (ITR), or a variant thereof.

6. The isolated nucleic acid of claim 1, wherein the first region is an AAV2 ITR or a variant thereof.

7. A vector comprising the isolated nucleic acid of claim 1.

8. A host cell comprising the isolated nucleic acid of claim 1.

9. A recombinant adeno-associated virus (rAAV) comprising:
(i) a capsid protein; and,
(ii) the isolated nucleic acid of claim 1.

10. The rAAV of claim 9, wherein the capsid protein is AAV8 capsid protein or AAV5 capsid protein.

11. The rAAV of claim 9, wherein the capsid protein comprises the sequence set forth in SEQ ID NO: 9.

12. The rAAV of claim 9, wherein the rAAV is a self-complementary AAV (scAAV).

13. The rAAV of claim 9, wherein the rAAV is formulated for delivery to an eye of a subject.

14. A method for treating an ocular ciliopathy in a subject in need thereof, the method comprising administering to a subject having an ocular ciliopathy a therapeutically effective amount of the isolated nucleic acid of claim 1, wherein said administering is via subretinal injection or intravitreal injection.

15. The isolated nucleic acid of claim 1 further comprising a third region, wherein the third region is an AAV2 ITR or a variant thereof.

16. The vector of claim 7, wherein the vector is a plasmid.

* * * * *